United States Patent [19]

Goto et al.

[11] Patent Number: 5,462,934
[45] Date of Patent: Oct. 31, 1995

[54] CONDENSED HETEROCYCLIC KETONE DERIVATIVES AND THEIR USE

[75] Inventors: Giichi Goto, Osaka; Masaomi Miyamoto; Yuji Ishihara, both of Hyogo, all of Japan

[73] Assignee: Takeda Chemical Industries, Osaka, Japan

[21] Appl. No.: 26,041

[22] Filed: Mar. 4, 1993

[30] Foreign Application Priority Data

| Mar. 9, 1992 | [JP] | Japan | 4-050960 |
| Apr. 17, 1992 | [JP] | Japan | 4-097848 |
| Jun. 5, 1992 | [JP] | Japan | 4-145852 |
| Aug. 6, 1992 | [JP] | Japan | 4-210225 |
| Sep. 29, 1992 | [JP] | Japan | 4-259606 |

[51] Int. Cl.$^6$ .................. A61K 31/55; C07D 223/16; C07D 401/10; C07D 403/10
[52] U.S. Cl. .................. 514/183; 514/213; 514/253; 514/307; 514/311; 514/314; 514/323; 514/415; 514/416; 540/476; 540/542; 540/593; 540/594; 544/363; 544/373; 546/146; 546/168; 546/200; 546/201; 548/482; 548/491; 548/950; 548/953
[58] Field of Search .................. 540/542, 593, 540/594, 476; 514/213, 307, 311, 314, 253, 415, 416, 323, 183; 544/363, 373; 548/482, 491; 546/200, 201

[56] References Cited

U.S. PATENT DOCUMENTS

| 4,064,255 | 12/1977 | Champseix et al. | 424/267 |
| 4,208,417 | 6/1980 | Uzan | 424/267 |
| 4,521,606 | 6/1985 | Asselin et al. | 548/503 |
| 4,849,431 | 7/1989 | Sugimoto et al. | 514/331 |
| 4,895,841 | 1/1990 | Sugimoto et al. | 514/212 |
| 4,916,128 | 4/1990 | Jonas et al. | 514/213 |

FOREIGN PATENT DOCUMENTS

| 35228 | 9/1981 | European Pat. Off. |
| 229391 | 7/1987 | European Pat. Off. |
| 294647 | 12/1988 | European Pat. Off. |
| 326106 | 8/1989 | European Pat. Off. |
| 351282 | 1/1990 | European Pat. Off. |
| 378207 | 7/1990 | European Pat. Off. |
| 468187 | 1/1992 | European Pat. Off. |
| 487071 | 5/1992 | European Pat. Off. |
| WO9103243 | 3/1991 | WIPO |

OTHER PUBLICATIONS

Schnabel, "New Alzheimer's therapy suggested", Science, vol. 260 (Jun. 1993), pp. 1719–1720.
Cecil Textbook of Medicine, 19th ed. (1992), Wyneaarden, M. R. editor, pp. 2075–2078.
European Search Report for EP Application No. 93103614.9 (Jun. 1993).
Chemical Abstracts 107, 190332h, 1987, Dauksas et al.
Chemical Abstracts 89, 36594y, 1978, Khaidarov et al.
Chemical Abstracts 87, 152125d, 1977, Hirose et al.
Chemical Abstracts 104, 168373p, 1986, Masazumi et al.
Chemical Abstracts 91, 211631y, 1979, Numanov et al.
Helvetica Chemica Acta, 51, 1616–1628, 1968, Troxler et al.
U.S. Ser. No. 07/796,430 filed Nov. 22, 1991, Goto et al., Now U.S. Pat. No. 5,273,974 issued Dec. 28, 1993.

*Primary Examiner*—Philip I. Datlow
*Attorney, Agent, or Firm*—Foley & Lardner

[57] ABSTRACT

A compound of the formula:

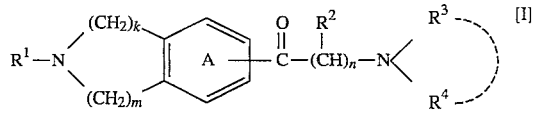

wherein $R^1$ is H or an optionally substituted hydrocarbon or acyl group; ring A is an optionally further substituted benzene ring; n is an integer of 1 to 10; $R^2$, $R^3$ and $R^4$ are H or an optionally substituted hydrocarbon group; $R^3$ and $R^4$ may form an optionally substituted heterocyclic group, taken together with the adjacent nitrogen atom; k is an integer of 0 to 3; and m is an integer of 1 to 8; provided that when k=0 and m=2, n is an integer of not less than 2 or a pharmaceutically acceptable salt thereof, exhibiting excellent cholinesterase inhibitory activity and monoamine reuptake inhibitory activity, thus being useful as therapeutic/prophylactic medicaments of senile dementia.

27 Claims, No Drawings

CONDENSED HETEROCYCLIC KETONE DERIVATIVES AND THEIR USE

This invention relates to novel condensed heterocyclic ketone derivatives and salts thereof. These compounds are useful as medicines, more specifically, cholinesterase inhibitors, especially as therapeutic or/and prophylactic agents for senile dementia, Alzheimer's disease and so on.

With an increasing number of elderly people, there have been proposed various compounds having therapeutic and/or prophylactic actions on senile dementia. Among them, in physostigmine, a naturally-occurring cholinesterase inhibitor, there has been found therapeutic or/and prophylactic actions on senile dementia (International Journal of Clinical Pharmacology, Therapy and Toxicology, Vol. 29, No. 1, p. 23–37(1991) etc.). Physostigmine is, however, possessed of such drawbacks as relatively short duration of the action and high toxicity.

On the other hand, various heterocyclic compounds have been proposed as synthetic medicines (for example, in EP-A-0,378,207, U.S. Pat. No. 4,849,431 and U.S. Pat. No. 4,895,841, cholinesterase inhibitors having N-containing heterocyclic ring being described, and, in JPA S52(1977)-72829 and JPA S55(1980)-9070, antidepressant or antianxiety drugs having chemical structures analogous to the above-mentioned cholinesterase inhibitor being described).

More specifically, in EP-A-0,378,207, there are disclosed cyclic amine compounds represented by the formula:

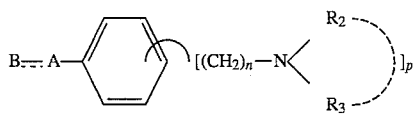

wherein B stands for an optionally substituted saturated or unsaturated 5- to 7-membered azaheterocyclic group; A stands for a bond or an alkylene group or alkenylene group optionally substituted with a hydrocarbon residue, oxo group or hydroxyl group; ----- means a single bond or double bond (provided that, when A stands for a bond, ----- means single bond); $R_2$ and $R_3$ independently stand for H or an optionally substituted hydrocarbon residue (provided that they are not H at the same time) or may form a cyclic amino group taken together with the adjacent nitrogen atom; n denotes 0, 1 or 2; p denotes 1 or 2, or salts thereof, practically the following compound, among others.

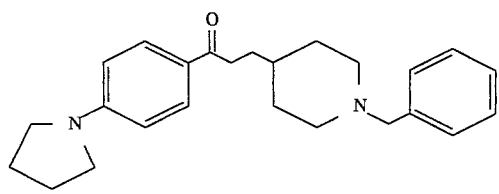

In U.S. Pat. No. 4,849,431, there are disclosed piperidine derivatives represented by the formula:

$$R^1-X-\text{\textcircled{A}}-R^2$$

wherein $R^1$ stands for a monovalent group derived from a member selected from optionally substituted benzene, pyridine, pyrazine, indole, anthraquinone, quinoline, optionally substituted phthalimide, homophthalimide, pyridine carboxylimide, pyridine-N-oxide, pyrazine carboxylimide, naphthalenedicarboxylimide, optionally substituted quinazolinedione, 1,8-naphthalimide, bicyclo[2,2,2]oct-5-ene-2,3-dicarboxylimide and pyromellylimide;

X stands for a group shown by the formula: $-(CH_2)_m-$ (wherein m denotes a whole number of 0 to 7), a group shown by the formula: $-O(CH_2)_n-$, a group shown by the formula: $-S(CH_2)_n$, a group shown by the formula: $-NH(CH_2)_n-$, a group shown by the formula: $-SO_2NH(CH_2)_n-$, a group shown by the formula: $-NH-CO-(CH_2)_n-$, a group shown by the formula: $-NH(CH_2)_n-CO-$, a group shown by the formula: $-CO-NR^3-(CH_2)_n-$ (in the definition of X, n in the above formulae denotes a whole number of 1 to 7, and $R^3$ stands for a lower alkyl or benzyl group), a group shown by the formula: $-O-CH_2CH_2CH(CH_3)-$, a group shown by the formula: $-O-CH_2CH_2CH=$, or a group shown by the formula: $-O-CH_2CH(OH)CH_2-$;

Ring A stands for a group shown by the formula:

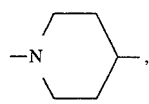

a group shown by the formula:

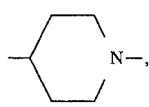

a group shown by the formula:

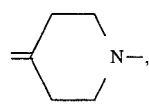

a group shown by the formula:

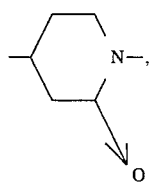

$R^2$ stands for H, a lower alkyl group, optionally substituted benzyl group, optionally substituted benzoyl group, pyridyl group, 2-hydroxyethyl group, pyridylmethyl group, or a group shown by the formula:

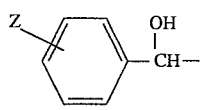

(wherein Z stands for a halogen atom), or pharmaceutically acceptable salts thereof, practically the following compound.

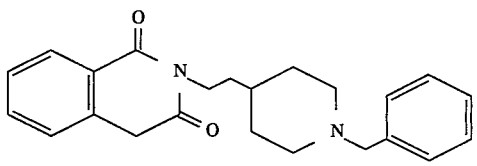

In U.S. Pat. No. 4,895,841, there are disclosed cyclic amine derivatives represented by the general formula:

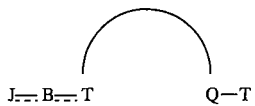

wherein J stands for (a) optionally substituted groups shown as follows; (1) phenyl group, (2) pyridyl group, (3) pyrazyl group, (4) quinolyl group, (5) cyclohexyl group, (6) quinoxalyl group or (7) furyl group,
(b) a mono- or di-valent group selected from the following groups optionally substituted with a phenyl group; (1) indanyl, (2) indanonyl, (3) indenyl, (4) indenonyl, (5) indanedionyl, (6) tetralonyl, (7) benzsperonyl, (8) indanolyl, (9) a group shown by the formula:

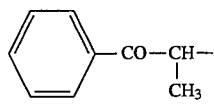

(c) a monovalent group derived from a cyclic amido compound,
(d) a lower alkyl group, or
(e) a group shown by the formula: $R^1$—CH=CH— (wherein $R^1$ stands for H or a lower alkoxycarbonyl group); B stands for a group shown by the formula: —$(C(R^2)H)_n$—, a group shown by the formula: —CO—$(C(R^2)H)_n$—, a group shown by the formula: —$NR^2$—$(C(R^2)H)_n$— (wherein $R^2$ stands for H, a lower alkyl group, acyl group, a lower alkylsulfonyl group, optionally substituted phenyl group or benzyl group), a group shown by the formula: —CO—$NR^4$—$(C(R^2)H)_n$— (wherein $R^4$ stands for H, a lower alkyl group or phenyl group), a group shown by the formula: —CH=CH—$(C(R^2)H)_n$—, a group shown by the formula: —O—COO—$(C(R^2)H)_n$—, a group shown by the formula: —O—CO—NH—$(C(R^2)H)_n$—, a group shown by the formula: —NH—CO—$(C(R^2)H)_n$—, a group shown by the formula: —$CH_2$—CO—NH—$(C(R^2)H)_n$—, a group shown by the formula: —CO—NH—$(C(R^2)H)_n$—, a group shown by the formula: —C(OH)H—$(C(R^2)H_n$— (in the above formulae, n denotes 0 or a whole number of 1 to 10, $R^2$ stands for H or a methyl group in the form of the alkylene group shown by the formula: —$(C(R^2)H)_n$— which is unsubstituted or having one or more than one methyl group), a group shown by the formula: =(CH—CH=CH)$_b$— (wherein b denotes a whole number of 1 to 3), a group shown by the formula: =CH—$(CH_2)_c$— (wherein c denotes a whole number of 1 to 9), a group shown by the formula: =(CH—CH)$_d$= (wherein d denotes 0 or a whole number of 1 to 5), a group shown by the formula: —CO—CH—CH—$CH_2$—, a group shown by the formula: —C($CH_3$)H—CO—NH—$CH_2$—, a group shown by the formula: —CH=CH—CO—NH—$(CH_2)_2$—, the group shown by the formula: —NH—, the group shown by the formula: —O—, the group shown by the formula: —S—, dialkylaminoalkylcarbonyl group or a lower alkoxycarbonyl group,
T stands for N or C,
Q stands for N, C or a group shown by the formula: >N→O,
K stands for H, an optionally substituted phenyl group, an arylalkyl group optionally substituted with a phenyl group, a cinnamyl group optionally substituted with a phenyl group, a lower alkyl group, pyridylmethyl group, cycloalkylalkyl group, adamantanemethyl group, furylmethyl group, cycloalkyl group, a lower alkoxycarbonyl group or acyl group,
q denotes a whole number of 1 to 3, and ----- denotes a single bond or a double bond or their pharmaceutically acceptable salts, a practical embodiment being the following compound.

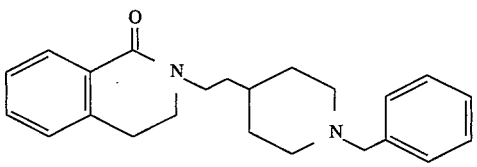

In U.S. Pat. No. 4,064,255, there are disclosed pharmaceutical compositions containing a compound represented by the general formula:

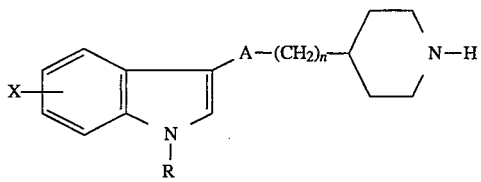

wherein R stands for H, a $C_{1-4}$ alkyl group or an aralkyl group whose alkyl moiety has one or two carbon atoms; X stands for H or a halogen atom, alkyl, alkoxy or alkylthio group, each optionally having one to four carbon atoms, trifluoromethyl, nitro, hydroxyl or unsubstituted amino group or amino group substituted with one or two alkyl groups or acyl or alkylsulfonyl group; A stands for the group —CO— or the group —$CH_2$—; and n denotes 0, 1 or 2, or a pharmaceutically acceptable salt thereof, which are useful in treatment of pathological conditions caused by disturbances in serotonin systems, and, in U.S. Pat. No. 4,208,417, there are disclosed indole derivatives represented by the general formula:

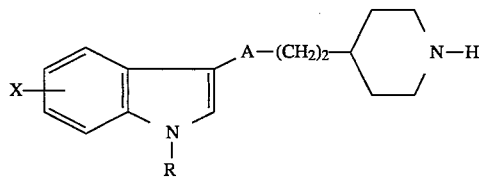

wherein R stands for H, a $C_{1-4}$ alkyl group or an aralkyl group whose alkyl moiety has one or two carbon atoms; X stands for H or a halogen atom, alkyl group, alkoxy group or an alkylthio group whose alkyl moiety has one to four carbon atoms; A stands for —CO— or —$CH_2$—; and n denotes 1 or 2, which are medicinally active compounds having affinity for the $^3$H-diazepam binding site.

Further, in WO91/03243, there are disclosed compounds represented by the general formula:

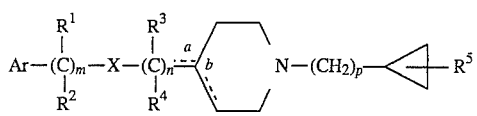

wherein m denotes 0 to 3; n denotes 0 to 3; m and n are not 0 simultaneously; p denotes 0 to 3; X stands for O S, SO, $SO_2$, $NR^6$, $CR^7R^8$, CO or CHOH; $R^1$, $R^3$ and $R^7$ each stand for H, $C_{1-5}$ alkyl, halogen, $NR^{10}R^{11}$, OH, COOH, $C_{2-6}$ carboalkoxy, CN, Ar, $C_{1-5}$ alkoxy or $C_{1-5}$ alkylthio; $R^2$, $R^4$ and $R^8$ each stand for H, $C_{1-5}$ alkyl, $C_{2-6}$ carboalkoxy, CN, $C_{1-5}$ alkoxy or $Ar^1$; when X is O, S, SO, $SO_2$ or $NR^6$, $R^1$, $R^2$, $R^3$ and $R^4$ are not $C_{1-5}$ alkoxy, $C_{1-5}$ alkylthio, $NR^{10}R^{11}$ or OH; $R^5$ stands for H, alkyl, halogen, OH or alkenyl; $R^6$ stands for H, $C_{1-5}$ alkyl or $Ar^1$; Ar and $Ar^1$ respectively stand for naphthyl, pyridyl, pyrimidyl, indolyl, quinolinyl or phenyl, these groups being optionally substituted with $C_{1-3}$ alkyl, $C_{1-3}$ alkoxy, $C_{1-3}$ haloalkyl having 1 to 7 halogen atoms, SH, $S(O)_t$—$C_{1-3}$ alkyl ( t denotes 1, 2 or 3 ), $C_{2-6}$ dialkylamino, halogen, $C_{1-3}$ alkylamino, $NH_2$, CN, $NO_2$, $SO_3H$, tetrazole, COOH, $C_{2-6}$ carboalcoxy, $CONH_2$, $SO_2NO_2$, $COR^9$, $CONR^{12}R^{13}$, $SO_2NR^{12}R^{13}$, $Ar^2$, $OAr^2$ or $SAr^2$; $Ar^2$ stands for a naphthyl group or phenyl group, these groups being optionally substituted with $C_{1-3}$ alkyl, $C_{1-3}$ haloalkyl having one to seven halogen atoms, $C_{1-3}$ alkoxy, halogen or $C_{1-3}$ alkylthio; $R^9$, $R^{10}$, $R^{11}$, $R^{12}$ and $R^{13}$ respectively stand for H, $C_{1-5}$ alkyl or phenyl, $R^{10}$ and $R^{11}$ may, taken together, form $C_{3-6}$ alkylene chain, $R^{12}$ and $R^{13}$ may, taken together, form $C_{3-6}$ alkylene chain; a or b shows double bond or single bond, and both are not double bond, or pharmaceutically acceptable salts thereof, which are useful in the treatment of physiological or drug-induced psychosis or dyskinesia.

On the other hand, a variety of O-containing or S-containing condensed ketone derivatives have been produced, and their biological activity and pharmacological actions are disclosed. However, nothing was disclosed as to action as cholinesterase inhibitors and therapeutic and/or prophylactic agents of senile dementia.

More specifically, in Chem. Abstr., 107, 190332h (1987), there is disclosed that the compound represented by the general formula:

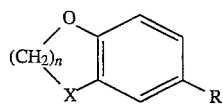

(wherein R=Ac, COEt, COPr, $COCHMe_2$, $CO(CH_2)_2Cl$, $CO(CH_2)_3Cl$, $COCH_2NMe_2$, $CO(CH_2)_2NMe_2$, $CO(CH_2)_3NMe_2$, and salts of them or R=COCH=CHPh, $X=CH_2$ or O, n=1, 2 or 3) has an antiinflammatory action. In Chem. Abstr., 89, 36594y (1978), there is disclosed that the compound represented by the general formula:

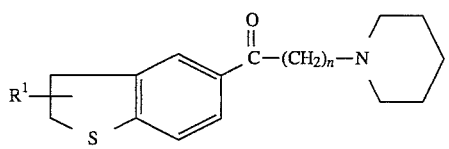

(wherein $R^1$=H, Me; n=2, 3) has a convulsive action, an arterial blood pressure lowering action and a local anesthetic action.

In Chem. Abstr., 87, 152125d (1977), there is disclosed that the compound represented by the general formula:

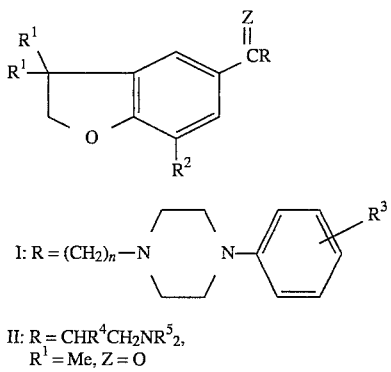

wherein $R^1$=H, Me; R=H, Cl, Me; $R^3$=H, F, Me, OMe, Cl; n=1, 2, 3; Z=O, OH, H (for Compound I) or $R^2$=H, Cl; $R^4$=H, Me; $NR^5$=$NMe_2$, morpholino, piperidino (for Compound 4 II) has an antidepressant action.

In EP-163,537, there is disclosed the compound represented by the general formula:

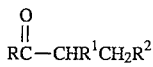

(wherein R=4-cycloalkylphenyl, 3,4-methylenedioxyphenyl, 2,3-dihydro-5-benzofuranyl; $R^1$=alkyl, cycloalkyl, cyclopentylmethyl; $R^2$=optionally substituted pyrrolidino, piperidino, hexahydro-1H-azepin- 1-yl, octahydro-1-azocinyl) has a muscle-relaxing action.

In Chem. Abstr., 91, 211631y (1979), there is disclosed that the compound represented by the formula:

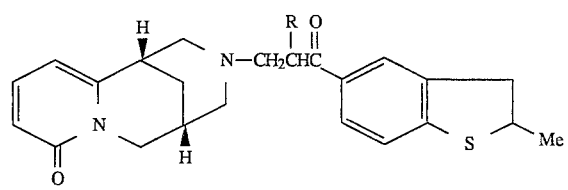

(wherein R=H, Me) is synthesized as a derivative of cytisine, an alkaloid, having an anticholinergic action.

And, as N-containing condensed heterocyclic ketone derivatives, in Helvetica Chimica Acta, 51, 1616 (1968), the compounds represented by the formula (A) and the formula (B):

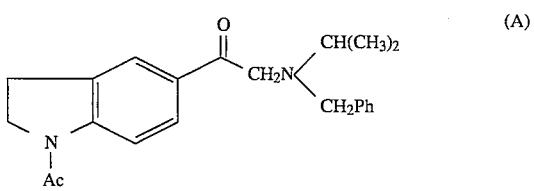

(B)

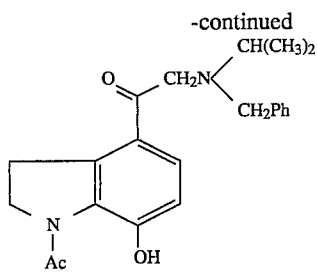

are disclosed as intermediates for synthesizing alkanolamine, an agent acting on the sympathetic nervous system, represented by the formula (C):

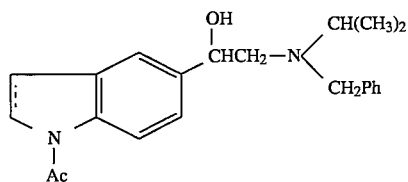

In these days when senile dementia is increasing, however, there is needed development of excellent therapeutic and/or prophylactic agents having a stronger action and longer action and less toxicity than the compounds already known to have therapeutic and/or prophylactic efficacy on senile dementia.

The present invention was accomplished by succeeding in creation of novel compounds having a condensed heterocyclic group of specific chemical structure and by finding that these novel compounds have unexpectedly excellent cholinesterase inhibitory activity and monoamine reuptake inhibitory activity, thus being useful as therapeutic and/or prophylactic agents for senile dementia. More specifically, the present invention relates to;

(1) condensed heterocyclic ketone derivatives of the formula:

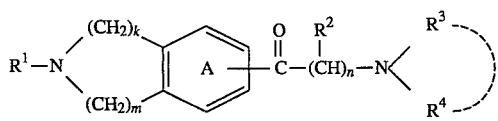  [I]

wherein $R^1$ stands for H, an optionally substituted hydrocarbon group or an optionally substituted acyl group; ring A stands for an optionally further substituted benzene ring; n denotes a whole number of 1 to 10; $R^2$, $R^3$, and R independently stand for H or an optionally substituted hydrocarbon group; $R^3$ and $R^4$ may form an optionally substituted heterocyclic group, taken together with the adjacent nitrogen atom; the $R^2$'s may be different from one another in the repetition of n; k denotes a whole number of 0 to 3; and m denotes a whole number of 1 to 8; provided that when k=0 and m=2, n denotes a whole number of not less than 2, or salts thereof, (2) a method of producing the compound [I] or a salt thereof, which comprises reacting a compound represented by the formula:

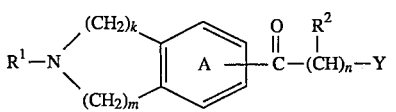  [II]

wherein Y stands for a leaving group; $R^1$, ring A, $R^2$, n, k and m are of the same meanings as defined above, or a salt thereof with a compound represented by the formula:

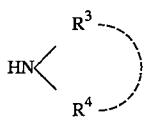  [III]

wherein $R^3$ and $R^4$ are of the same meanings as defined above, or a salt thereof, (3) a method of producing a compound represented by the formula:

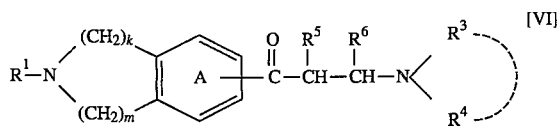  [VI]

wherein $R^1$, $R^3$, $R^4$, ring A, k and m are of the same meanings as defined above, $R^5$ stands for H or an optionally substituted hydrocarbon group, and $R^6$ stands for H or an optionally substituted hydrocarbon group, or a salt thereof, which comprises reacting a compound represented by the formula:

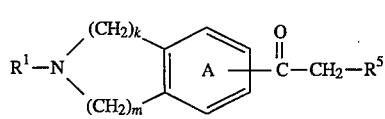  [IV]

wherein $R^1$, $R^5$, ring A, k and m are of the same meanings as defined above, or a salt thereof and a compound represented by the formula:

$R^6$—CHO  [V]

wherein $R^6$ is of the same meaning as defined above with a compound represented by the formula

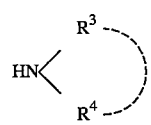  [III]

wherein $R^3$ and $R^4$ are Of the same meanings as defined above, or a salt thereof, (4) compounds represented by the formula:

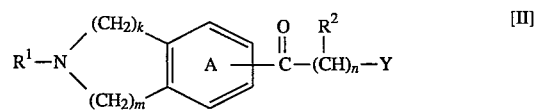  [II]

wherein Y, $R^1$, ring A, $R^2$, n, k and m are of the same meanings as defined above, or salts thereof, (5) a cholinesterase inhibitor, which contains a condensed heterocyclic ketone derivative represented by the formula:

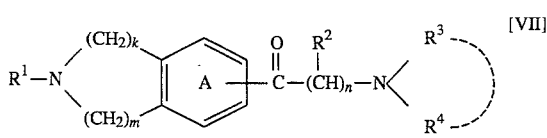

wherein $X^1$ stands for $R^1$—N (wherein $R^1$ stands for H, an optionally substituted hydrocarbon group or an optionally substituted acyl group), O or S; ring A stands for an optionally further substituted benzene ring; n denotes a whole number of 1 to 10; $R^2$, $R^3$ and $R^4$ independently stand for H or an optionally substituted hydrocarbon group; $R^3$ and $R^4$ may form an optionally substituted heterocyclic group, taken together with the adjacent nitrogen atom; $R^2$'s may be different from one another in the repetition of n; k denotes a whole number of 0 to 3; and m denotes a whole number of 1 to 8, or a salt thereof, and (6) a therapeutic and/or prophylactic agent for senile dementia which contains the compound [VII] or a salt thereof.

The compound [I] or salts thereof of this invention are novel compounds having structural characteristics in that the heterocyclic ring containing a hetero atom (O, S or N) condensed on the benzene ring is a saturated one and a substituent

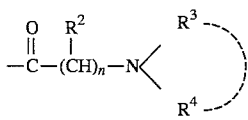

is bonded to the carbon atom on the benzene ring, and, based on these characteristics, these compounds show excellent therapeutic or/and prophylactic actions for senile dementia.

In the foregoing formulae, $R^1$ stands for H, an optionally substituted hydrocarbon group or an optionally substituted acyl group.

$R^2$ stands for H or an optionally substituted hydrocarbon group, and the $R^2$'s may be different from one another in the repetition of n.

$R^3$ and $R^4$ stand for H or an optionally substituted hydrocarbon group, and, they may form, taken together with the adjacent nitrogen atom, an optionally substituted heterocyclic group.

$R^5$ and $R^6$ stand for H or an optionally substituted hydrocarbon group.

Examples of "hydrocarbon group" of the "optionally substituted hydrocarbon group" shown by the above-mentioned $R^1$, $R^2$, $R^3$, $R^4$, $R^5$ and $R^6$ include chain-like or cyclic or their combined type $C_{1-18}$ hydrocarbon groups. Examples of the chain-like hydrocarbon groups include straight-chain or branched $C_{1-11}$ alkyl groups (e.g. methyl, ethyl, n-propyl, i-propyl, n-butyl, i-butyl, tert-butyl, n-pentyl, n-hexyl, etc.), straight-chain or branched $C_{2-4}$ alkenyl groups (e.g. vinyl, allyl, 2-butenyl, etc.) and straight-chain or branched $C_{2-4}$ alkynyl groups (e.g. propargyl, 2-butynyl, etc.). Examples of the cyclic hydrocarbon groups include $C_{3-7}$ monocyclic cycloalkyl groups (e.g. cyclobutyl, cyclopentyl, cyclohexyl etc.), C8–14 bridge ring saturated hydrocarbon groups (e.g. bicyclo[3.2.1]oct-2-yl, bicyclo[3.3.1]non-2-yl, adamantan-1-yl, etc.), $C_{6-14}$ aryl groups (e.g. phenyl group, naphthyl group, etc.), among others.

Examples of hydrocarbon groups composed of chain-like and cyclic ones include C7–18 aralkyl (phenyl-$C_{1-12}$ alkyl or naphthyl-$C_{1-8}$ alkyl such as phenylmethyl, phenylethyl, phenylpropyl, phenylbutyl, phenylpentyl, phenylhexyl or α-naphthylmethyl; diphenyl-$C_{1-3}$ alkyl such as diphenylm- ethyl or diphenylethyl), $C_{6-14}$ aryl-$C_{2-12}$ alkenyl (phenyl-$C_{2-12}$ alkenyl such as styryl, cinnamyl, 4-phenyl-2-butenyl or 4-phenyl-3-butenyl), $C_{6-14}$ aryl-$C_{2-12}$ alkynyl (phenyl-$C_{2-12}$ alkynyl such as phenylethynyl, 3-phenyl- 2-propynyl or 3-phenyl-1-propynyl), $C_{3-7}$ cycloalkyl-$C_{1-6}$ alkyl (e.g. cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropyl, cyclopropylbutyl, cyclobutylbutyl, cyclopentylbutyl, cyclohexylbutyl, cycloheptylbutyl, cyclopropylpentyl, cyclobutylpentyl, cyclopentylpentyl, cyclohexylpentyl, cycloheptylpentyl, cyclopropylhexyl, cyclobutylhexyl, cyclopentylhexyl, cyclohexylhexyl, cycloheptylhexyl, etc.).

Preferable examples of the "hydrocarbon group" of the "optionally substituted hydrocarbon group" shown by $R^1$, $R^2$, $R^3$, $R^4$, $R^5$ and $R^6$ include straight-chain or branched $C_{1-11}$ alkyl groups, especially straight-chain or branched $C_{1-7}$ alkyl groups (e.g. methyl, ethyl, n-propyl, i-propyl, n-butyl, i-butyl, tert-butyl, n-pentyl, n-hexyl, etc.) or $C_{7-18}$ aralkyl groups, especially $C_{7-10}$ aralkyl groups (e.g. phenyl-$C_{1-4}$ alkyl such as phenylmethyl, phenylethyl and phenylpropyl).

The hydrocarbon groups shown by $R^1$, $R^2$, $R^3$, $R^4$, $R^5$ and $R^6$ may optionally have substituents, and, as such substituents, use is properly made of those generally used as substituents of hydrocarbon groups. More specifically, as substituents which the above-mentioned $C_{1-11}$ alkyl, $C_{2-4}$ alkenyl, $C_{2-4}$ alkynyl, $C_{3-7}$ monocyclic cycloalkyl and $C_{8-14}$ bridge ring saturated hydrocarbon groups may have, use is made of one to five of those selected from halogen atoms (e.g. fluorine, chlorine, bromine, iodine, etc.), nitro group, cyano group, hydroxyl group, $C_{1-4}$ alkoxy groups (e.g. methoxy, ethoxy, propyloxy, butyloxy, isopropyloxy, etc.), $C_{1-4}$ alkylthio groups (e.g. methylthio, ethylthio, propylthio, etc.), amino group, mono- or di- $C_{1-4}$ alkylamino group (e.g. methylamino, ethylamino, propylamino, dimethylamino, diethylamino, etc.), 5- to 7-membered cyclic amino groups (e.g. pyrrolidino, piperidino, morpholino, etc.), $C_{1-4}$ alkyl-carbonylamino groups (e.g. acetylamino, propionylamino, butyrylamino, etc.), $C_{1-4}$ alkylsulfonylamino groups (e.g. methylsulfonylamino, ethylsulfonylamino, etc.), $C_{1-4}$ alkoxy-carbonyl groups (e.g. methoxycarbonyl, ethoxycarbonyl, propoxycarbonyl, etc.), carboxyl group, $C_{1-6}$ alkyl-carbonyl groups (e.g. methylcarbonyl, ethylcarbonyl, propylcarbonyl, etc.), carbamoyl group, mono- or di-$C_{1-4}$ alkylcarbamoyl groups (e.g. methylcarbamoyl, ethylcarbamoyl, etc.), alkylsulfonyl groups (e.g. methylsulfonyl, ethylsulfonyl, propylsulfonyl, etc.), $C_{1-4}$ alkylenedioxy (e.g. methylenedioxy, etc.), 5- or 6- membered heterocyclic groups or its condensed ring containing 1 to 3 hetero atoms selected from N,S and O other than carbon atoms which may be substituted with a $C_{1-4}$ alkyl (e.g. pyridyl, pyridinyl, pyrazinyl, pyrimidinyl, quinolinyl, isoquinolinyl, naphthylidinyl, thiazolyl, benzothiazolyl, benzoxazolyl, furyl, furanyl, thiophenyl, etc.).

Examples of the substituents, which the $C_{6-14}$ aryl groups shown by $R^1$, $R^2$, $R^3$, $R^4$, $R^5$ and $R^6$ may have, include $C_{1-4}$ alkyl groups (e.g. methyl, ethyl, propyl, butyl, etc.), halogen atoms (e.g. fluorine, chlorine, bromine, iodine, etc.), nitro group, cyano group, hydroxyl group, $C_{1-4}$ alkoxy groups (e.g. methoxy, ethoxy, propyloxy, butyloxy, isopropyloxy, etc.), $C_{1-4}$ alkylthio groups (e.g. methylthio, ethylthio, propylthio, isopropylthio, butylthio, etc.), amino group, mono- or di-$C_{1-4}$ alkylamino groups (e.g. methylamino, ethylamino, propylamino, dimethylamino, diethylamino, etc.), 5- to 7-membered cyclic amino groups (e.g. pyrrolidino, piperidino, morpholino, etc.), $C_{1-4}$ alkyl-carbonylamino groups (e.g. acetylamino, propionylamino, butyrylamino, etc.), $C_{7-18}$ aralkyloxy (e.g. phenylmethoxy, phenylethoxy, etc.), aminocarbonyloxy group, mono- or di-$C_{1-4}$ alkylaminocarbonyloxy groups (e.g. methylaminocarbonyloxy, ethylaminocarbonyloxy, dimethylaminocarbonyloxY, diethylaminocarbonyloxy, etc.), $C_{1-4}$ alkylsulfonylamino groups (e.g. methylsulfonylamino, ethylsulfonylamino, propylsulfonylamino, etc.), $C_{1-4}$ alkoxy-carbonyl groups (e.g. methoxycarbonyl, ethoxycarbonyl, propoxycarbonyl, isobutoxycarbonyl, etc.), carboxyl group, $C_{1-6}$ alkyl-carbonyl groups (e.g. methylcarbonyl, ethylcarbonyl, butylcarbonyl, etc.), C3–7 cycloalkyl-carbonyl (e.g. cyclohexylcarbonyl, etc.), carbamoyl group, mono- or di-$C_{1-4}$ alkyl-carbamoyl groups (e.g. methylcarbamoyl, ethylcarbamoyl, propylcarbamoyl, butylcarbamoyl, diethylcarbamoyl, dibutylcarbamoyl, etc.), alkylsulfonyl groups (e.g. methylsulfonyl, ethylsulfonyl, propylsulfonyl, etc.), cycloalkylsulfonyl (e.g. cyclopentylsulfonyl, cyclohexylsulfonyl, etc.), $C_{1-4}$ alkylenedioxy (e.g. methylenedioxy, etc.) as well as phenyl, naphthyl, mono- or di-phenyl-$C_{1-3}$ alkyl (e.g. benzyl, diphenylmethyl, etc.), phenoxy, benzoyl, phenoxycarbonyl, benzylcarbonyl, phenyl-$C_{1-4}$ alkylcarbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino which may have 1 to 4 substituents selected from the group consisting of $C_{1-4}$ alkyl groups such as methyl, ethyl, propyl, butyl, isopropyl, etc., $C_{1-4}$ alkoxy groups such as methoxy, ethoxy, n-propyloxy, i-propyloxy, n-butyloxy, etc., halogen atoms such as chlorine, bromine, iodine, etc., hydroxyl group, benzyloxy group, amino group, mono- or di-$C_{1-4}$ alkylamino groups as described above, nitro group, $C_{1-6}$ alkyl-carbonyl groups as described above, benzoyl group, etc. The number of substituents which may optionally be substituted on these $C_{6-14}$ aryl groups is suitably about 1 to 5.

As the substituents, which $C_{7-18}$ aralkyl, $C_{6-14}$ aryl-$C_{2-12}$ alkenyl, $C_{6-14}$ aryl-$C_{2-12}$ alkynyl, $C_{3-7}$ cycloalkyl-$C_{1-6}$ alkyl groups may optionally have, use is made of, for example, those similar to the substituents which the above-mentioned $C_{6-14}$ aryl groups may optionally have. The number of the substituents, which these $C_{7-18}$ aralkyl, $C_{6-14}$ aryl-C2–12 alkenyl, $C_{6-14}$ aryl-$C_{2-12}$ alkynyl, $C_{3-7}$ cycloalkyl-$C_{1-6}$ alkyl may optionally have, ranges from 1 to 5.

And, $R^3$ and $R^4$ may form an optionally substituted heterocyclic group, taken together, with the adjacent nitrogen atom. As the "heterocyclic group" of this "optionally substituted heterocyclic group", use is made of, for example, such heterocyclic groups as those containing, other than carbon atoms and one nitrogen atom, optionally 1 to 3 hetero atoms e.g. nitrogen, oxygen or sulfur atom, especially 3- to 13-membered heterocyclic groups. Practically, saturated monocyclic, non-conjugated unsaturated monocyclic, unsaturated monocyclic, polycyclic and bridged heterocyclic groups, for example, are employed.

Examples of the saturated monocyclic heterocyclic group include 5- to 9-membered saturated monocyclic heterocyclic groups such as pyrrolidinyl, piperidinyl, hexamethyleniminyl, heptamethyleniminyl, oxazolidinyl, morpholinyl, thiazolidinyl, thiomorpholinyl, imidazolidinyl, piperazinyl and homopiperazinyl.

Examples of the non-conjugated unsaturated monocyclic or unsaturated monocyclic heterocyclic groups include 5- to 9-membered ones such as pyrrolyl, 1,2-dihydropyridinyl, 1,4-dihydropyridinyl, 1,2,3,6-tetrahydropyridinyl, 2-oxazolidonyl, 2-thiazolidonyl, imidazolyl, pyrazolyl and 1,4,5,6-tetrahydropyrimidinyl.

Examples of the polycyclic heterocyclic group include 2,3-dihydro-1H-indolyl, 1,2,3,4-tetrahydroquinolinyl, 2,3,4,5-tetrahydro-1H-1-benzazepinyl, 2,3-dihydro-1H-isoindolyl, 1,2,3,4-tetrahydroisoquinolinyl, 2,3,4,5-tetrahydro-1H-2-benzazepinyl, 2,3,4,5-tetrahydro-1H-3-benzazepinyl, 1,2,3,4,5,6-hexahydro-1-benzazocinyl, 1,2,3,4,5,6-hexahydro- 2-benzazocinyl, 1,2,3,4,5,6-hexahydro-3-benzazocinyl, 2,3,4,5,6,7-hexahydro-1H-1-benzazonyl, 2,3,4,5,6,7-hexahydro-1H-2-benzazonyl, 2,3,4,5,6,7-hexahydro- 1H-3-benzazonyl, 2,3,4,5,6,7-hexahydro-1H-4-benzazonyl, β-carbolinyl, phenoxazinyl, phenothiazinyl, indolyl, 3H-3-benzazepinyl, 3,4-dihydroquinolinyl, benzimidalyl, 1,4-benzodiazepinyl, etc.

Examples of the bridged heterocyclic group include 1,8-diazaspiro[4.5]decanyl, 2,8-diazaspiro[4.5]decanyl, 1,3,8-triazaspiro[4.5]decanyl, 1,5,9-triazaspiro[ 5.5]undecanyl, 1-oxa-3,9-diazaspiro[ 5.5]undecanyl, 7-azabicyclo[2.2.1]heptanyl, 8-azabicyclo[3.2.11octanyl, 9-azabicyclo[3.3.1]nonanyl, etc.

Preferable examples of "heterocyclic groups" of the "optionally substituted heterocyclic group" optionally formed by $R^3$ and $R^4$, taken together with the adjacent nitrogen atom, include the afore-described saturated monocyclic heterocyclic groups, polycyclic heterocyclic groups or bridged heterocyclic groups. Specifically, pyrrolidinyl, piperidinyl, piperazinyl, morpholinyl, 1,2,3,4-tetrahydroquinolinyl, 1,2,3,4-tetrahydroisoquinolinyl, 2,3,4,5-tetrahydro-1H-1-benzazepinyl, 2,3,4,5-tetrahydro-1H-2-benzazepinyl, 2,3,4,5-tetrahydro-1H-3-benzazepinyl and 1,3,8-triazaspiro[ 4,5]decanyl are preferable, especially, pyrrolidinyl, piperidinyl, piperazinyl, morpholinyl and 1,2,3,4-tetrahydroquinolinyl are often employed.

As the "substituent" of "optionally substituted heterocyclic group", which may optionally be formed by the above-mentioned $R^3$ and $R^4$, taken together with the adjacent nitrogen atom, use is made of 1 to 5 groups, preferably 1 or 2 groups, selected from, for example, optionally substituted hydrocarbon groups referring to the above-mentioned $R^1$, $R^2$, $R^3$, $R^4$, $R^5$ and $R^6$, halogen atoms (e.g. fluorine, chlorine, bromine, iodine, etc.), nitro group, cyano group, hydroxyl group, $C_{1-4}$ alkoxy groups (e.g. methoxy, ethoxy, propyloxy, butyloxy, isopropyloxy, etc.), $C_{1-4}$ alkylthio groups (e.g. methylthio, ethylthio, propylthio, isopropylthio, etc.), aminogroup, mono- or di-$C_{1-4}$ alkylamino groups (e.g. methyl amino, ethylamino, propylamino, dimethylamino, diethylamino, etc.), $C_{1-4}$ alkyl-carbonylamino groups (e.g. acetylamino, propionylamino, butyrylamino, etc.), $C_{1-4}$ alkylsulfonylamino groups (e.g. methylsulfonylamino, ethylsulfonylamino, etc.), $C_{1-4}$ alkoxy-carbonyl groups (e.g. methoxycarbonyl, ethoxycarbonyl, propoxycarbonyl, etc.), carboxyl group, formyl group, $C_{1-6}$ alkyl-carbonyl groups (e.g. methylcarbonyl, ethylcarbonyl, propylcarbonyl, etc.), $C_{1-4}$ alkyl-carbonyloxy groups (e.g. acetyloxy, ethylcarbonyloxy, etc.), ω-oxo-ω-(tetrahydrobenzazepinyl)$C_{1-6}$ alkyl groups (e.g. 1-oxo-1-(tetrahydrobenzazepinyl)methyl, 2-oxo-2-(tetrahydrobenzazepinyl)ethyl, 3-oxo-3-(tetrahydrobenzazepinyl)propyl, etc.), optionally substituted benzoyl groups (herein, as substituents, use is made of 1 to 3 substituents selected from alkyl, for example, methyl, ethyl, etc., halogen, for example, fluorine, chlorine, bromine, etc., $C_{1-4}$ alkoxy, for example, methoxy, ethoxy, etc., mono- or di-$C_{1-4}$ alkylamino, for example, methylamino, dimethylamino, etc., 5- to 7-membered cyclic amino groups, for example, piperidino, morpholino, etc., nitro, hydroxy, etc.;

practical examples of them being benzoyl, 4-fluorobenzoyl, 3,4-dimethoxybenzoyl, etc.), carbamoyl group, mono- or di-$C_{1-4}$ alkylcarbamoyl groups (e.g. methylcarbamoyl, ethylcarbamoyl, etc.), $C_{1-6}$ alkylsulfonyl groups (e.g. methylsulfonyl, ethylsulfonyl, propylsulfonyl, etc.), oxo group, the above-mentioned "heterocyclic group" and saturated heterocyclic groups (e.g. pyridyl, pyridinyl, pyrazinyl, pyrimidinyl, quinolinyl, isoquinolinyl, napthylidinyl, benzothiazolyl, benzoxazolyl, furanyl, thiophenyl, etc.). Among them, formyl, $C_{1-4}$ alkyl-carbonyloxy groups (e.g. acetyloxy, etc.), hydroxyl group, oxo group, pyridinyl group, optionally substituted benzoyl groups (e.g. benzoyl groups optionally substituted with halogen such as fluorine, chlorine, bromine, etc.), ω-oxo-ω-(tetrahydrobenzazepinyl) $C_{1-6}$ alkyl groups (e.g. 1-oxo- 1-(tetrahydrobenzazepinyl)methyl, 2-oxo-2-(tetrahydrobenzazepinyl)ethyl, 3-oxo-3-(tetrahydrobenzazepinyl)propyl, etc.), and optionally substituted hydrocarbon groups referring to the above-mentioned $R^1$, $R^2$, $R^3$, $R^4$, $R^5$, and $R^6$ are preferable. Herein, as optionally substituted hydrocarbon groups referred to in $R^1$, $R^2$, $R^3$, $R^4$, $R^5$ and $R^6$, use is often made of, for example, or straight-chain or branched $C_{1-11}$ alkyl groups, especially straight-chain or branched $C_{1-7}$ alkyl groups (e.g. methyl, ethyl, n-pentyl, n-hexyl, etc.) or $C_{7-18}$ aralkyl groups (e.g. phenyl-$C_{1-12}$ alkyl such as phenylmethyl, phenylethyl, phenylpropyl, phenylhexyl, etc., naphtyl-$C_{1-8}$ alkyl such as α-naphthylmethyl, etc., diphenyl-$C_{1-8}$ alkyl such as diphenylmethyl, etc.), especially $C_{7-10}$ aralkyl groups (e.g. phenylmethyl, phenylethyl, phenylpropyl, etc.), these alkyl and aralkyl groups having optionally halogen (e.g. fluoro, chloro, bromo, etc.), hydroxyl group, $C_{1-4}$ alkylenadioxy (e.g. methylenedioxy, etc.).

As "acyl group" of "optionally substituted acyl group" shown by $R^1$, use is made of, for example, carboxylic acid acyl groups (e.g. formyl, $C_{1-8}$ alkyl-carbonyl or $C_{6-14}$ aryl-carbonyl such as acetyl, propionyl, butyryl, benzoyl, etc.), sulfonic acid acyl groups (e.g. $C_{1-7}$ alkylsulfonyl or $C_{6-14}$ arylsulfonyl such as methanesulfonyl, ethanesulfonyl, propanesulfonyl, benzenesulfonyl, p-toluenesulfonyl, etc.), phosphonic acid acyl groups (e.g. $C_{1-7}$ alkylphosphonyl or $C_{6-14}$ arylphosphonyl such as methanephosphonyl, ethanephosphonyl, propanephosphonyl, benzenephosphonyl, etc.), substituted oxycarbonyl groups (e.g. $C_{1-8}$ alkoxy-carbonyl or $C_{7-18}$ aralkyloxy-carbonyl such as methoxycarbonyl, ethoxycarbonyl, tert-butoxycarbonyl, benzyloxycarbonyl, etc.), heterocycliccarbonyl groups wherein the heterocyclic group is a 5- or 6- membered one containing 1 to 3 hetero atoms selected from N,S and O other than carbon atoms (e.g. pyridylcarbonyl, pyrrolylcarbonyl, quinolylcarbonyl, etc.), carbamoyl group, mono- or di-$C_{1-4}$ alkylcarbamoyl groups (e.g. methylcarbamoyl, ethylcarbamoyl, etc.), etc. Among them, $C_{1-8}$ alkyl-carbonyl or $C_{1-8}$ alkoxycarbonyl mentioned above is preferable.

As the substituent which these acyl groups may have, use is made of 1 to 3, preferably 1 to 2 substituents selected from halogen atoms (e.g. fluorine, chlorine, bromine, iodine, etc.), amino group, mono- or di-$C_{1-6}$ alkylamino groups (e.g. methylamino, ethylamino, propylamino, hexylamino, dimethylamino, diethylamino, etc.) and $C_{1-4}$ alkoxy groups (e.g. methoxy, ethoxy, propoxy, etc.).

The benzene ring shown by ring A may have, besides the groups represented by the formulae

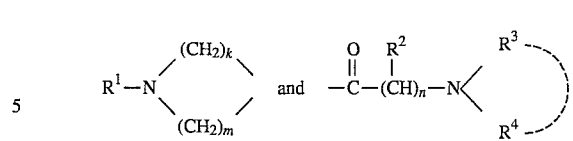

further substituents, and as such substituents, use is made of, for example, those mentioned in reference to $C_{6-14}$ aryl groups of the above-mentioned $R^1$, $R^2$, $R^3$, $R^4$, $R^5$ and $R^6$, the number of them being 1 to 3. Preferable examples of the substituents, which such benzene ring may optionally have, include, among others, halogen such as fluoro, chloro, etc., halogeno-$C_{1-3}$ alkyl such as trifluoromethyl, etc., $C_{1-3}$ alkyl such as methyl, etc. and $C_{1-3}$ alkoxy such as methoxy, etc. Especially, fluoro, for example, is preferable.

The symbol n denotes a whole number of 1 to 10, provided that, in the case of k=0 and m=2, n is more than 1. Preferably, n ranges from 2 to 10, especially from 2 to 8. The symbol k denotes a whole number of 0 to 3, and m denotes a whole number of 1 to 8. In other words, the ring

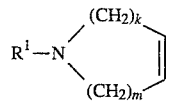

can form a 4- to 14-membered ring.

$X^1$ stands for $R^1$—N< ($R^1$ is of the same meaning as defined above), oxygen atom or sulfur atom.

Preferable examples of $R^1$ include H, straight-chain or branched $C_{1-11}$ hydrocarbon groups which may be substituted with the above-mentioned substituents (e.g. straight-chain or branched $C_{1-11}$ alkyl such as methyl, ethyl, n-propyl, i-propyl, i-butyl, n-butyl etc., straight-chain or branched $C_{2-4}$ alkenyl such as vinyl, allyl, 2-butenyl etc., straight-chain or branched $C_{2-4}$ alkynyl such as propargyl, 2-butynyl etc.), $C_{7-18}$ aralkyl groups which may be substituted with the above-mentioned substituents (e.g. phenylmethyl, (4-methoxyphenyl) methyl, phenylethyl, phenylpropyl, α-naphthylmethyl etc.), formyl group, $C_{1-8}$ alkyl-carbonyl (e.g. acetyl, propionyl, butyryl etc.), $C_{6-14}$ aryl-carbonyl (e.g. benzoyl etc.), $C_{1-8}$ alkoxy-carbonyl (e.g. methoxycarbonyl, ethoxycarbonyl etc.), heterocyclic-carbonyl (e.g. pyridylcarbonyl etc.), carbamoyl, mono- or di-$C_{1-4}$ alkyl-carbamoyl (e.g. methylcarbamoyl, ethylcarbamoyl etc.), etc.; especially H, straight-chain or branched $C_{1-4}$ alkyl groups (e.g. methyl, ethyl, n-propyl, i-propyl, i-butyl, n-butyl etc.), phenyl-$C_{1-3}$ alkyl groups which may be substituted with 1 to 3 substituents selected from $C_{1-4}$ alkyl, halogen, nitro, cyano, hydroxy, $C_{1-4}$ alkoxy and $C_{7-18}$ aralkyloxy (e.g. phenylmethyloxy, (4-methoxyphenyl)methyloxy, phenylethyloxy, phenylpropyloxy etc.), naphthyl-$C_{1-3}$ alkyl (e.g. α-naphtylmethyl, etc.), $C_{1-4}$ alkyl-carbonyl (e.g. acetyl, propionyl, butyryl, etc.), phenyloxycarbonyl, $C_{1-4}$ alkoxy-carbonyl (e.g. methoxycarbonyl, ethoxycarbonyl etc.), etc. More preferable examples of $R^1$ include H, $C_{1-4}$ alkyl (e.g. methyl, ethyl, propyl, i-propyl, i-butyl, etc.), $C_{1-4}$ alkyl-carbonyl (e.g. acetyl, etc.), phenyl-$C_{1-3}$ alkyl which may be substituted with a $C_{1-4}$ alkoxy (e.g. phenylmethyl, (4-methoxyphenyl)methyl, phenylethyl, etc.); more especially, $C_{1-4}$ alkyl group such as i-butyl, etc. or phenyl-$C_{1-3}$ alkyl which may be substituted by a $C_{1-4}$ alkoxy such as methoxy, etc (e.g. phenylmethyl, (4-methoxyphenyl)methyl, phenylethyl).

As $R^2$, $R^5$ and $R^6$, are preferable H, straight-chain or branched $C_{1-3}$ alkyl groups (e.g. methyl, ethyl, n-propyl, i-propyl), phenyl, etc.; especially H is often the case.

Referring to $R^3$ and $R^4$, it is preferable that one of them stands for H or straight-chain or branched $C_{1-4}$ alkyl groups (e.g. methyl, ethyl, n-propyl, i-propyl, n-butyl) and the other stands for straight-chain or branched $C_{1-4}$ alkyl groups, phenyl-$C_{1-3}$ alkyl groups (e.g. phenylmethyl, phenylethyl, phenylpropyl) or naphthyl-$C_{1-3}$ alkyl groups (e.g. α-naphthylmethyl). And, as each of $R^3$ and $R^4$, also preferable are straight-chain or branched $C_{1-4}$ alkyl group which may be substituted with a hydroxy (e.g. methyl, ethyl, 2-hydroxyethyl, etc.) or phenyl-$C_{1-3}$ alkyl group which may be substituted with 1 to 3 halogen atoms such as fluorine, chlorine, bromine, etc. (e.g. phenylmethyl, phenylethyl, 2-chlorophenylmethyl, etc.).

And, such cases as forming heterocyclic rings by $R^3$ and $R^4$, taken together with the adjacent nitrogen atom, are also preferable. Preferable examples include optionally substituted pyrrolidinyl, piperidinyl, piperazinyl, morpholinyl, 1,2,3,4-tetrahydroquinolinyl, 1,2,3,4-tetrahydroisoquinolinyl, 2,3,4,5-tetrahydro-1H- 1-benzazepinyl, 2,3,4,5-tetrahydro-1H-2-benzazepinyl, 2,3,4,5-tetrahydro-1H-3-benzazepinyl, 1,3,8-triazaspiro[ 4.5]decanyl, etc. especially, pyrrolidinyl, piperidinyl, piperazinyl, morpholinyl, 1,2,3,4-tetrahydroisoquinolinyl, etc. Especially preferable examples of the substituents on the heterocyclic groups include formyl group, $C_{1-4}$ alkyl-carbonyl groups (e.g. acetyl, etc.), hydroxyl group, oxo group, pyridyl group, an optionally substituted benzoyl group (e.g. benzoyl group which may be substituted with 1 to 3 halogen atoms such as fluorine, chlorine, bromine, etc.), optionally substituted straight-chain or branched $C_{1-7}$ alkyl groups (e.g. methyl, ethyl, n-propyl, i-propyl, n-butyl, tert-butyl, n-pentyl, n-hexyl, which may be substituted with 1 to 3 substituents such as hydroxy group, 5- or 6-membered heterocyclic group containing i to 3 hetero atoms of N, S and/or O other than carbon atoms such as pyridyl, furyl, thiazol-4-yl, 2-methyl-thiazol-4-yl, etc.), an optionally substituted phenyl group (e.g. phenyl group which may be substituted with 1 to 3 substituents such as halogen (e.g. fluorine, chlorine, bromine, etc.), hydroxy group, $C_{1-4}$ alkylene-dioxy (e.g. methylenedioxy, etc.), etc.), optionally substituted $C_{7-18}$ aralkyl groups (e.g. phenyl-$C_{1-12}$ alkyl such as phenylmethyl, phenylethyl, phenylpropyl, phenylhexyl, etc., α-naphthylmethyl, diphenyl-$C_{1-8}$ alkyl such as diphenylmethyl, etc., which may be substituted with 1 to 3 substituents such as halogen (e.g. fluorine, chlorine, bromine, etc.), hydroxy group, $C_{1-4}$ alkylenedioxy (e.g. methylenedioxy, etc.), etc.), ω-oxo-ω-(tetrahydrobenzazepinyl) $C_{1-6}$ alkyl (e.g. 1-oxo-1-(tetrahydrobenzazepinyl) methyl, 2-oxo-2-(tetrahdyrobenzazepinyl) ethyl, 3-oxo-3-(tetrahydrobenzazepinyl) propyl, etc.), the number of them being 1 or 2, preferably 1. As $R^3$ and $R^4$, most preferable examples are such cases as forming 4-(phenylmethyl)-piperazin- 1-yl or 4-[(2-methylthiazol-4-yl)methyl] -piperazin-1-yl, taken together with the adjacent nitrogen atom.

Preferable benzene ring shown by ring A is unsubstituted one.

Referring to k and m, the case where k+m denotes a whole number of 2 to 6 is preferable, namely the case where the moiety

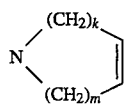

forms a 5- to 9-membered ring. Further, referring to the combination of k and m, it is preferable that, when k is 0, m is 2, 3, 4 or 5; when k is 1, m is 1, 2 or 3; and when k is 2, m is 2. More specifically, preferable examples of the N-containing condensed heterocyclic ring represented by the formula:

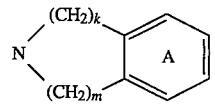

include 2,3-dihydro-1H-indole, 1,2,3,4-tetrahydroquinoline, 2,3,4,5-tetrahydro-1H-1-benzazepine, 2,3-dihydro-1H-isoindole, 1,2,3,4-tetrahydroisoquinoline, 2,3,4,5-tetrahydro-1H-2-benzazepine, 2,3,4,5-tetrahydro-1H- 3-benzazepine, 1,2,3,4,5,6-hexahydro-1-benzazocine , 1,2,3,4,5,6-hexahydro- 2-benzazocine, 1,2,3,4,5, 6-hexahydro-3-benzazocine, 2,3,4,5,6,7-hexahydro- 1H-1-benzazonine, 2,3,4,5,6,7-hexahydro-1H-2-benzazonine, 2,3,4,5,6,7-hexahydro- 1H-3-benzazonine, 2,3,4,5,6,7-hexahydro-1H-4-benzazonine, etc., especially, 2,3,4,5-tetrahydro-1H-3-benzazepine, 2,3,4,5-tetrahydro-1H- 2-benzazepine, 2,3-dihydro- 1H-indole, etc.

Preferable ones of the condensed heterocyclic ring moiety in the above formulae shown by the formula:

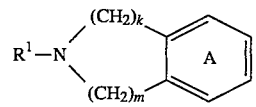

include the N-containing condensed heterocyclic rings shown by the following formulae:

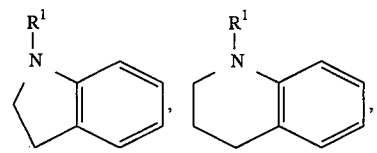

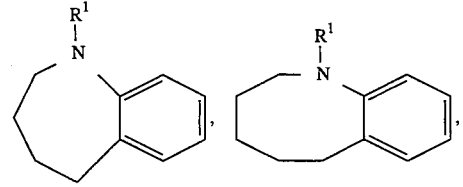

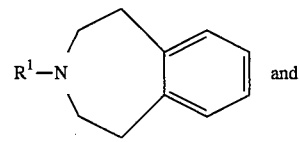

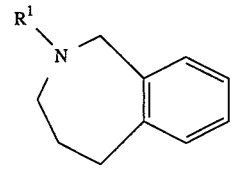

wherein $R^1$ is of the same meaning as defined above. In the above formulae, preferable examples of $R^1$ include H, $C_{1-4}$ alkyl groups (e.g. methyl, ethyl, n-propyl, i-propyl etc.), phenyl-$C_{1-3}$ alkyl groups which may be substituted by a $C_{-4}$ alkoxy (e.g. phenylmethyl, (4-methoxyphenyl)methyl, phenylethyl, phenylpropyl, etc.) or $C_{1-3}$ alkyl-carbonyl (e.g. acetyl, etc.), etc.

Referring to n, when the group of the formula:

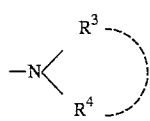

does not form a heterocyclic group, it is preferably a whole number of 3 to 8, and, when the group forms a heterocyclic group, it is preferably a whole number of 2 to 5.

As $X^1$, $R^1$—N< is preferable.

More specifically, the following compounds and salts thereof belonging to the compounds of the formula (I) or salts thereof are preferable.

TABLE 1

| No. | $R^1$ | k | m | n | $Z^1$ | $Z^2$ | $Z^3$ | $N(R^3)(R^4)$ |
|-----|-------|---|---|---|-------|-------|-------|---------------|
| 1 | H | 0 | 2 | 2 | H | H | H | N($C_2H_5$)(H) |
| 2 | H | 0 | 2 | 2 | H | H | H | N($C_2H_5$)($CH_2Ph$) |
| 3 | H | 0 | 2 | 3 | H | H | H | N($C_2H_5$)($CH_2Ph$) |
| 4 | H | 0 | 2 | 4 | H | H | H | N($C_2H_5$)($CH_2Ph$) |
| 5 | H | 0 | 2 | 5 | H | H | H | N($C_2H_5$)($CH_2Ph$) |
| 6 | H | 0 | 2 | 6 | H | H | H | N($C_2H_5$)($CH_2Ph$) |
| 7 | H | 0 | 2 | 7 | H | H | H | N($C_2H_5$)($CH_2Ph$) |
| 8 | H | 0 | 2 | 8 | H | H | H | N($C_2H_5$)($CH_2Ph$) |

TABLE 1-continued

![Structure: R¹-N(CH₂)ₖ/(CH₂)ₘ-benzene(Z¹,Z²,Z³)-C(=O)-(CH₂)ₙ-N(R³)(R⁴), with alternative cyclic NR³R⁴]

| No. | R¹ | k | m | n | Z¹ | Z² | Z³ | NR³R⁴ |
|-----|------|---|---|---|-----|------|-----|--------|
| 9 | Ac | 0 | 2 | 6 | H | H | H | N(C₂H₅)(CH₂Ph) |
| 10 | COPh | 0 | 2 | 6 | H | H | H | N(C₂H₅)(CH₂Ph) |
| 11 | CH₃ | 0 | 2 | 6 | Cl | H | H | N(C₂H₅)(CH₂Ph) |
| 12 | CH₂Ph | 0 | 2 | 6 | H | OH | H | N(C₂H₅)(CH₂Ph) |
| 13 | Ph | 0 | 2 | 6 | H | OCH₃ | H | N(C₂H₅)(CH₂Ph) |
| 14 | H | 0 | 2 | 6 | F | H | CH₃ | N(C₂H₅)(CH₂Ph) |
| 15 | CH₂Ph | 0 | 2 | 6 | NO₂ | H | H | N(C₂H₅)(CH₂Ph) |
| 16 | H | 0 | 2 | 6 | H | H | H | N(C₂H₅)(CH₂-C₆H₄-OH) |

TABLE 2

| No. | R¹ | k | m | n | Z¹ | Z² | Z³ | $\begin{array}{c}R^3\\ \diagdown\\ N\\ \diagup\\ R^4\end{array}$ |
|---|---|---|---|---|---|---|---|---|
| 17 | H | 0 | 2 | 6 | H | H | H | –N(C₂H₅)(CH₂-(3-F-C₆H₄)) |
| 18 | H | 0 | 2 | 6 | H | H | H | –N(C₂H₅)(CH₂-(2-CH₃O-C₆H₄)) |
| 19 | Ac | 0 | 2 | 6 | H | H | H | –N(C₂H₅)(CH₂-(4-N(CH₃)₂-C₆H₄)) |
| 20 | H | 0 | 2 | 6 | H | H | H | –N(C₂H₅)(CH₂-(1-naphthyl)) |
| 21 | H | 0 | 3 | 1 | H | H | H | –N(CH₃)(CH₂Ph) |
| 22 | H | 0 | 3 | 2 | H | H | H | –N(C₂H₅)(CH₂Ph) |
| 23 | H | 0 | 3 | 3 | H | H | H | –N(C₂H₅)(CH₂Ph) |
| 24 | H | 0 | 3 | 4 | H | H | H | –N(C₂H₅)(CH₂Ph) |
| 25 | H | 0 | 3 | 5 | H | H | H | –N(C₂H₅)(CH₂Ph) |
| 26 | H | 0 | 3 | 6 | H | H | H | –N(C₂H₅)(CH₂Ph) |

TABLE 2-continued

| No. | R¹ | k | m | n | Z¹ | Z² | Z³ | NR³R⁴ |
|---|---|---|---|---|---|---|---|---|
| 27 | H | 0 | 3 | 7 | H | H | H | N(C₂H₅)(CH₂Ph) |
| 28 | H | 0 | 3 | 8 | H | H | H | N(C₂H₅)(CH₂Ph) |
| 29 | Ac | 0 | 3 | 6 | H | H | H | N(C₂H₅)(CH₂Ph) |
| 30 | COPh | 0 | 3 | 6 | H | H | H | N(C₂H₅)(CH₂Ph) |
| 31 | CH₃ | 0 | 3 | 6 | Cl | H | H | N(C₂H₅)(CH₂Ph) |
| 32 | CH₂Ph | 0 | 3 | 6 | H | OH | H | N(C₂H₅)(CH₂Ph) |
| 33 | Ph | 0 | 3 | 6 | H | OCH₃ | H | N(C₂H₅)(CH₂Ph) |
| 34 | H | 0 | 3 | 6 | F | H | CH₃ | N(C₂H₅)(CH₂Ph) |

TABLE 3

| No. | R¹ | k | m | n | Z¹ | Z² | Z³ | NR³R⁴ |
|---|---|---|---|---|---|---|---|---|
| 35 | CH₂Ph | 0 | 3 | 6 | NO₂ | H | H | N(C₂H₅)(CH₂Ph) |
| 36 | H | 0 | 3 | 6 | H | H | H | N(CH₃)(CH₂-(2-CH₃O-C₆H₄)) |

TABLE 3-continued

| No. | R¹ | k | m | n | Z¹ | Z² | Z³ | NR³R⁴ |
|---|---|---|---|---|---|---|---|---|
| 37 | H | 0 | 3 | 6 | H | H | H | N(C₂H₅)(CH₂-C₆H₄-4-Cl) |
| 38 | H | 0 | 3 | 6 | H | H | H | N(C₂H₅)(CH₂-C₆H₄-3-F) |
| 39 | Ac | 0 | 3 | 6 | H | H | H | N(C₂H₅)(CH₂-C₆H₄-4-NO₂) |
| 40 | H | 0 | 3 | 6 | H | H | H | N(C₂H₅)(CH₂-C₆H₄-4-CH₃) |
| 41 | H | 0 | 4 | 5 | H | H | OH | N(C₂H₅)(CH₂Ph) |
| 42 | H | 0 | 4 | 6 | H | H | H | N(C₂H₅)(CH₂Ph) |
| 43 | CH₂Ph | 0 | 4 | 6 | H | H | H | N(C₂H₅)(CH₂Ph) |
| 44 | CH₃ | 0 | 4 | 6 | F | H | H | N(CH(CH₃)₂)(CH₂Ph) |
| 45 | Ac | 0 | 4 | 7 | H | H | CH₃ | N(C₂H₅)(CH₂Ph) |
| 46 | H | 0 | 5 | 5 | H | H | H | N(C₂H₅)(CH₂Ph) |
| 47 | H | 0 | 5 | 6 | Cl | H | H | N(C₂H₅)(CH₂Ph) |

TABLE 3-continued

| No. | $R^1$ | k | m | n | $Z^1$ | $Z^2$ | $Z^3$ | $N(R^3)(R^4)$ |
|---|---|---|---|---|---|---|---|---|
| 48 | H | 0 | 5 | 6 | H | OCH$_3$ | H | N(C$_2$H$_5$)(CH$_2$Ph) |
| 49 | Ac | 0 | 5 | 6 | H | H | H | N(CH$_2$CH$_2$OH)(CH$_2$Ph) |
| 50 | COPh | 0 | 5 | 7 | H | H | H | N(C$_2$H$_5$)(CH$_2$Ph) |
| 51 | C$_2$H$_5$ | 1 | 1 | 6 | Cl | H | H | N(C$_2$H$_5$)(CH$_2$Ph) |
| 52 | CH$_2$Ph | 1 | 1 | 6 | H | OH | H | N(C$_2$H$_5$)(CH$_2$Ph) |

TABLE 4

| No. | $R^1$ | k | m | n | $Z^1$ | $Z^2$ | $Z^3$ | $N(R^3)(R^4)$ |
|---|---|---|---|---|---|---|---|---|
| 53 | Ph | 1 | 2 | 6 | H | OCH$_3$ | H | N(C$_2$H$_5$)(CH$_2$-2-HOC$_6$H$_4$) |
| 54 | H | 1 | 2 | 6 | F | H | CH$_3$ | N(C$_2$H$_5$)(CH$_2$-4-CH$_3$SC$_6$H$_4$) |
| 55 | CH$_2$Ph | 1 | 2 | 6 | NO$_2$ | H | H | N(C$_2$H$_5$)(CH$_2$-4-C$_2$H$_5$C$_6$H$_4$) |
| 56 | H | 1 | 2 | 6 | H | H | H | N(C$_2$H$_5$)(CH$_2$-2-CH$_3$OC$_6$H$_4$) |

TABLE 4-continued
| No. | R¹ | k | m | n | Z¹ | Z² | Z³ | $\begin{array}{c}R^3\\N\\R^4\end{array}$ |
|---|---|---|---|---|---|---|---|---|
| 57 | H | 1 | 2 | 6 | H | H | H | 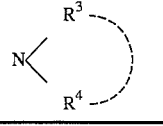 |
| 58 | H | 1 | 3 | 6 | F | H | H | 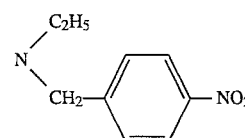 |
| 59 | Ac | 1 | 3 | 6 | H | H | H | 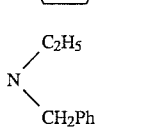 |
| 60 | CH₂Ph | 1 | 3 | 6 | H | H | H | 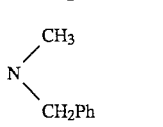 |
| 61 | H | 2 | 2 | 5 | H | H | H | 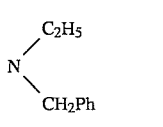 |
| 62 | H | 2 | 2 | 6 | H | H | H | 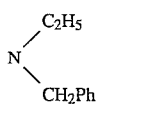 |
| 63 | Ac | 2 | 2 | 6 | H | H | H | 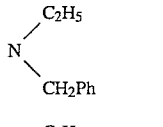 |
| 64 | CH₃ | 2 | 2 | 6 | H | H | H | 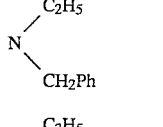 |
| 65 | COPh | 2 | 2 | 6 | H | H | H | 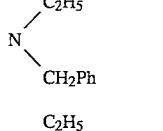 |
| 66 | CO₂CH₃ | 2 | 2 | 7 | H | H | H | 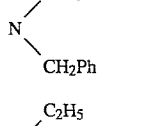 |
| 67 | Ac | 2 | 2 | 1 | H | H | H | 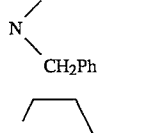 |
| 68 | CH₂Ph | 2 | 2 | 6 | H | H | H | 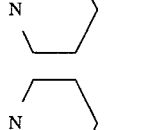 |
| 69 | CH₂Ph | 2 | 2 | 7 | H | H | H | 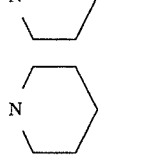 |

TABLE 4-continued
| No. | R¹ | k | m | n | Z¹ | Z² | Z³ | NR³R⁴ |
|---|---|---|---|---|---|---|---|---|
| 70 | CH₂Ph | 2 | 2 | 8 | H | H | H | 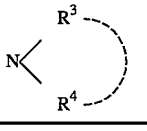 |
TABLE 5
| No. | R¹ | k | m | n | Z¹ | Z² | Z³ | NR³R⁴ |
|---|---|---|---|---|---|---|---|---|
| 71 | CH₂Ph | 2 | 2 | 2 | H | H | H |  |
| 72 | CH₂Ph | 2 | 2 | 2 | H | H | H | 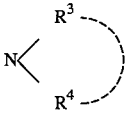 |
| 73 | CH₂Ph | 2 | 2 | 2 | OCH₃ | OCH₃ | H |  |
| 74 | CH₂Ph | 2 | 2 | 2 | F | H | CH₃ | NH₂ |
| 75 | CH₂Ph | 2 | 2 | 2 | H | H | H |  |
| 76 | CH₂Ph | 2 | 2 | 2 | H | H | CH₃ | 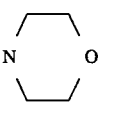 |
| 77 | CH₂Ph | 2 | 2 | 2 | NO₂ | OH | H |  |
| 78 | CH₂Ph | 2 | 2 | 2 | H | H | H | 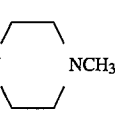 |
| 79 | CH₂Ph | 2 | 2 | 2 | H | H | H | 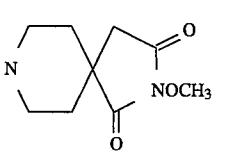 |
| 80 | 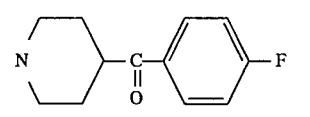 | 2 | 2 | 2 | OCH₃ | H | H | 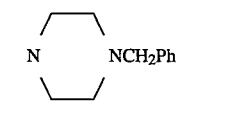 |

TABLE 5-continued
| No. | $R^1$ | k | m | n | $Z^1$ | $Z^2$ | $Z^3$ | $\begin{array}{c}R^3 \\ N \\ R^4\end{array}$ |
|---|---|---|---|---|---|---|---|---|
| 81 | Ac | 2 | 2 | 3 | H | H | H | 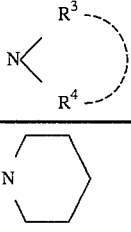 |
| 82 | CH$_2$Ph | 2 | 2 | 3 | H | H | H |  |
| 83 | CH$_2$Ph | 2 | 2 | 3 | H | H | H | 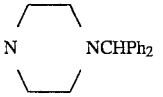 |
| 84 | CH$_2$Ph | 2 | 2 | 3 | CH$_3$ | H | H | 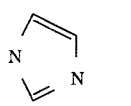 |
| 85 | CH$_2$Ph | 2 | 2 | 3 | Cl | H | H | 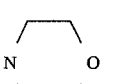 |
| 86 | 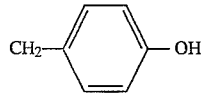 | 2 | 2 | 3 | H | H | H | 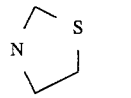 |
| 87 | 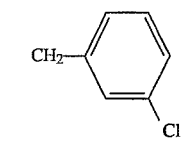 | 2 | 2 | 3 | H | H | H | 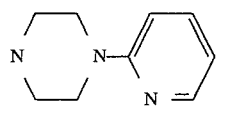 |
| 88 | 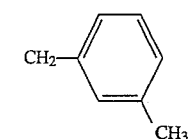 | 2 | 2 | 3 | F | H | H | 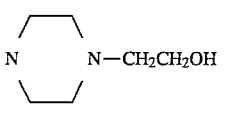 |
| 89 | 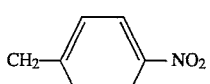 | 2 | 2 | 3 | H | H | H | 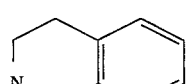 |
| 90 | 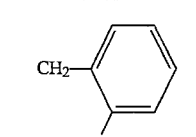 | 2 | 2 | 3 | OCH$_3$ | H | H | 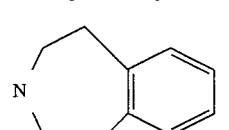 |

TABLE 6
| No. | R¹ | k | m | n | Z¹ | Z² | Z³ | NR³R⁴ |
|---|---|---|---|---|---|---|---|---|
| 91 | CH₂Ph | 2 | 2 | 4 | H | H | H | 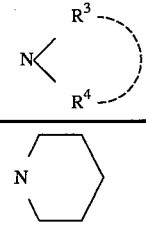 |
| 92 | CH₂Ph | 2 | 2 | 4 | CH₃ | OH | H | 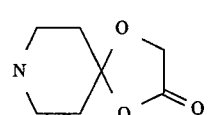 |
| 93 | CH₂Ph | 2 | 2 | 4 | OCH₃ | H | H | 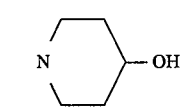 |
| 94 | CH₂Ph | 2 | 2 | 4 | F | H | CH₃ | 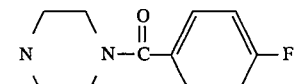 |
| 95 | CH₂Ph | 2 | 2 | 4 | NO₂ | H | H | 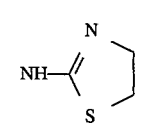 |
| 96 | CH₂Ph | 2 | 2 | 5 | H | H | H | 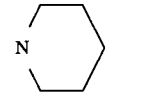 |
| 97 | CH₂Ph | 2 | 2 | 5 | H | H | H | 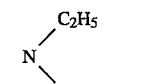 |
| 98 | CH₂Ph | 2 | 2 | 5 | CH₃ | H | H | 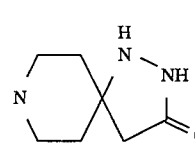 |
| 99 | CH₂Ph | 2 | 2 | 5 | Cl | H | OH | 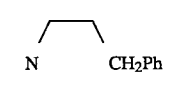 |
| 100 | CH₂Ph | 2 | 2 | 5 | F | H | H | 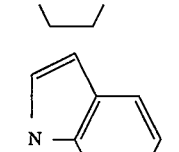 |

TABLE 7

| No. | R¹ | k | m | n | Z¹ | Z² | Z³ | $N(R^3)(R^4)$ |
|---|---|---|---|---|---|---|---|---|
| 101 | H | 0 | 3 | 1 | H | H | H | N(C₂H₅)(CH₂Ph) |
| 102 | H | 0 | 3 | 2 | H | H | H | N(C₂H₅)(CH₂Ph) |
| 103 | H | 0 | 3 | 3 | H | H | H | N(C₂H₅)(CH₂Ph) |
| 104 | H | 0 | 3 | 4 | H | H | H | N(C₂H₅)(CH₂Ph) |
| 105 | H | 0 | 3 | 5 | H | H | H | N(C₂H₅)(CH₂Ph) |

TABLE 7-continued

| No. | R¹ | k | m | n | Z¹ | Z² | Z³ | $N(R^3)(R^4)$ |
|---|---|---|---|---|---|---|---|---|
| 106 | H | 0 | 3 | 6 | H | H | H | N(C₂H₅)(CH₂Ph) |
| 107 | H | 0 | 3 | 7 | H | H | H | N(C₂H₅)(CH₂Ph) |
| 108 | H | 0 | 3 | 8 | H | H | H | N(C₂H₅)(CH₂Ph) |
| 109 | Ac | 0 | 3 | 6 | H | H | H | N(C₂H₅)(CH₂Ph) |
| 110 | COPh | 0 | 3 | 6 | H | H | H | N(C₂H₅)(CH₂Ph) |

TABLE 8

| No. | R¹ | k | m | n | Z¹ | Z² | Z³ | $N(R^3)(R^4)$ |
|---|---|---|---|---|---|---|---|---|
| 111 | CH₃ | 0 | 3 | 6 | Cl | H | H | N(C₂H₅)(CH₂Ph) |
| 112 | CH₂Ph | 0 | 3 | 6 | H | OH | H | N(C₂H₅)(CH₂Ph) |
| 113 | Ph | 0 | 3 | 6 | H | OCH₃ | H | N(C₂H₅)(CH₂Ph) |
| 114 | H | 0 | 3 | 6 | F | H | CH₃ | N(C₂H₅)(CH₂Ph) |

TABLE 8-continued

| No. | R$^1$ | k | m | n | Z$^1$ | Z$^2$ | Z$^3$ | N(R$^3$)(R$^4$) |
|---|---|---|---|---|---|---|---|---|
| 115 | CH$_2$Ph | 0 | 3 | 6 | H | H | NO$_2$ | N(C$_2$H$_5$)(CH$_2$-2-CH$_3$O-C$_6$H$_4$) |
| 116 | H | 0 | 3 | 6 | H | H | H | N(C$_2$H$_5$)(CH$_2$-4-CH$_3$-C$_6$H$_4$) |
| 117 | H | 0 | 3 | 6 | H | H | H | N(C$_2$H$_5$)(CH$_2$-4-Cl-C$_6$H$_4$) |
| 118 | H | 0 | 3 | 6 | H | H | H | N(C$_2$H$_5$)(CH$_2$-3-F-C$_6$H$_4$) |
| 119 | Ac | 0 | 3 | 6 | H | H | H | N(C$_2$H$_5$)(CH$_2$-2-HO-C$_6$H$_4$) |
| 120 | H | 0 | 3 | 6 | H | H | H | N(C$_2$H$_5$)(CH$_2$-1-naphthyl) |
| 121 | H | 0 | 4 | 1 | H | H | H | N(CH$_3$)(CH$_2$Ph) |
| 122 | H | 0 | 4 | 2 | H | H | H | N(C$_2$H$_5$)(CH$_2$Ph) |
| 123 | H | 0 | 4 | 3 | H | H | H | N(C$_2$H$_5$)(CH$_2$Ph) |

TABLE 8-continued

| No. | R¹ | k | m | n | Z¹ | Z² | Z³ | N(R³)(R⁴) |
|---|---|---|---|---|---|---|---|---|
| 124 | H | 0 | 4 | 4 | H | H | H | N(C$_2$H$_5$)(CH$_2$Ph) |
| 125 | H | 0 | 4 | 5 | H | H | H | N(C$_2$H$_5$)(CH$_2$Ph) |
| 126 | H | 0 | 4 | 6 | H | H | H | N(C$_2$H$_5$)(CH$_2$Ph) |
| 127 | H | 0 | 4 | 7 | H | H | H | N(C$_2$H$_5$)(CH$_2$Ph) |
| 128 | H | 0 | 4 | 8 | H | H | H | N(C$_2$H$_5$)(CH$_2$Ph) |
| 129 | Ac | 0 | 4 | 6 | H | H | H | N(C$_2$H$_5$)(CH$_2$Ph) |

TABLE 9

| No. | R¹ | k | m | n | Z¹ | Z² | Z³ | N(R³)(R⁴) |
|---|---|---|---|---|---|---|---|---|
| 130 | COPh | 0 | 4 | 6 | H | H | H | N(C$_2$H$_5$)(CH$_2$Ph) |
| 131 | CH$_3$ | 0 | 4 | 6 | Cl | H | H | N(C$_2$H$_5$)(CH$_2$Ph) |
| 132 | CH$_2$Ph | 0 | 4 | 6 | H | OH | H | N(C$_2$H$_5$)(CH$_2$Ph) |
| 133 | Ph | 0 | 4 | 6 | H | OCH$_3$ | H | N(C$_2$H$_5$)(CH$_2$Ph) |
| 134 | H | 0 | 4 | 6 | F | H | CH$_3$ | N(C$_2$H$_5$)(CH$_2$Ph) |

TABLE 9-continued

| No. | R¹ | k | m | n | Z¹ | Z² | Z³ | $\begin{array}{c}R^3\\N\\R^4\end{array}$ |
|---|---|---|---|---|---|---|---|---|
| 135 | CH₂Ph | 0 | 4 | 6 | NO₂ | H | H | N(C₂H₅)(CH₂Ph) |
| 136 | H | 0 | 4 | 6 | H | H | H | N(C₂H₅)(CH₂Ph) |
| 137 | H | 0 | 4 | 6 | H | H | H | N(C₂H₅)(CH₂-2-CH₃O-C₆H₄) |
| 138 | CO₂Ph | 0 | 4 | 6 | H | H | H | N(C₂H₅)(CH₂-4-F-C₆H₄) |
| 139 | Ac | 0 | 4 | 6 | H | H | H | N(C₂H₅)(CH₂-4-Cl-C₆H₄) |
| 140 | CONHCH₃ | 0 | 4 | 6 | H | H | H | N(C₂H₅)(CH₂-4-OCH₃-C₆H₄) |
| 141 | H | 0 | 5 | 4 | H | H | H | N(C₂H₅)(CH₂Ph) |
| 142 | H | 0 | 5 | 5 | H | H | H | N(C₂H₅)(CH₂Ph) |
| 143 | H | 0 | 5 | 6 | H | H | H | N(C₂H₅)(CH₂Ph) |
| 144 | H | 0 | 5 | 6 | H | H | H | N(C₂H₅)(CH₂-4-OH-C₆H₄) |
| 145 | CH₃ | 0 | 5 | 6 | H | OH | H | N(C₂H₅)(CH₂Ph) |

TABLE 9-continued

| No. | R¹ | k | m | n | Z¹ | Z² | Z³ | $\begin{array}{c}R^3 \\ N< \\ R^4\end{array}$ |
|---|---|---|---|---|---|---|---|---|
| 146 | CH₂Ph | 0 | 5 | 6 | H | OCH₃ | H | N(C₂H₅)(CH₂Ph) |
| 147 | Ac | 0 | 5 | 6 | H | H | Cl | N(C₂H₅)(CH₂Ph) |
| 148 | CONHCH₃ | 0 | 5 | 6 | F | H | H | N(C₂H₅)(CH₂Ph) |
| 149 | H | 0 | 5 | 7 | H | OCH₃ | OCH₃ | N(C₂H₅)(CH₂Ph) |

TABLE 10

| No. | R¹ | k | m | n | Z¹ | Z² | Z³ | $\begin{array}{c}R^3 \\ N< \\ R^4\end{array}$ |
|---|---|---|---|---|---|---|---|---|
| 150 | COPh | 0 | 5 | 8 | H | H | H | N(CH₂CH₂OH)(CH₂Ph) |
| 151 | H | 0 | 2 | 3 | Cl | H | H | N(CH₃)(CH₂Ph) |
| 152 | CH₂Ph | 0 | 2 | 4 | H | OH | H | N(C₂H₅)(CH₂Ph) |
| 153 | Ph | 0 | 2 | 6 | H | OCH₃ | H | N(CH₂CH₂OH)(CH₂Ph) |
| 154 | H | 0 | 2 | 6 | F | H | CH₃ | N(C₂H₅)(CH₂Ph) |
| 155 | CH₂Ph | 0 | 2 | 6 | H | H | H | N(CH₃)(CH₂Ph) |
| 156 | CH₂Ph | 1 | 2 | 2 | H | H | H | N(C₂H₅)(CH₂Ph) |

TABLE 10-continued

| No. | R¹ | k | m | n | Z¹ | Z² | Z³ | N(R³R⁴) |
|---|---|---|---|---|---|---|---|---|
| 157 | CH₂Ph | 1 | 2 | 3 | H | H | H | N(C₂H₅)(CH₂Ph) |
| 158 | CH₂Ph | 1 | 2 | 4 | H | OH | H | N(C₂H₅)(CH₂Ph) |
| 159 | Ac | 1 | 2 | 5 | H | OH₃ | H | N(C₂H₅)(CH₂Ph) |
| 160 | H | 1 | 2 | 6 | H | H | H | N(C₂H₅)(CH₂Ph) |
| 161 | H | 1 | 3 | 2 | H | H | H | N(CH₃)(CH₂Ph) |
| 162 | H | 1 | 3 | 2 | H | H | H | N(C₂H₅)(CH₂Ph) |

TABLE 11

| No. | R¹ | k | m | n | Z¹ | Z² | Z³ | N(R³R⁴) |
|---|---|---|---|---|---|---|---|---|
| 163 | H | 1 | 3 | 3 | H | H | H | N(C₂H₅)(CH₂Ph) |
| 164 | H | 1 | 3 | 4 | H | H | H | N(C₂H₅)(CH₂Ph) |
| 165 | H | 1 | 3 | 5 | H | H | H | N(C₂H₅)(CH₂Ph) |
| 166 | H | 1 | 3 | 6 | H | H | H | N(C₂H₅)(CH₂Ph) |
| 167 | H | 1 | 3 | 7 | H | H | H | N(C₂H₅)(CH₂Ph) |

TABLE 11-continued

| No. | R¹ | k | m | n | Z¹ | Z² | Z³ | $\begin{array}{c}R^3\\N\\R^4\end{array}$ |
|---|---|---|---|---|---|---|---|---|
| 168 | H | 1 | 3 | 8 | H | H | H | N(C₂H₅)(CH₂Ph) |
| 169 | Ac | 1 | 3 | 6 | H | H | H | N(C₂H₅)(CH₂Ph) |
| 170 | COPh | 1 | 3 | 6 | H | H | H | N(C₂H₅)(CH₂Ph) |
| 171 | CH₃ | 1 | 3 | 6 | Cl | H | H | N(C₂H₅)(CH₂Ph) |
| 172 | CO₂CH₃ | 1 | 3 | 6 | H | OH | H | N(C₂H₅)(CH₂Ph) |
| 173 | Ph | 1 | 3 | 6 | H | OCH₃ | H | N(C₂H₅)(CH₂Ph) |
| 174 | H | 1 | 3 | 4 | F | H | CH₃ | N(C₂H₅)(CH₂Ph) |
| 175 | C₂H₅ | 1 | 3 | 5 | NO₂ | H | H | N(C₂H₅)(CH₂-C₆H₄-4-F) |
| 176 | H | 1 | 3 | 6 | H | H | CH₃ | N(C₂H₅)(CH₂-C₆H₄-2-OCH₃) |
| 177 | H | 1 | 3 | 6 | H | H | OCH₃ | N(C₂H₅)(CH₂-C₆H₄-4-NO₂) |
| 178 | H | 1 | 3 | 6 | H | H | H | N(C₂H₅)(CH₂-C₆H₄-4-NHAc) |

TABLE 11-continued

| No. | $R^1$ | k | m | n | $Z^1$ | $Z^2$ | $Z^3$ | $N<\genfrac{}{}{0pt}{}{R^3}{R^4}$ |
|---|---|---|---|---|---|---|---|---|
| 179 | Ac | 1 | 3 | 6 | H | H | H | N(C$_2$H$_5$)(CH$_2$-C$_6$H$_4$-4-SCH$_3$) |
| 180 | H | 1 | 3 | 6 | H | H | H | N(C$_2$H$_5$)(CH$_2$-C$_6$H$_4$-4-CO$_2$CH$_3$) |
| 181 | CH$_2$Ph | 1 | 3 | 5 | H | H | H | piperidin-1-yl |

TABLE 12

| No. | $R^1$ | k | m | n | $Z^1$ | $Z^2$ | $Z^3$ | $N<\genfrac{}{}{0pt}{}{R^3}{R^4}$ |
|---|---|---|---|---|---|---|---|---|
| 182 | CH$_2$Ph | 1 | 3 | 5 | H | H | H | morpholin-4-yl |
| 183 | CH$_2$Ph | 1 | 3 | 6 | H | H | H | 4-methylpiperazin-1-yl |
| 184 | CH$_2$Ph | 1 | 3 | 7 | H | H | H | 4-benzylpiperazin-1-yl |
| 185 | CH$_2$Ph | 1 | 3 | 8 | H | H | H | 4-(diphenylmethyl)piperazin-1-yl |
| 186 | CH$_2$Ph | 1 | 3 | 2 | H | H | H | piperidin-1-yl |
| 187 | CH$_2$Ph | 1 | 3 | 2 | H | H | H | pyrrolidin-1-yl |
| 188 | CH$_2$Ph | 1 | 3 | 2 | H | OCH$_3$ | OCH$_3$ | 4-(pyrimidin-2-yl)piperazin-1-yl |

TABLE 12-continued
| No. | R¹ | k | m | n | Z¹ | Z² | Z³ | NR³R⁴ |
|---|---|---|---|---|---|---|---|---|
| 189 | CH₂-C₆H₄-F (m) | 1 | 3 | 2 | H | H | H | 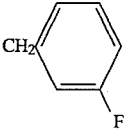 |
| 190 | CH₂-C₆H₄-CH₃ (m) | 1 | 3 | 2 | H | H | H | 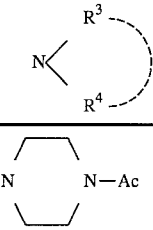 |
| 191 | CH₂Ph | 1 | 3 | 3 | H | H | H | 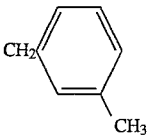 |
| 192 | CH₂Ph | 1 | 3 | 3 | H | H | H | 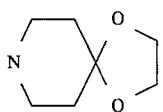 |
| 193 | CH₂Ph | 1 | 3 | 3 | H | OCH₃ | H |  |
| 194 | CH₂-C₆H₄-CH₃ (p) | 1 | 3 | 3 | H | H | CH₃ | 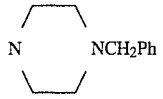 |
| 195 | CH₂-C₆H₄-OCH₃ (o) | 1 | 3 | 3 | H | H | NO₂ |  |
| 196 | CH₂Ph | 1 | 3 | 4 | H | H | H | 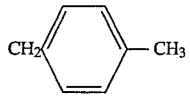 |
| 197 | CH₂Ph | 1 | 3 | 4 | H | H | H | 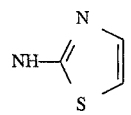 |
| 198 | CH₂Ph | 1 | 3 | 4 | H | H | H | 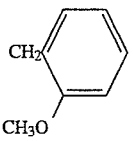 |
| 199 | CH₂-C₆H₄-NO₂ (p) | 1 | 3 | 4 | H | CH₃ | CH₃ | 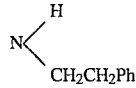 |
| 200 | CH₂-C₆H₄-OCH₃ (p) | 1 | 3 | 4 | H | H | OCH₃ |  |

TABLE 13
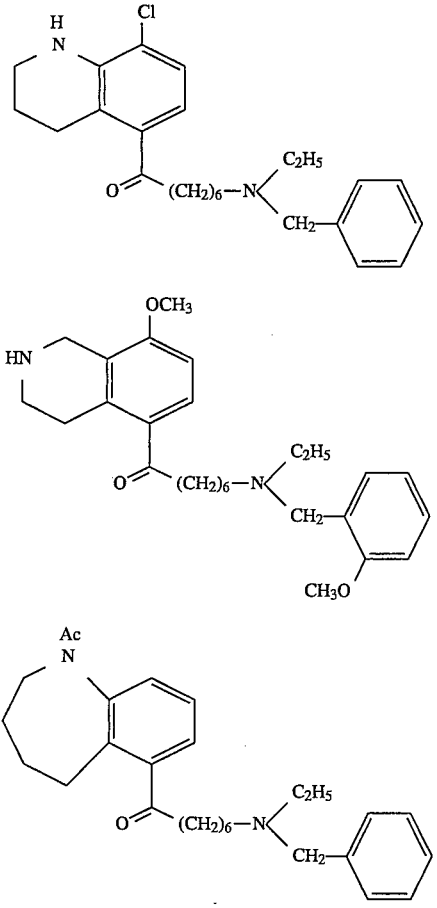
TABLE 13-continued
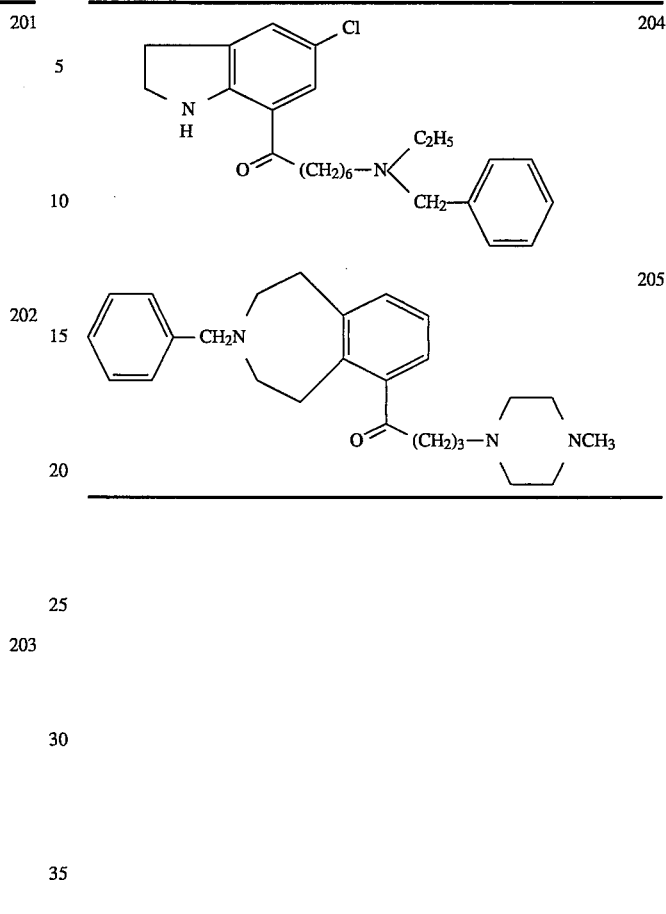
TABLE 14
| No. | X | k | m | n | $Z^1$ | $Z^2$ | $Z^3$ | $N\begin{matrix}R^3\\R^4\end{matrix}$ |
|---|---|---|---|---|---|---|---|---|
| 206 | NH | 2 | 2 | 2 | H | H | H | N(CH2CH2)2N—CH2Ph |
| 207 | NAc | 2 | 2 | 2 | H | H | H | N(CH2CH2)2N—CH2Ph |
| 208 | NCOPh | 2 | 2 | 2 | H | H | H | N(CH2CH2)2N—CH2Ph |

TABLE 14-continued

| No. | X | k | m | n | Z¹ | Z² | Z³ | N<R³/R⁴ |
|---|---|---|---|---|---|---|---|---|
| 209 | NCH₃ | 2 | 2 | 2 | H | H | H | N⌒N—CH₂Ph |
| 210 | NC₂H₅ | 2 | 2 | 2 | H | H | H | N⌒N—CH₂Ph |
| 211 | NCH(CH₃)₂ | 2 | 2 | 2 | H | H | H | N⌒N—CH₂Ph |
| 212 | NC₃H₇ | 2 | 2 | 2 | H | H | H | N⌒N—CH₂Ph |
| 213 | NCHPh₂ | 2 | 2 | 2 | H | H | H | N⌒N—CH₂Ph |
| 214 | NCONHCH₃ | 2 | 2 | 2 | H | H | H | N⌒N—CH₂Ph |
| 215 | NSO₂Ph | 2 | 2 | 2 | H | H | H | N⌒N—CH₂Ph |
| 216 | NSO₂CH₃ | 2 | 2 | 2 | H | H | H | N⌒N—CH₂Ph |
| 217 | NCH₂–C₆H₄–CH₃ | 2 | 2 | 2 | H | H | H | N⌒N—CH₂Ph |
| 218 | NCH₂–C₆H₄–OCH₃ | 2 | 2 | 2 | H | H | H | N⌒N—CH₂Ph |
| 219 | NCH₂–C₆H₄–Cl | 2 | 2 | 2 | H | H | H | N⌒N—CH₂Ph |
| 220 | NCH₂–C₆H₄–F | 2 | 2 | 2 | H | H | H | N⌒N—CH₂Ph |

TABLE 15
| No. | X | k | m | n | $Z^1$ | $Z^2$ | $Z^3$ | $\begin{array}{c}R^3\\ \diagdown\\ N\\ \diagup\\ R^4\end{array}$ |
|---|---|---|---|---|---|---|---|---|
| 221 | 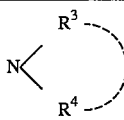 | 2 | 2 | 2 | H | H | H | 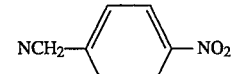 |
| 222 | 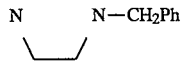 | 2 | 2 | 2 | H | H | H | 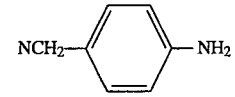 |
| 223 | 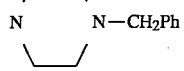 | 2 | 2 | 2 | H | H | H |  |
| 224 | 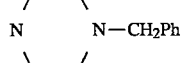 | 2 | 2 | 2 | H | H | H | 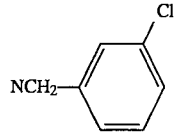 |
| 225 | 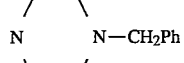 | 2 | 2 | 2 | H | H | H | 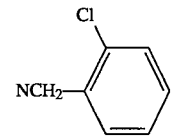 |
| 226 | 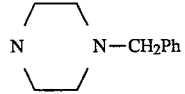 | 2 | 2 | 2 | H | H | H | 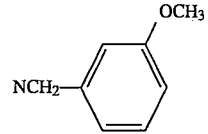 |
| 227 | 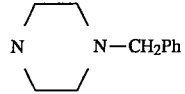 | 2 | 2 | 2 | H | H | H | 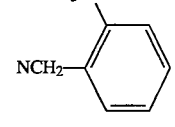 |
| 228 | 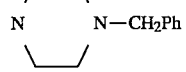 | 2 | 2 | 2 | H | H | H | 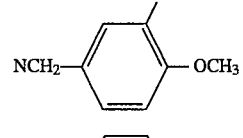 |
| 229 | 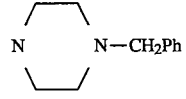 | 2 | 2 | 2 | H | H | H | 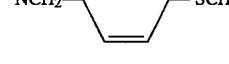 |
| 230 | 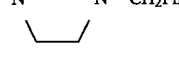 | 2 | 2 | 2 | H | H | H | 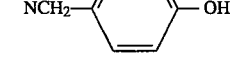 |
| 231 | NH | 2 | 2 | 2 | H | H | H | 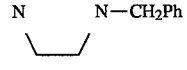 |
| 232 | NH | 2 | 2 | 2 | H | H | H | 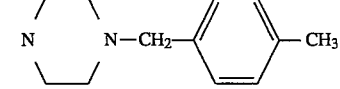 |

TABLE 15-continued
| No. | X | k | m | n | $Z^1$ | $Z^2$ | $Z^3$ | $N(R^3)(R^4)$ |
|---|---|---|---|---|---|---|---|---|
| 233 | NH | 2 | 2 | 2 | H | H | H | 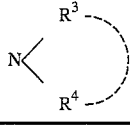 |
| 234 | NH | 2 | 2 | 2 | H | H | H | 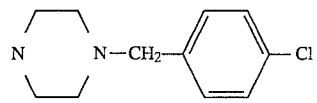 |
| 235 | NH | 2 | 2 | 2 | H | H | H | 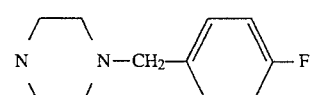 |
| 236 | NH | 2 | 2 | 2 | H | H | H | 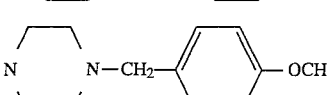 |
| 237 | NH | 2 | 2 | 2 | H | H | H | 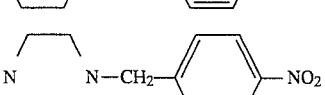 |
| 238 | NH | 2 | 2 | 2 | H | H | H | 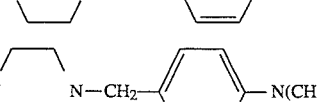 |
| 239 | NH | 2 | 2 | 2 | H | H | H | 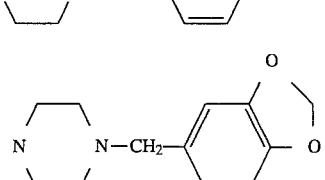 |
| 240 | NH | 2 | 2 | 2 | H | H | H | 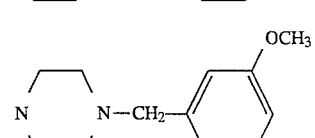 |
TABLE 16
| No. | X | k | m | n | $Z^1$ | $Z^2$ | $Z^3$ | $N(R^3)(R^4)$ |
|---|---|---|---|---|---|---|---|---|
| 241 | NH | 2 | 2 | 2 | H | H | H | 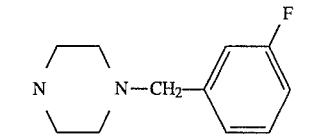 |

TABLE 16-continued
| No. | X | k | m | n | Z¹ | Z² | Z³ | $\underset{R^4}{\overset{R^3}{N\diagdown}}$ |
|---|---|---|---|---|---|---|---|---|
| 242 | NH | 2 | 2 | 2 | H | H | H | 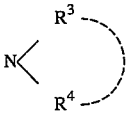 |
| 243 | NH | 2 | 2 | 2 | H | H | H | 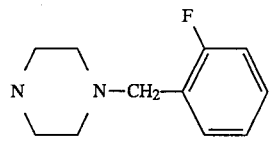 |
| 244 | NH | 2 | 2 | 2 | H | H | H | 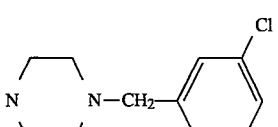 |
| 245 | NH | 2 | 2 | 2 | H | H | H | 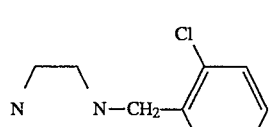 |
| 246 | NH | 2 | 2 | 2 | H | H | H | 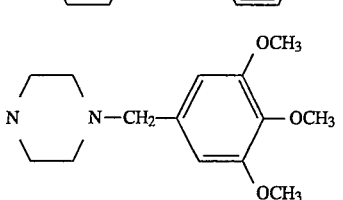 |
| 247 | NH | 2 | 2 | 2 | H | H | H | 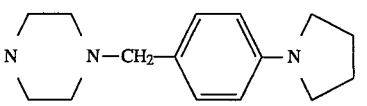 |
| 248 | NH | 2 | 2 | 2 | H | H | H | 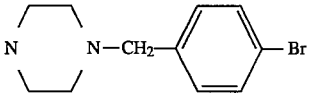 |
| 249 | NH | 2 | 2 | 2 | H | H | H | 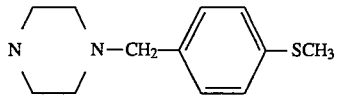 |
| 250 | NH | 2 | 2 | 2 | H | H | H | 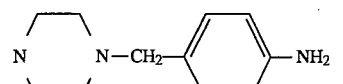 |
| 251 | NCH₂Ph | 2 | 2 | 2 | H | H | H | 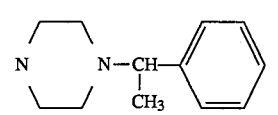 |
| 252 | NCH₂Ph | 2 | 2 | 2 | H | H | H | 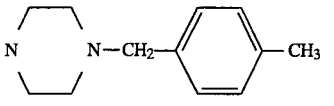 |
| 253 | NCH₂Ph | 2 | 2 | 2 | H | H | H | 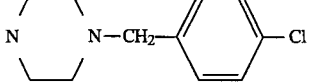 |

TABLE 16-continued
| No. | X | k | m | n | $Z^1$ | $Z^2$ | $Z^3$ | $N(R^3)(R^4)$ |
|---|---|---|---|---|---|---|---|---|
| 254 | NCH$_2$Ph | 2 | 2 | 2 | H | H | H | 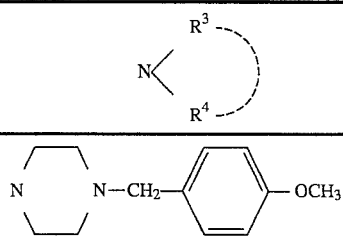 |
| 255 | NCH$_2$Ph | 2 | 2 | 2 | H | H | H | 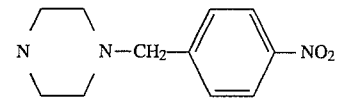 |
| 256 | NCH$_2$Ph | 2 | 2 | 2 | H | H | H | 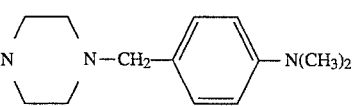 |
| 257 | NCH$_2$Ph | 2 | 2 | 2 | H | H | H | 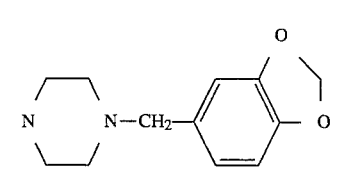 |
| 258 | NCH$_2$Ph | 2 | 2 | 2 | H | H | H | 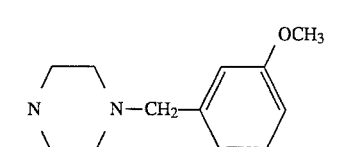 |
| 259 | NCH$_2$Ph | 2 | 2 | 2 | H | H | H | 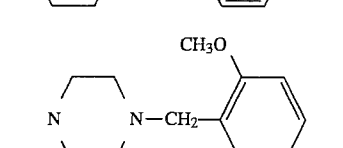 |
| 260 | NCH$_2$Ph | 2 | 2 | 2 | H | H | H | 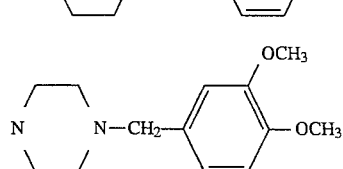 |
TABLE 17
| No. | X | k | m | n | $Z^1$ | $Z^2$ | $Z^3$ | $N(R^3)(R^4)$ |
|---|---|---|---|---|---|---|---|---|
| 261 | NCH$_2$Ph | 2 | 2 | 2 | H | H | H | 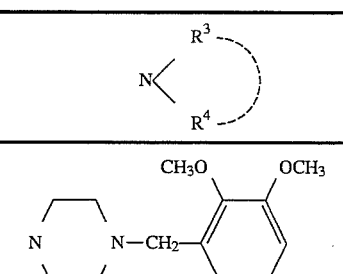 |
| 262 | NCH$_2$Ph | 2 | 2 | 2 | H | H | H | 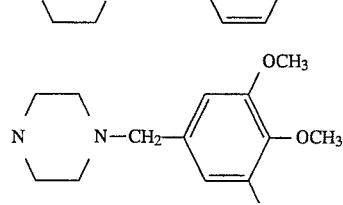 |

TABLE 17-continued

| No. | X | k | m | n | $Z^1$ | $Z^2$ | $Z^3$ | $\begin{array}{c}R^3 \\ N< \\ R^4\end{array}$ |
|---|---|---|---|---|---|---|---|---|
| 263 | NCH₂Ph | 2 | 2 | 2 | H | H | H | piperazinyl-CH₂-(2-F-phenyl) |
| 264 | NCH₂Ph | 2 | 2 | 2 | H | H | H | piperazinyl-CH₂-(3-F-phenyl) |
| 265 | NCH₂Ph | 2 | 2 | 2 | H | H | H | piperazinyl-CH₂-(2-Cl-phenyl) |
| 266 | NCH₂Ph | 2 | 2 | 2 | H | H | H | piperazinyl-CH₂-(3-Cl-phenyl) |
| 267 | NCH₂Ph | 2 | 2 | 2 | H | H | H | piperazinyl-CH₂-(3-NO₂-phenyl) |
| 268 | NCH₂Ph | 2 | 2 | 2 | H | H | H | piperazinyl-CH₂-(3-Br-phenyl) |
| 269 | NCH₂Ph | 2 | 2 | 2 | H | H | H | piperazinyl-CH₂-(4-Br-phenyl) |
| 270 | NCH₂Ph | 2 | 2 | 2 | H | H | H | piperazinyl-CH₂-(4-NH₂-phenyl) |
| 271 | NCH₂Ph | 2 | 2 | 2 | H | H | H | piperazinyl-CH₂-(4-pyrrolidinyl-phenyl) |
| 272 | NCH₂Ph | 2 | 2 | 2 | H | H | H | piperazinyl-CH₂-(4-SCH₃-phenyl) |
| 273 | NCH₂Ph | 2 | 2 | 2 | H | H | H | piperazinyl-CH₂-(4-OH-phenyl) |

TABLE 17-continued
| No. | X | k | m | n | Z¹ | Z² | Z³ | $\overset{R^3}{\underset{R^4}{N}}$ |
|---|---|---|---|---|---|---|---|---|
| 274 | NCH₂Ph | 2 | 2 | 2 | H | H | H | 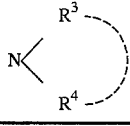 |
| 275 | NCH₂Ph | 2 | 2 | 2 | H | H | H | 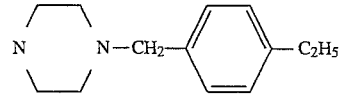 |
| 276 | NCH₂Ph | 2 | 2 | 2 | H | H | H | 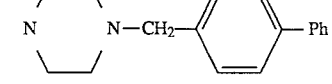 |
| 277 | NCH₂Ph | 2 | 2 | 2 | H | H | H | 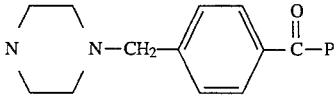 |
| 278 | NCH₂Ph | 2 | 2 | 2 | H | H | H | 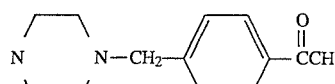 |
| 279 | NCH₂Ph | 2 | 2 | 2 | H | H | H |  |
| 280 | NCH₂Ph | 2 | 2 | 2 | H | H | H | 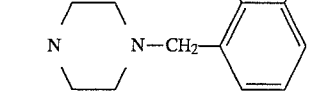 |
TABLE 18
| No. | X | k | m | n | Z¹ | Z² | Z³ | $\overset{R^3}{\underset{R^4}{N}}$ |
|---|---|---|---|---|---|---|---|---|
| 281 | NAc | 2 | 2 | 2 | H | H | H |  |
| 282 | NAc | 2 | 2 | 2 | H | H | H | 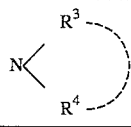 |
| 283 | NAc | 2 | 2 | 2 | H | H | H | 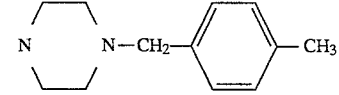 |

TABLE 18-continued
| No. | X | k | m | n | $Z^1$ | $Z^2$ | $Z^3$ | $N\langle{}^{R^3}_{R^4}$ |
|---|---|---|---|---|---|---|---|---|
| 284 | NAc | 2 | 2 | 2 | H | H | H | 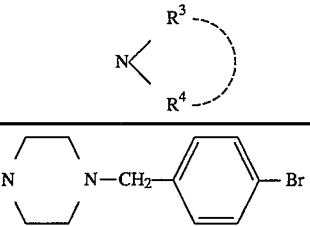 |
| 285 | NAc | 2 | 2 | 2 | H | H | H | 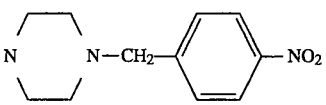 |
| 286 | NAc | 2 | 2 | 2 | H | H | H | 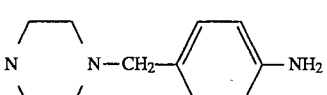 |
| 287 | NAc | 2 | 2 | 2 | H | H | H | 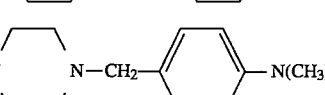 |
| 288 | NAc | 2 | 2 | 2 | H | H | H | 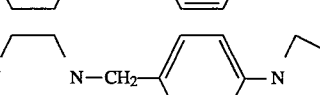 |
| 289 | NAc | 2 | 2 | 2 | H | H | H | 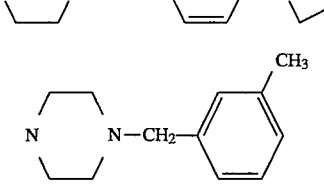 |
| 290 | NAc | 2 | 2 | 2 | H | H | H | 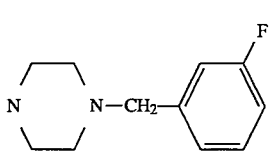 |
| 291 | NAc | 2 | 2 | 2 | H | H | H | 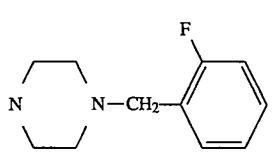 |
| 292 | NAc | 2 | 2 | 2 | H | H | H | 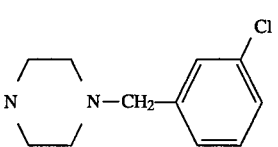 |
| 293 | NAc | 2 | 2 | 2 | H | H | H | 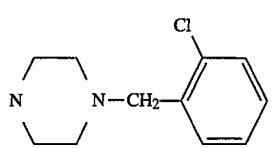 |
| 294 | NAc | 2 | 2 | 2 | H | H | H | 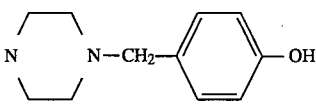 |

TABLE 18-continued
| No. | X | k | m | n | Z¹ | Z² | Z³ | $\overset{R^3}{\underset{R^4}{N\!\!\diagup}}$ |
|---|---|---|---|---|---|---|---|---|
| 295 | NAc | 2 | 2 | 2 | H | H | H | 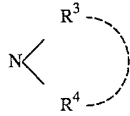 |
| 296 | NAc | 2 | 2 | 2 | H | H | H | 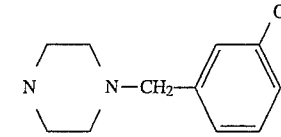 |
| 297 | NAc | 2 | 2 | 2 | H | H | H | 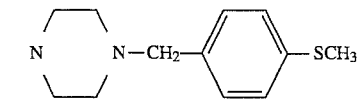 |
| 298 | NAc | 2 | 2 | 2 | H | H | H | 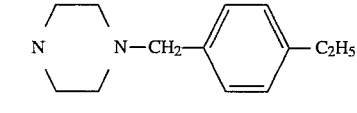 |
| 299 | NAc | 2 | 2 | 2 | H | H | H | 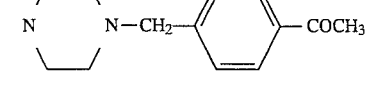 |
| 300 | NAc | 2 | 2 | 2 | H | H | H | 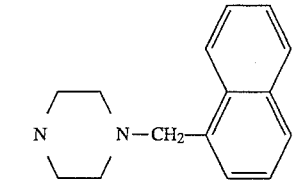 |
TABLE 19
| No. | X | k | m | n | Z¹ | Z² | Z³ | $\overset{R^3}{\underset{R^4}{N\!\!\diagup}}$ |
|---|---|---|---|---|---|---|---|---|
| 301 | NCH₃ | 2 | 2 | 2 | H | H | H | 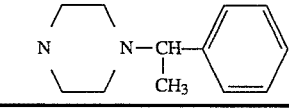 |
| 302 | NCH₃ | 2 | 2 | 2 | H | H | H | 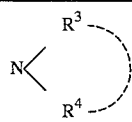 |
| 303 | NCH₃ | 2 | 2 | 2 | H | H | H | 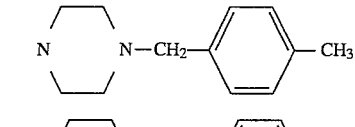 |
| 304 | NCH₃ | 2 | 2 | 2 | H | H | H | 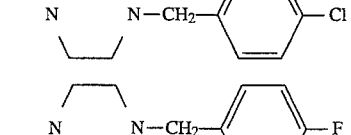 |

TABLE 19-continued

| No. | X | k | m | n | $Z^1$ | $Z^2$ | $Z^3$ | $N{<}^{R^3}_{R^4}$ |
|---|---|---|---|---|---|---|---|---|
| 305 | NCH$_3$ | 2 | 2 | 2 | H | H | H | piperazine-N-CH$_2$-C$_6$H$_4$-NO$_2$ (para) |
| 306 | NCH$_3$ | 2 | 2 | 2 | H | H | H | piperazine-N-CH$_2$-C$_6$H$_4$-NH$_2$ (para) |
| 307 | NCH$_3$ | 2 | 2 | 2 | H | H | H | piperazine-N-CH$_2$-C$_6$H$_4$-N(CH$_3$)$_2$ (para) |
| 308 | NCH$_3$ | 2 | 2 | 2 | H | H | H | piperazine-N-CH$_2$-C$_6$H$_4$-N-pyrrolidine (para) |
| 309 | NCH$_3$ | 2 | 2 | 2 | H | H | H | piperazine-N-CH$_2$-C$_6$H$_4$-CH$_3$ (meta) |
| 310 | NCH$_3$ | 2 | 2 | 2 | H | H | H | piperazine-N-CH$_2$-C$_6$H$_4$-F (meta) |
| 311 | NCH$_3$ | 2 | 2 | 2 | H | H | H | piperazine-N-CH$_2$-C$_6$H$_4$-F (ortho) |
| 312 | NCH$_3$ | 2 | 2 | 2 | H | H | H | piperazine-N-CH$_2$-C$_6$H$_4$-Cl (meta) |
| 313 | NCH$_3$ | 2 | 2 | 2 | H | H | H | piperazine-N-CH$_2$-C$_6$H$_4$-Cl (ortho) |
| 314 | NCH$_3$ | 2 | 2 | 2 | H | H | H | piperazine-N-CH$_2$-C$_6$H$_4$-OH (para) |
| 315 | NCH$_3$ | 2 | 2 | 2 | H | H | H | piperazine-N-CH$_2$-C$_6$H$_4$-OH (meta) |

TABLE 19-continued

| No. | X | k | m | n | Z¹ | Z² | Z³ | $\overset{R^3}{\underset{R^4}{N{<}}}$ |
|---|---|---|---|---|---|---|---|---|
| 316 | NCH₃ | 2 | 2 | 2 | H | H | H | piperazine-N-CH₂-C₆H₄-SCH₃ |
| 317 | NCH₃ | 2 | 2 | 2 | H | H | H | piperazine-N-CH₂-C₆H₄-C₂H₅ |
| 318 | NCH₃ | 2 | 2 | 2 | H | H | H | piperazine-N-CH₂-C₆H₄-COCH₃ |
| 319 | NCH₃ | 2 | 2 | 2 | H | H | H | piperazine-N-CH₂-(1-naphthyl) |
| 320 | NCH₃ | 2 | 2 | 2 | H | H | H | piperazine-N-CH(CH₃)-C₆H₅ |

TABLE 20

| No. | X | k | m | n | Z¹ | Z² | Z³ | $\overset{R^3}{\underset{R^4}{N{<}}}$ |
|---|---|---|---|---|---|---|---|---|
| 321 | NH | 2 | 2 | 2 | H | H | H | morpholino |
| 322 | NH | 2 | 2 | 2 | H | H | H | 4-(4-fluorobenzoyl)piperidino |
| 323 | NH | 2 | 2 | 2 | H | H | H | 4-benzylpiperidino |
| 324 | NH | 2 | 2 | 2 | H | H | H | 4-oxopiperidino |
| 325 | NH | 2 | 2 | 2 | H | H | H | 4-acetylpiperazino |

TABLE 20-continued
| No. | X | k | m | n | Z¹ | Z² | Z³ | $\overset{R^3}{\underset{R^4}{N}}$ |
|---|---|---|---|---|---|---|---|---|
| 326 | NH | 2 | 2 | 2 | H | H | H | 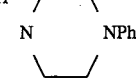 |
| 327 | NH | 2 | 2 | 2 | H | H | H | 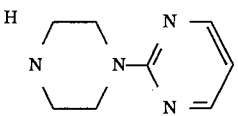 |
| 328 | NH | 2 | 2 | 2 | H | H | H | 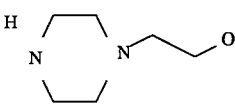 |
| 329 | NH | 2 | 2 | 2 | H | H | H | 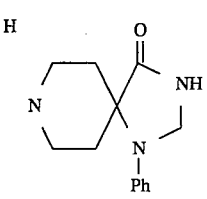 |
| 330 | NH | 2 | 2 | 2 | H | H | H | 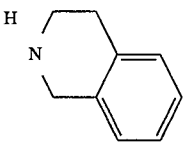 |
| 331 | NH | 2 | 2 | 2 | H | H | H | 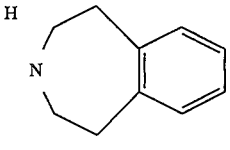 |
| 332 | NH | 2 | 2 | 2 | H | H | H | 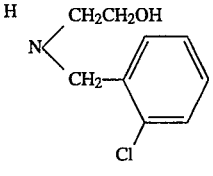 |
| 333 | NH | 2 | 2 | 2 | H | H | H |  |
| 334 | NH | 2 | 2 | 2 | H | H | H | 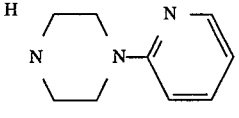 |
| 335 | NH | 2 | 2 | 2 | H | H | H | NH₂ |
| 336 | NH | 2 | 2 | 2 | H | H | H | 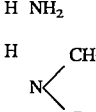 |
| 337 | NH | 2 | 2 | 2 | H | H | H | 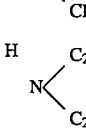 |

TABLE 20-continued

| No. | X | k | m | n | $Z^1$ | $Z^2$ | $Z^3$ | $\begin{array}{c}R^3\\N{<}\\R^4\end{array}$ |
|---|---|---|---|---|---|---|---|---|
| 338 | NH | 2 | 2 | 2 | H | H | H | thiazolidine (N-CH2-CH2-S ring) |
| 339 | NH | 2 | 2 | 2 | H | H | H | N(H)(CH2CH2Ph) |
| 340 | NH | 2 | 2 | 2 | H | H | H | piperazine-N-CH2CH2Ph |

TABLE 21

| No. | X | k | m | n | $Z^1$ | $Z^2$ | $Z^3$ | $\begin{array}{c}R^3\\N{<}\\R^4\end{array}$ |
|---|---|---|---|---|---|---|---|---|
| 341 | NAc | 2 | 2 | 2 | H | H | H | morpholine |
| 342 | NAc | 2 | 2 | 2 | H | H | H | 4-(4-fluorobenzoyl)piperidine |
| 343 | NAc | 2 | 2 | 2 | H | H | H | 4-benzylpiperidine |
| 344 | NAc | 2 | 2 | 2 | H | H | H | 4-oxopiperidine |
| 345 | NAc | 2 | 2 | 2 | H | H | H | 4-acetylpiperazine |
| 346 | NAc | 2 | 2 | 2 | H | H | H | 4-phenylpiperazine |
| 347 | NAc | 2 | 2 | 2 | H | H | H | 4-(2-pyrimidinyl)piperazine |
| 348 | NAc | 2 | 2 | 2 | H | H | H | 4-(2-hydroxyethyl)piperazine |

TABLE 21-continued
| No. | X | k | m | n | $Z^1$ | $Z^2$ | $Z^3$ | $N\begin{subarray}{l}R^3\\R^4\end{subarray}$ |
|---|---|---|---|---|---|---|---|---|
| 349 | NAc | 2 | 2 | 2 | H | H | H | 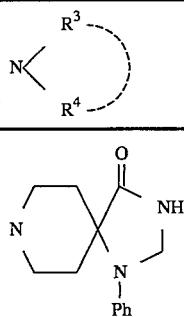 |
| 350 | NAc | 2 | 2 | 2 | H | H | H | 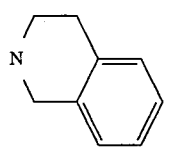 |
| 351 | NAc | 2 | 2 | 2 | H | H | H | 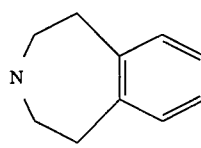 |
| 352 | NAc | 2 | 2 | 2 | H | H | H | 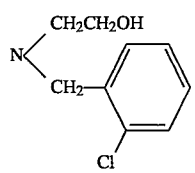 |
| 353 | NAc | 2 | 2 | 2 | H | H | H | 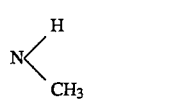 |
| 354 | NAc | 2 | 2 | 2 | H | H | H | 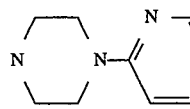 |
| 355 | NAc | 2 | 2 | 2 | H | H | H | $NH_2$ |
| 356 | NAc | 2 | 2 | 2 | H | H | H | 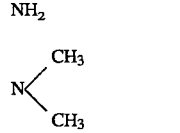 |
| 357 | NAc | 2 | 2 | 2 | H | H | H | 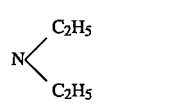 |
| 358 | NAc | 2 | 2 | 2 | H | H | H | 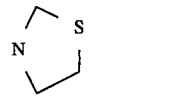 |
| 359 | NAc | 2 | 2 | 2 | H | H | H | 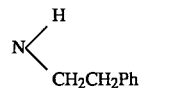 |
| 360 | NAc | 2 | 2 | 2 | H | H | H | 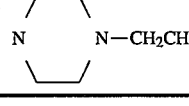 |

TABLE 22

![structure: N(R³)(R⁴) with dashed bond]

| No. | X | k | m | n | Z¹ | Z² | Z³ | NR³R⁴ |
|---|---|---|---|---|---|---|---|---|
| 361 | NCH₃ | 2 | 2 | 2 | H | H | H | morpholino (N—O ring) |
| 362 | NCH₃ | 2 | 2 | 2 | H | H | H | 4-(4-fluorobenzoyl)piperidin-1-yl |
| 363 | NCH₃ | 2 | 2 | 2 | H | H | H | 4-(CH₂Ph)piperidin-1-yl |
| 364 | NCH₃ | 2 | 2 | 2 | H | H | H | 4-oxopiperidin-1-yl |
| 365 | NCH₃ | 2 | 2 | 2 | H | H | H | 4-acetylpiperazin-1-yl (N—NAc) |
| 366 | NCH₃ | 2 | 2 | 2 | H | H | H | 4-phenylpiperazin-1-yl (N—NPh) |
| 367 | NCH₃ | 2 | 2 | 2 | H | H | H | 4-(pyrimidin-2-yl)piperazin-1-yl |
| 368 | NCH₃ | 2 | 2 | 2 | H | H | H | 4-(2-hydroxyethyl)piperazin-1-yl |
| 369 | NCH₃ | 2 | 2 | 2 | H | H | H | 1-phenyl-1,3,8-triazaspiro[4.5]decan-4-one-8-yl |
| 370 | NCH₃ | 2 | 2 | 2 | H | H | H | 1,2,3,4-tetrahydroisoquinolin-2-yl |
| 371 | NCH₃ | 2 | 2 | 2 | H | H | H | 2,3,4,5-tetrahydro-1H-2-benzazepin-2-yl |

TABLE 22-continued

| No. | X | k | m | n | Z¹ | Z² | Z³ | $\underset{N}{\overset{R^3}{\diagdown}} R^4$ |
|---|---|---|---|---|---|---|---|---|
| 372 | NCH₃ | 2 | 2 | 2 | H | H | H | N(CH₂CH₂OH)(CH₂-2-chlorophenyl) |
| 373 | NCH₃ | 2 | 2 | 2 | H | H | H | NH(CH₃) |
| 374 | NCH₃ | 2 | 2 | 2 | H | H | H | 4-(pyridin-2-yl)piperazin-1-yl |
| 375 | NCH₃ | 2 | 2 | 2 | H | H | H | NH₂ |
| 376 | NCH₃ | 2 | 2 | 2 | H | H | H | N(CH₃)₂ |
| 377 | NCH₃ | 2 | 2 | 2 | H | H | H | N(C₂H₅)₂ |
| 378 | NCH₃ | 2 | 2 | 2 | H | H | H | thiazolidin-3-yl |
| 379 | NCH₃ | 2 | 2 | 2 | H | H | H | NH(CH₂CH₂Ph) |
| 380 | NCH₃ | 2 | 2 | 2 | H | H | H | 4-(2-phenylethyl)piperazin-1-yl |

TABLE 23

| No. | X | k | m | n | Z¹ | Z² | Z³ | $\underset{N}{\overset{R^3}{\diagdown}} R^4$ |
|---|---|---|---|---|---|---|---|---|
| 381 | NCH₂Ph | 2 | 2 | 2 | H | H | H | morpholin-4-yl |
| 382 | NCH₂Ph | 2 | 2 | 2 | H | H | H | 4-(4-fluorobenzoyl)piperidin-1-yl |

TABLE 23-continued
| No. | X | k | m | n | $Z^1$ | $Z^2$ | $Z^3$ | $\begin{array}{c}R^3\\ \diagup\\ N\\ \diagdown\\ R^4\end{array}$ |
|---|---|---|---|---|---|---|---|---|
| 383 | NCH$_2$Ph | 2 | 2 | 2 | H | H | H | 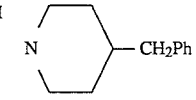 |
| 384 | NCH$_2$Ph | 2 | 2 | 2 | H | H | H | 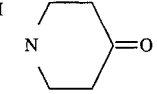 |
| 385 | NCH$_2$Ph | 2 | 2 | 2 | H | H | H | 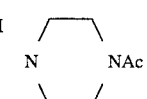 |
| 386 | NCH$_2$Ph | 2 | 2 | 2 | H | H | H | 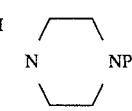 |
| 387 | NCH$_2$Ph | 2 | 2 | 2 | H | H | H | 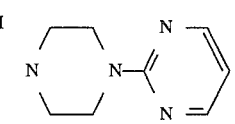 |
| 388 | NCH$_2$Ph | 2 | 2 | 2 | H | H | H | 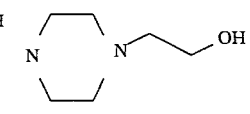 |
| 389 | NCH$_2$Ph | 2 | 2 | 2 | H | H | H | 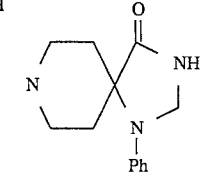 |
| 390 | NCH$_2$Ph | 2 | 2 | 2 | H | H | H | 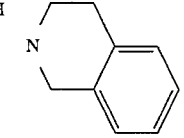 |
| 391 | NCH$_2$Ph | 2 | 2 | 2 | H | H | H | 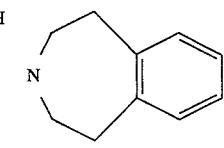 |
| 392 | NCH$_2$Ph | 2 | 2 | 2 | H | H | H | 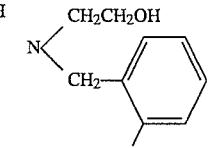 |
| 393 | NCH$_2$Ph | 2 | 2 | 2 | H | H | H |  |

TABLE 23-continued

| No. | X | k | m | n | Z¹ | Z² | Z³ | NR³R⁴ group |
|-----|---|---|---|---|----|----|----|----|
| 394 | NCH₂Ph | 2 | 2 | 2 | H | H | H | piperazinyl-(2-pyridyl) |
| 395 | NCH₂Ph | 2 | 2 | 2 | H | H | H | NH₂ |
| 396 | NCH₂Ph | 2 | 2 | 2 | H | H | H | N(CH₃)₂ |
| 397 | NCH₂Ph | 2 | 2 | 2 | H | H | H | N(C₂H₅)₂ |
| 398 | NCH₂Ph | 2 | 2 | 2 | H | H | H | thiazolidinyl |
| 399 | NCH₂Ph | 2 | 2 | 2 | H | H | H | NH-CH₂CH₂Ph |
| 400 | NCH₂Ph | 2 | 2 | 2 | H | H | H | piperazinyl-N-CH₂CH₂Ph |

TABLE 24

| No. | X | k | m | n | Z¹ | Z² | Z³ | NR³R⁴ group |
|-----|---|---|---|---|----|----|----|----|
| 401 | NCH₂Ph | 2 | 2 | 3 | H | H | H | 4-(4-fluorobenzoyl)piperidinyl |
| 402 | NCH₂Ph | 2 | 2 | 3 | H | H | H | 1-phenyl-1,3,8-triazaspiro[4.5]decan-4-one |
| 403 | NCH₂Ph | 2 | 2 | 3 | H | H | H | piperazinyl-N-CHPh₂ |
| 404 | NCH₂Ph | 2 | 2 | 3 | H | H | H | piperazinyl-(2-pyrimidinyl) |

TABLE 24-continued

| No. | X | k | m | n | Z¹ | Z² | Z³ | $\begin{matrix}R^3\\N\\R^4\end{matrix}$ |
|---|---|---|---|---|---|---|---|---|
| 405 | NCH₂Ph | 2 | 2 | 3 | H | H | H | N(CH₃)₂ |
| 406 | NCH₃ | 2 | 2 | 3 | H | H | H | 4-(4-fluorobenzoyl)piperidin-1-yl |
| 407 | NCH₃ | 2 | 2 | 3 | H | H | H | 4-oxo-1-phenyl-1,3,8-triazaspiro[4.5]decan-8-yl |
| 408 | NCH₃ | 2 | 2 | 3 | H | H | H | 4-(diphenylmethyl)piperazin-1-yl |
| 409 | NCH₃ | 2 | 2 | 3 | H | H | H | 4-(pyrimidin-2-yl)piperazin-1-yl |
| 410 | NCH₃ | 2 | 2 | 3 | H | H | H | N(CH₃)₂ |
| 411 | NH | 2 | 2 | 3 | H | H | H | 4-(4-fluorobenzoyl)piperidin-1-yl |
| 412 | NH | 2 | 2 | 3 | H | H | H | 4-oxo-1-phenyl-1,3,8-triazaspiro[4.5]decan-8-yl |
| 413 | NH | 2 | 2 | 3 | H | H | H | 4-(diphenylmethyl)piperazin-1-yl |
| 414 | NH | 2 | 2 | 3 | H | H | H | 4-(pyrimidin-2-yl)piperazin-1-yl |
| 415 | NH | 2 | 2 | 3 | H | H | H | N(CH₃)₂ |
| 416 | NAc | 2 | 2 | 3 | H | H | H | 4-(4-fluorobenzoyl)piperidin-1-yl |

TABLE 24-continued
| No. | X | k | m | n | Z¹ | Z² | Z³ | $\begin{array}{c}R^3 \\ N \\ R^4\end{array}$ |
|---|---|---|---|---|---|---|---|---|
| 417 | NAc | 2 | 2 | 3 | H | H | H | 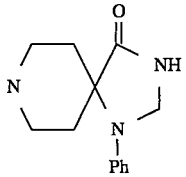 |
| 418 | NAc | 2 | 2 | 3 | H | H | H |  N—CHPh₂ |
| 419 | NAc | 2 | 2 | 3 | H | H | H | 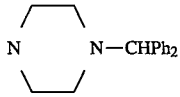 |
| 420 | NAc | 2 | 2 | 3 | H | H | H | N(CH₃)₂ |
TABLE 25
| No. | X | k | m | n | Z¹ | Z² | Z³ | $\begin{array}{c}R^3 \\ N \\ R^4\end{array}$ |
|---|---|---|---|---|---|---|---|---|
| 421 | NH | 2 | 2 | 1 | H | H | H |  N—CH₂Ph |
| 422 | NAc | 2 | 2 | 1 | H | H | H | 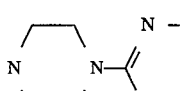 N—CH₂Ph |
| 423 | NCH₃ | 2 | 2 | 1 | H | H | H |  N—CH₂Ph |
| 424 | NCH₂Ph | 2 | 2 | 1 | H | H | H | 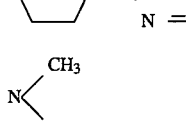 N—CH₂Ph |
| 425 | NAc | 2 | 2 | 1 | H | H | H |  |
| 426 | NCH₂Ph | 2 | 2 | 1 | H | H | H | 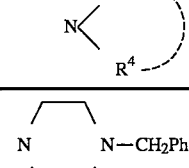 |
| 427 | NH | 2 | 2 | 3 | H | H | H |  N—CH₂Ph |

TABLE 25-continued

| No. | X | k | m | n | $Z^1$ | $Z^2$ | $Z^3$ | $\begin{matrix} R^3 \\ N \\ R^4 \end{matrix}$ |
|---|---|---|---|---|---|---|---|---|
| 428 | NAc | 2 | 2 | 3 | H | H | H | N⟨piperazine⟩N—CH₂Ph |
| 429 | NCH₃ | 2 | 2 | 3 | H | H | H | N⟨piperazine⟩N—CH₂Ph |
| 430 | NCH₂Ph | 2 | 2 | 3 | H | H | H | N⟨piperazine⟩N—CH₂Ph |
| 431 | NAc | 2 | 2 | 3 | H | H | H | N⟨piperidine⟩ |
| 432 | NCH₂Ph | 2 | 2 | 3 | H | H | H | N⟨piperidine⟩ |
| 433 | NH | 2 | 2 | 4 | H | H | H | N⟨piperazine⟩N—CH₂Ph |
| 434 | NAc | 2 | 2 | 4 | H | H | H | N⟨piperazine⟩N—CH₂Ph |
| 435 | NCH₃ | 2 | 2 | 4 | H | H | H | N⟨piperazine⟩N—CH₂Ph |
| 436 | NCH₂Ph | 2 | 2 | 4 | H | H | H | N⟨piperazine⟩N—CH₂Ph |
| 437 | NAc | 2 | 2 | 4 | H | H | H | N⟨piperidine⟩ |
| 438 | NCH₂Ph | 2 | 2 | 4 | H | H | H | N⟨piperidine⟩ |
| 439 | NAc | 2 | 2 | 1 | H | H | H | CH₃N-⟨piperidine⟩-N—CH₂Ph |
| 440 | NH | 2 | 2 | 1 | H | H | H | HN-⟨piperidine⟩-N—CH₂Ph |

TABLE 26

| No. | X | k | m | n | $Z^1$ | $Z^2$ | $Z^3$ | $N<\genfrac{}{}{0pt}{}{R^3}{R^4}$ |
|---|---|---|---|---|---|---|---|---|
| 441 | NCH$_2$Ph | 0 | 3 | 2 | H | H | H | piperazine-N—CH$_2$Ph |
| 442 | NH | 0 | 3 | 2 | H | H | H | piperazine-N—CH$_2$Ph |
| 443 | NCO$_2$C$_2$H$_5$ | 0 | 3 | 2 | H | H | H | piperazine-N—CH$_2$Ph |
| 444 | NAc | 0 | 3 | 2 | H | H | H | piperazine-N—CH$_2$Ph |
| 445 | NH | 0 | 3 | 1 | H | H | H | 4-(N-CH$_3$)-piperidine-N—CH$_2$Ph |
| 446 | NCH$_2$Ph | 0 | 4 | 2 | H | H | H | piperazine-N—CH$_2$Ph |
| 447 | NH | 0 | 4 | 2 | H | H | H | piperazine-N—CH$_2$Ph |
| 448 | NCO$_2$C$_2$H$_5$ | 0 | 4 | 2 | H | H | H | piperazine-N—CH$_2$Ph |
| 449 | NAc | 0 | 4 | 2 | H | H | H | piperazine-N—CH$_2$Ph |
| 450 | NH | 0 | 4 | 1 | H | H | H | 4-(N-CH$_3$)-piperidine-N—CH$_2$Ph |
| 451 | NCH$_2$Ph | 0 | 5 | 2 | H | H | H | piperazine-N—CH$_2$Ph |
| 452 | NH | 0 | 5 | 2 | H | H | H | piperazine-N—CH$_2$Ph |
| 453 | NCO$_2$C$_2$H$_5$ | 0 | 5 | 2 | H | H | H | piperazine-N—CH$_2$Ph |
| 454 | NAc | 0 | 5 | 2 | H | H | H | piperazine-N—CH$_2$Ph |

TABLE 26-continued
| No. | X | k | m | n | $Z^1$ | $Z^2$ | $Z^3$ | $N\!\!<\!\!{}^{R^3}_{R^4}$ |
|---|---|---|---|---|---|---|---|---|
| 455 | NH | 0 | 5 | 1 | H | H | H | 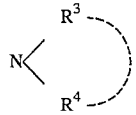 |
| 456 | NCH$_2$Ph | 1 | 3 | 2 | H | H | H | 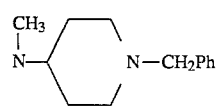 |
| 457 | NH | 1 | 3 | 2 | H | H | H | 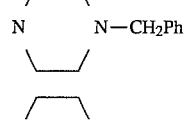 |
| 458 | NCO$_2$C$_2$H$_5$ | 1 | 3 | 2 | H | H | H | 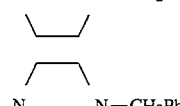 |
| 459 | NAc | 1 | 3 | 2 | H | H | H | 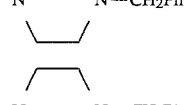 |
| 460 | NH | 1 | 3 | 1 | H | H | H | 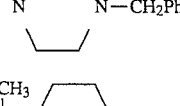 |
TABLE 27
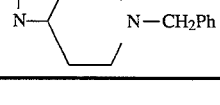
| No. | X | k | m | n | $Z^1$ | $Z^2$ | $Z^3$ | $N\!\!<\!\!{}^{R^3}_{R^4}$ |
|---|---|---|---|---|---|---|---|---|
| 461 | NCH$_2$Ph | 0 | 2 | 2 | H | H | H | 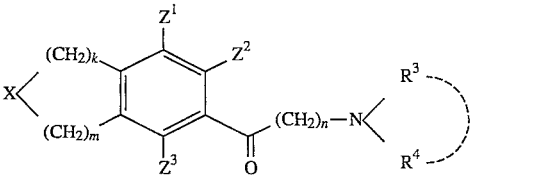 |
| 462 | NH | 0 | 2 | 2 | H | H | H | 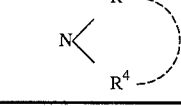 |
| 463 | NCH$_3$ | 0 | 2 | 2 | H | H | H | 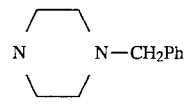 |

TABLE 27-continued

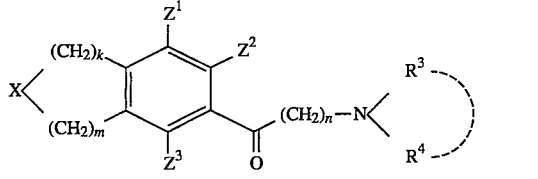

| No. | X | k | m | n | $Z^1$ | $Z^2$ | $Z^3$ | |
|---|---|---|---|---|---|---|---|---|
| 464 | NAc | 0 | 2 | 2 | H | H | H | N⟨piperazine⟩N—CH$_2$Ph |
| 465 | NCO$_2$C$_2$H$_5$ | 0 | 2 | 2 | H | H | H | N⟨piperazine⟩N—CH$_2$Ph |
| 466 | NCH$_2$Ph | 0 | 3 | 2 | H | H | H | N⟨piperazine⟩N—CH$_2$Ph |
| 467 | NH | 0 | 3 | 2 | H | H | H | N⟨piperazine⟩N—CH$_2$Ph |
| 468 | NCH$_3$ | 0 | 3 | 2 | H | H | H | N⟨piperazine⟩N—CH$_2$Ph |
| 469 | NAc | 0 | 3 | 2 | H | H | H | N⟨piperazine⟩N—CH$_2$Ph |
| 470 | NCO$_2$C$_2$H$_5$ | 0 | 3 | 2 | H | H | H | N⟨piperazine⟩N—CH$_2$Ph |
| 471 | NCH$_2$Ph | 0 | 4 | 2 | H | H | H | N⟨piperazine⟩N—CH$_2$Ph |
| 472 | NH | 0 | 4 | 2 | H | H | H | N⟨piperazine⟩N—CH$_2$Ph |
| 473 | NCH$_3$ | 0 | 4 | 2 | H | H | H | N⟨piperazine⟩N—CH$_2$Ph |
| 474 | NAc | 0 | 4 | 2 | H | H | H | N⟨piperazine⟩N—CH$_2$Ph |
| 475 | NCO$_2$C$_2$H$_5$ | 0 | 4 | 2 | H | H | H | N⟨piperazine⟩N—CH$_2$Ph |

TABLE 27-continued

[Structure: X connected via (CH₂)ₖ and (CH₂)ₘ to a benzene ring bearing Z¹, Z², Z³ substituents, with a -C(=O)-(CH₂)ₙ-NR³R⁴ group]

| No. | X | k | m | n | Z¹ | Z² | Z³ | NR³R⁴ |
|-----|---|---|---|---|----|----|----|-------|
| 476 | NCH₂Ph | 1 | 3 | 2 | H | H | H | N-piperazine-N—CH₂Ph |
| 477 | NH | 1 | 3 | 2 | H | H | H | N-piperazine-N—CH₂Ph |
| 478 | NCH₃ | 1 | 3 | 2 | H | H | H | N-piperazine-N—CH₂Ph |
| 479 | NAc | 1 | 3 | 2 | H | H | H | N-piperazine-N—CH₂Ph |
| 480 | NCO₂C₂H₅ | 1 | 3 | 2 | H | H | H | N-piperazine-N—CH₂Ph |

TABLE 28

| No. | X | k | m | n | Z¹ | Z² | Z³ | NR³R⁴ |
|-----|---|---|---|---|----|----|----|-------|
| 481 | NCH₂Ph | 1 | 2 | 2 | H | H | H | N-piperazine-N—CH₂Ph |
| 482 | NH | 1 | 2 | 2 | H | H | H | N-piperazine-N—CH₂Ph |
| 483 | NCH₃ | 1 | 2 | 2 | H | H | H | N-piperazine-N—CH₂Ph |
| 484 | NAc | 1 | 2 | 2 | H | H | H | N-piperazine-N—CH₂Ph |

TABLE 28-continued

|  |  |  |  |  |  |  |  | N⟨R³/R⁴ |
|---|---|---|---|---|---|---|---|---|
| No. | X | k | m | n | Z¹ | Z² | Z³ |  |
| 485 | NCO₂C₂H₅ | 1 | 2 | 2 | H | H | H | N‾‾N—CH₂Ph |
| 486 | O | 0 | 2 | 2 | H | H | H | N‾‾N—CH₂Ph |
| 487 | O | 0 | 2 | 2 | H | H | H | N(piperidine) |
| 488 | O | 0 | 2 | 2 | H | H | H | N‾‾N—CH₃ |
| 489 | O | 0 | 3 | 2 | H | H | H | N‾‾N—CH₂Ph |
| 490 | O | 0 | 3 | 2 | H | H | H | N‾‾N—CH₃ |
| 491 | O | 0 | 4 | 2 | H | H | H | N‾‾N—CH₂Ph |
| 492 | O | 0 | 4 | 2 | H | H | H | N‾‾O (morpholine) |
| 493 | O | 0 | 2 | 1 | H | H | H | CH₃–N–(piperidine)–N—CH₂Ph |
| 494 | S | 0 | 2 | 2 | H | H | H | N‾‾N—CH₂Ph |
| 495 | S | 0 | 2 | 2 | H | H | H | N‾‾N—Ph |
| 496 | S | 0 | 3 | 2 | H | H | H | N‾‾N—CH₂Ph |
| 497 | S | 0 | 3 | 2 | H | H | H | N(piperidine) |
| 498 | S | 0 | 4 | 2 | H | H | H | N‾‾N—CH₂Ph |

TABLE 28-continued
| No. | X | k | m | n | $Z^1$ | $Z^2$ | $Z^3$ | $N\langle{R^3 \atop R^4}$ |
|---|---|---|---|---|---|---|---|---|
| 499 | S | 0 | 4 | 2 | H | H | H | 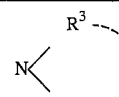 |
| 500 | S | 0 | 3 | 1 | H | H | H | 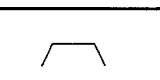 |
TABLE 29
| No. | X | k | m | n | $Z^1$ | $Z^2$ | $Z^3$ | $N\langle{R^3 \atop R^4}$ |
|---|---|---|---|---|---|---|---|---|
| 501 | NAc | 0 | 2 | 1 | H | H | H | 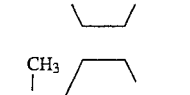 |
| 502 | NH | 0 | 2 | 1 | H | H | H | 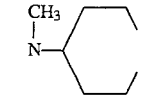 |
| 503 | $NCH_3$ | 0 | 2 | 1 | H | H | H | 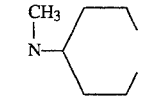 |
| 504 | $NCH_2Ph$ | 0 | 2 | 1 | H | H | H | 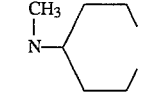 |
| 505 | NH | 0 | 2 | 1 | H | H | H | 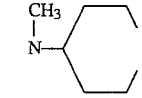 |
| 506 | NAc | 0 | 3 | 1 | H | H | H | 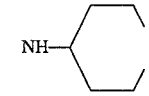 |
| 507 | NH | 0 | 3 | 1 | H | H | H | 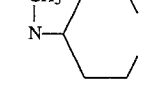 |
| 508 | $NCH_3$ | 0 | 3 | 1 | H | H | H | 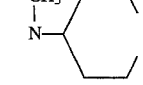 |

TABLE 29-continued

| No. | X | k | m | n | $Z^1$ | $Z^2$ | $Z^3$ | $\begin{array}{c}R^3\\N{<}\\R^4\end{array}$ |
|---|---|---|---|---|---|---|---|---|
| 509 | NCH$_2$Ph | 0 | 3 | 1 | H | H | H | CH$_3$-N-<ring>-N-CH$_2$Ph |
| 510 | NH | 0 | 3 | 1 | H | H | H | NH-<ring>-N-CH$_2$Ph |
| 511 | NAc | 0 | 4 | 1 | H | H | H | CH$_3$-N-<ring>-N-CH$_2$Ph |
| 512 | NH | 0 | 4 | 1 | H | H | H | CH$_3$-N-<ring>-N-CH$_2$Ph |
| 513 | NCH$_3$ | 0 | 4 | 1 | H | H | H | CH$_3$-N-<ring>-N-CH$_2$Ph |
| 514 | NCH$_2$Ph | 0 | 4 | 1 | H | H | H | CH$_3$-N-<ring>-N-CH$_2$Ph |
| 515 | NH | 0 | 4 | 1 | H | H | H | NH-<ring>-N-CH$_2$Ph |
| 516 | NCH$_2$Ph | 1 | 3 | 1 | H | H | H | CH$_3$-N-<ring>-N-CH$_2$Ph |
| 517 | NAc | 1 | 3 | 1 | H | H | H | CH$_3$-N-<ring>-N-CH$_2$Ph |
| 518 | NCH$_3$ | 1 | 3 | 1 | H | H | H | CH$_3$-N-<ring>-N-CH$_2$Ph |
| 519 | NCH$_2$Ph | 1 | 3 | 1 | H | H | H | CH$_3$-N-<ring>-N-CH$_2$Ph |
| 520 | NH | 1 | 3 | 1 | H | H | H | NH-<ring>-N-CH$_2$Ph |

TABLE 30

| No. | X | k | m | n | $Z^1$ | $Z^2$ | $Z^3$ | $N\langle{R^3 \atop R^4}$ |
|---|---|---|---|---|---|---|---|---|
| 521 | NCH$_2$Ph | 0 | 2 | 2 | H | OH | H | N-piperazine-NCH$_2$Ph |
| 522 | NCH$_2$Ph | 0 | 2 | 2 | H | OCH$_3$ | H | N-piperazine-NCH$_2$Ph |
| 523 | NCH$_2$Ph | 0 | 3 | 2 | H | OH | H | N-piperazine-NCH$_2$Ph |
| 524 | NCH$_2$Ph | 0 | 3 | 2 | H | OCH$_3$ | H | N-piperazine-NCH$_2$Ph |
| 525 | NCHO | 0 | 2 | 2 | H | H | H | N-piperazine-NCH$_2$Ph |
| 526 | NCHO | 0 | 3 | 2 | H | H | H | N-piperazine-NCH$_2$Ph |
| 527 | NCH$_2$Ph | 0 | 2 | 2 | H | H | H | N-piperazine-NCH$_2$Ph |
| 528 | NCH$_2$Ph | 0 | 3 | 2 | H | H | H | N-piperazine-NCH$_2$Ph |

TABLE 31

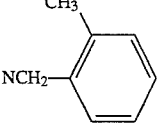

| No. | X | k | m | n | $Z^1$ | $Z^2$ | $Z^3$ | $N\langle{R^3 \atop R^4}$ |
|---|---|---|---|---|---|---|---|---|
| 529 | 2-(CH$_3$),1-(NHCH$_2$)-phenyl | 2 | 2 | 2 | H | H | H | N-piperazine-NCH$_2$Ph |

TABLE 31-continued

| No. | X | k | m | n | $Z^1$ | $Z^2$ | $Z^3$ | $N(R^3)(R^4)$ |
|---|---|---|---|---|---|---|---|---|
| 530 | 3-CH₃, NCH₂ phenyl | 2 | 2 | 2 | H | H | H | N(piperazine)NCH₂Ph |
| 531 | 2-F, NCH₂ phenyl | 2 | 2 | 2 | H | H | H | N(piperazine)NCH₂Ph |
| 532 | 3-F, NCH₂ phenyl | 2 | 2 | 2 | H | H | H | N(piperazine)NCH₂Ph |
| 533 | 3-NH₂, NCH₂ phenyl | 2 | 2 | 2 | H | H | H | N(piperazine)NCH₂Ph |
| 534 | 2-NH₂, NCH₂ phenyl | 2 | 2 | 2 | H | H | H | N(piperazine)NCH₂Ph |
| 535 | 3-OH, NCH₂ phenyl | 2 | 2 | 2 | H | H | H | N(piperazine)NCH₂Ph |
| 536 | 2-OH, NCH₂ phenyl | 2 | 2 | 2 | H | H | H | N(piperazine)NCH₂Ph |
| 537 | 3,4,5-tri-OCH₃, NCH₂ phenyl | 2 | 2 | 2 | H | H | H | N(piperazine)NCH₂Ph |
| 538 | 4-Br, NCH₂ phenyl | 2 | 2 | 2 | H | H | H | N(piperazine)NCH₂Ph |

TABLE 31-continued

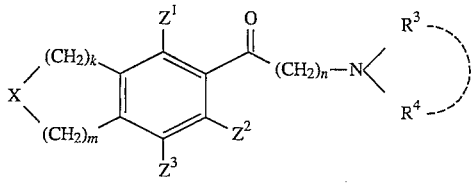

| No. | X | k | m | n | Z¹ | Z² | Z³ | $\begin{array}{c}R^3\\N\\R^4\end{array}$ |
|---|---|---|---|---|---|---|---|---|
| 539 | NCH₂—⟨C₆H₄⟩—C₂H₅ | 2 | 2 | 2 | H | H | H | N(piperazine)NCH₂Ph |
| 540 | NCH₂—⟨C₆H₄⟩—COCH₃ | 2 | 2 | 2 | H | H | H | N(piperazine)NCH₂Ph |
| 541 | NCH₂—⟨C₆H₄⟩—COPh | 2 | 2 | 2 | H | H | H | N(piperazine)NCH₂Ph |
| 542 | NCH₂—⟨C₆H₄⟩—NHAc | 2 | 2 | 2 | H | H | H | N(piperazine)NCH₂Ph |
| 543 | NCH₂—⟨C₆H₄⟩—Ph | 2 | 2 | 2 | H | H | H | N(piperazine)NCH₂Ph |
| 544 | NCH₂—⟨C₆H₄⟩—Ph (meta) | 2 | 2 | 2 | H | H | H | N(piperazine)NCH₂Ph |
| 545 | NCH₂—⟨C₆H₄⟩—OCONHCH₃ | 2 | 2 | 2 | H | H | H | N(piperazine)NCH₂Ph |
| 546 | NCH₂—⟨C₆H₄⟩—OCONHCH₃ (meta) | 2 | 2 | 2 | H | H | H | N(piperazine)NCH₂Ph |

TABLE 32

| No. | X | k | m | n | Z¹ | Z² | Z³ | (N-R³/R⁴ group) |
|---|---|---|---|---|---|---|---|---|
| 547 | 2-(CH₃NHCOO), (NCH₂)-phenyl | 2 | 2 | 2 | H | H | H | N-piperazine-NCH₂Ph |
| 548 | 3-NO₂, (NCH₂)-phenyl | 2 | 2 | 2 | H | H | H | N-piperazine-NCH₂Ph |
| 549 | 2-CH, (NCH₂)-phenyl | 2 | 2 | 2 | H | H | H | N-piperazine-NCH₂Ph |
| 550 | 3-CH, (NCH₂)-phenyl | 2 | 2 | 2 | H | H | H | N-piperazine-NCH₂Ph |
| 551 | 4-CH, (NCH₂)-phenyl | 2 | 2 | 2 | H | H | H | N-piperazine-NCH₂Ph |
| 552 | 3,5-(OCH₃)₂, (NCH₂)-phenyl | 2 | 2 | 2 | H | H | H | N-piperazine-NCH₂Ph |
| 553 | 3-C₂H₅, (NCH₂)-phenyl | 2 | 2 | 2 | H | H | H | N-piperazine-NCH₂Ph |
| 554 | 2-C₂H₅, (NCH₂)-phenyl | 2 | 2 | 2 | H | H | H | N-piperazine-NCH₂Ph |
| 555 | 3-Br, (NCH₂)-phenyl | 2 | 2 | 2 | H | H | H | N-piperazine-NCH₂Ph |
| 556 | 2-Br, (NCH₂)-phenyl | 2 | 2 | 2 | H | H | H | N-piperazine-NCH₂Ph |

TABLE 32-continued
| No. | X | k | m | n | Z¹ | Z² | Z³ | $\begin{matrix}R^3\\N\\R^4\end{matrix}$ |
|-----|---|---|---|---|----|----|----|---|
| 557 | 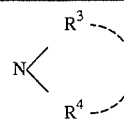 | 2 | 2 | 2 | H | H | H | 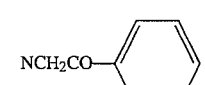 |
| 558 |  | 2 | 2 | 2 | H | H | H | 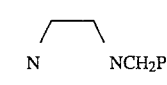 |
| 559 | 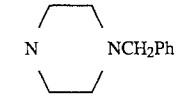 | 2 | 2 | 2 | H | H | H | 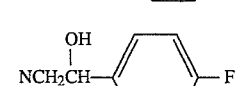 |
| 560 | 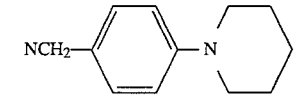 | 2 | 2 | 2 | H | H | H | 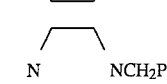 |
| 561 | 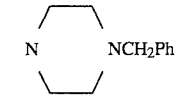 | 2 | 2 | 2 | H | H | H | 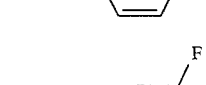 |
| 562 |  | 2 | 2 | 2 | H | H | H | 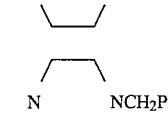 |
| 563 | 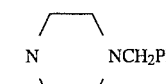 | 2 | 2 | 2 | H | H | H | 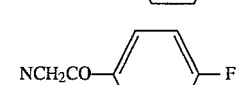 |
| 564 | 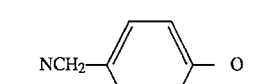 | 2 | 2 | 2 | H | H | H | 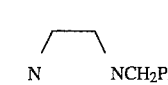 |
| 565 | 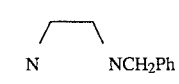 | 2 | 2 | 2 | H | H | H | 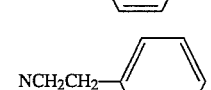 |
| 566 | 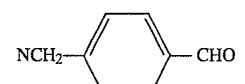 | 2 | 2 | 2 | H | H | H | 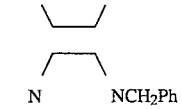 |

TABLE 33

| No. | X | k | m | n | Z¹ | Z² | Z³ | NR³R⁴ |
|---|---|---|---|---|---|---|---|---|
| 567 | NCH₂CH₂-(3,4-diOH-C₆H₃) | 2 | 2 | 2 | H | H | H | piperazinyl-NCH₂Ph |
| 568 | NCH₂CH₂-(3,4-diOCH₃-C₆H₃) | 2 | 2 | 2 | H | H | H | piperazinyl-NCH₂Ph |
| 569 | NCH₂Ph | 2 | 2 | 2 | H | H | H | piperazinyl-NCH₂-(3-CH₃-C₆H₄) |
| 570 | NCH₂Ph | 2 | 2 | 2 | H | H | H | piperazinyl-NCH₂-(2-CH₃-C₆H₄) |
| 571 | NCH₂Ph | 2 | 2 | 2 | H | H | H | piperazinyl-NCH₂-(2-Br-C₆H₄) |
| 572 | NCH₂Ph | 2 | 2 | 2 | H | H | H | piperazinyl-NCH₂-(2-NO₂-C₆H₄) |
| 573 | NCH₂Ph | 2 | 2 | 2 | H | H | H | piperazinyl-NCH₂-(3-N(CH₃)₂-C₆H₄) |
| 574 | NCH₂Ph | 2 | 2 | 2 | H | H | H | piperazinyl-NCH₂-(2-N(CH₃)₂-C₆H₄) |
| 575 | NCH₂Ph | 2 | 2 | 2 | H | H | H | piperazinyl-NCH₂-(4-piperidinyl-C₆H₄) |
| 576 | NCH₂Ph | 2 | 2 | 2 | H | H | H | piperazinyl-NCH₂-(4-pyrrolyl-C₆H₄) |

TABLE 33-continued
| No. | X | k | m | n | $Z^1$ | $Z^2$ | $Z^3$ | $\begin{array}{c}R^3\\ N\\ R^4\end{array}$ |
|---|---|---|---|---|---|---|---|---|
| 577 | NCH$_2$Ph | 2 | 2 | 2 | H | H | H | 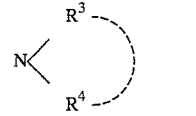 |
| 578 | NCH$_2$Ph | 2 | 2 | 2 | H | H | H | 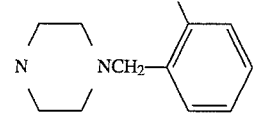 |
| 579 | NCH$_2$Ph | 2 | 2 | 2 | H | H | H | 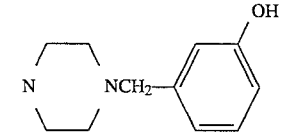 |
| 580 | NCH$_2$Ph | 2 | 2 | 2 | H | H | H | 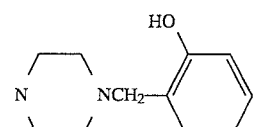 |
| 581 | NCH$_2$Ph | 2 | 2 | 2 | H | H | H | 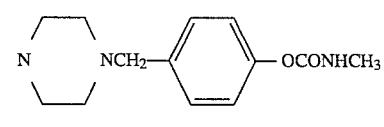 |
| 582 | NCH$_2$Ph | 2 | 2 | 2 | H | H | H | 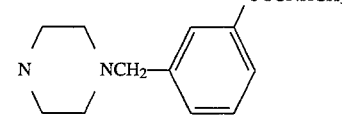 |
| 583 | NCH$_2$Ph | 2 | 2 | 2 | H | H | H | 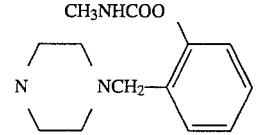 |
| 584 | NCH$_2$Ph | 2 | 2 | 2 | H | H | H | 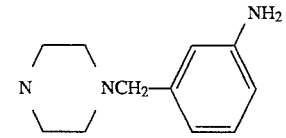 |
| 585 | NCH$_2$Ph | 2 | 2 | 2 | H | H | H | 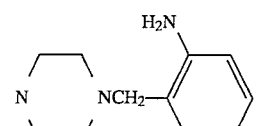 |
| 586 | NCH$_2$Ph | 2 | 2 | 2 | H | H | H | 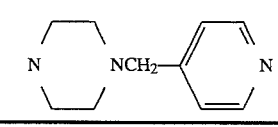 |

TABLE 34
| No. | X | k | m | n | $Z^1$ | $Z^2$ | $Z^3$ | $N{<}^{R^3}_{R^4}$ |
|---|---|---|---|---|---|---|---|---|
| 587 | NCH$_2$Ph | 2 | 2 | 2 | H | H | H | 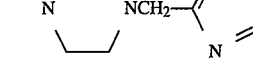 |
| 588 | NCH$_2$Ph | 2 | 2 | 2 | H | H | H | 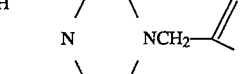 |
| 589 | NCH$_2$Ph | 2 | 2 | 2 | H | OH | H | 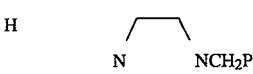 |
| 590 | NCH$_2$Ph | 2 | 2 | 2 | H | OCH$_3$ | H | 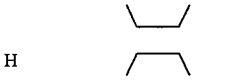 |
| 591 | NCH$_2$Ph | 2 | 2 | 2 | H | Cl | H | 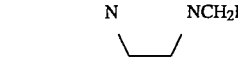 |
| 592 | NCH$_2$Ph | 2 | 2 | 2 | H | Br | H | 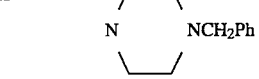 |
| 593 | NCH$_2$Ph | 2 | 2 | 2 | H | CH$_3$ | H | 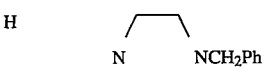 |
| 594 | NCH$_2$Ph | 1 | 3 | 2 | H | OH | H | 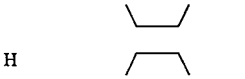 |
| 595 | NCH$_2$Ph | 1 | 3 | 2 | H | OCH$_3$ | H | 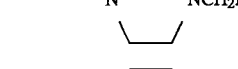 |
| 596 | NCH$_2$Ph | 0 | 3 | 2 | H | OH | H | 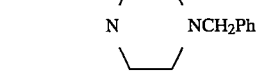 |
| 597 | NCH$_2$Ph | 0 | 3 | 2 | H | OCH$_3$ | H | 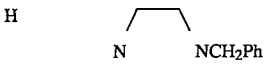 |
| 598 | NCHO | 2 | 1 | 2 | H | H | H | 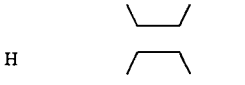 |
| 599 | NCHO | 0 | 3 | 2 | H | H | H | 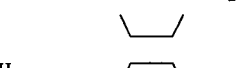 |
| 600 | NCHO | 1 | 3 | 2 | H | H | H | 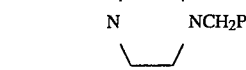 |

TABLE 34-continued

| No. | X | k | m | n | $Z^1$ | $Z^2$ | $Z^3$ | $\begin{array}{c}R^3\\N{<}\\R^4\end{array}$ |
|---|---|---|---|---|---|---|---|---|
| 601 | NCHO | 0 | 4 | 2 | H | H | H | N⟨⟩NCH₂Ph |
| 602 | NCHO | 0 | 5 | 2 | H | H | H | N⟨⟩NCH₂Ph |
| 603 | NCH₂Ph | 2 | 2 | 2 | H | H | H | N⟨⟩NCH₂Ph |
| 604 | NCH₂Ph | 1 | 3 | 2 | H | H | H | N⟨⟩NCH₂Ph |
| 605 | NCH₂Ph | 0 | 3 | 2 | H | H | H | N⟨⟩NCH₂Ph |

In the tables, Ac stands for acetyl group, and Ph stands for phenyl group.

As salts of the compounds [I] and [VII] of this invention, physiologically acceptable acid addition salts are especially preferable. Examples of these salts include salts with inorganic acids (e.g. hydrochloric acid, phosphoric acid, hydrobromic acid, sulfuric acid), and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid). And, in the case where the compounds [I] and [VII] of this invention have an acid group such as —COOH, they may form salts with inorganic bases (e.g. an alkali metal or alkaline earth metal such as sodium, potassium, calcium, magnesium etc., ammonia) or organic bases (e.g. tri—$C_{1-3}$ alkylamine such as triethylamine, etc.).

In the following, the process of producing the compound [I] or its salts of the present invention is described.

While the following description applies not only to the production of the compound [I] per se but also to the production of its salts, these compounds are simply referred to as the compound [I] inclusively in the description.

The compound [I] can be produced by, for example, reacting a compound represented by the formula:

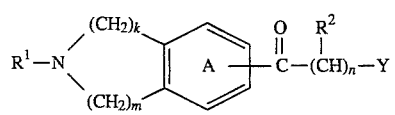 [II]

wherein each symbol has the same meaning as defined above, or a salt thereof, with a compound represented by the formula:

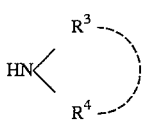 [III]

wherein each symbol has the same meaning as defined above or a salt thereof.

As the leaving group shown by Y in the formula [II], use is made of, for example, halogen atoms (e.g. chlorine, bromine, iodine, etc.), $C_{1-6}$ alkylsulfonyloxy group (e.g. methanesulfonyloxy, ethanesulfonyloxy, etc.), $C_{6-10}$ arylsulfonyloxy (e.g. benzenesulfonyloxy, p-toluenesulfonyloxy, etc.), etc. among them, halogen atoms are preferable, more specifically, chlorine, bromine, etc.

As salts of the compound [II] and [III], use is made of, for example, salts with inorganic acids (e.g. hydrochloric acid, phosphoric acid, hydrobromic acid, sulfuric acid) or those with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid). And, in the case where the compounds [II] and [III] of this invention have an acid group such as —COOH, they may form salts with inorganic bases (e.g. an alkali metal or alkaline earth metal such as sodium, potassium, calcium, magnesium, etc., ammonia) or organic bases (e.g. tri—$C_{1-3}$ alkylamine such as triethylamine, etc.).

The amount of the compound [III] or a salt thereof to be employed in this reaction ranges, usually, from 1.0 to 50.0 mol., preferably 1.0 to 10.0 mol., relative to one mol. of the compound [II] or a salt thereof. This reaction can be conducted at temperatures ranging from 0° C to 120° C. The reaction time ranges, usually, from 10 minutes to 48 hours, preferably from 2 to 16 hours.

While this reaction can be conducted in the absence of solvent, it can be conducted, upon necessity, in a solvent. As the solvent, any one can be employed unless it hampers the reaction, exemplified by lower alcohols such as methanol, ethanol, propanol, isopropanol, n-butanol, t-butanol, etc., ethers such as dioxane, ether, tetrahydrofuran, etc., aromatic hydrocarbons such as toluene, benzene, xylene, etc., amides such as dimethylformamide, dimethylacetamide, hexamethylphosphonotriamide, etc., esters such as ethyl acetate, butyl acetate, etc. The amount the solvent to be employed ranges, usually, from 0.5 to 100 ml, preferably from 5 to 20 ml, relative to 1 mmol. of the compound [II] or salt thereof.

This reaction can also be conducted in the presence of a base, when necessary. Examples of the base to be employed include inorganic bases such as sodium carbonate, potassium carbonate, lithium carbonate, sodium hydroxide, potassium hydroxide, sodium methoxide, sodium ethoxide, sodium hydride, etc. and organic bases such as pyridine, 4-dimethylaminopyridine, triethylamine, etc. The amount of the base to+be employed ranges, usually, from equimol. to excess amount, preferably from 1.0 to 5.0 mol. relative to one mol. of the compound [III] or a salt thereof.

It is also possible to promote this reaction by allowing an iodide (e.g. sodium iodide, potassium iodide, lithium iodide) to be present in the reaction system. The amount of the iodide to be employed ranges, usually from 1 to 5 mol., preferably 1.0 to 1.5 mol., relative to one mol. of the compound [II] or a salt thereof.

The compound [I], wherein $R^1$ stands for an optionally substituted hydrocarbon group or an optionally substituted acyl group, or a salt thereof can be produced by, for example, reacting a compound [I], wherein $R^1$ stands for H (R=H), or a salt thereof, with a compound represented by the formula $$R^{1'}-Y^2 \quad [VIII]$$

wherein $R^{1'}$ stands for an optionally substituted hydrocarbon group or an optionally substituted acyl group, and $Y^2$ stands for a leaving group, or a salt thereof.

Examples of the salts of the compound [VIII] include those with inorganic acids (e.g. hydrochloric acid, phosphoric acid, hydrobromic acid, sulfuric acid) or organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid). Further, in the case where the compound [VIII] of this invention has an acid group such as —COOH, the compound [VIII] may be in the form of salt with an inorganic base (e.g. an alkali metal or alkaline earth metal such as sodium, potassium, calcium, magnesium, etc., ammonia) or an organic base (e.g. tri—$C_{1-3}$ alkylamine such as triethylamine, etc.).

As the leaving group shown by $Y^2$, use is made of, for example, a halogen atom (e.g. chlorine, bromine, iodine), $C_{1-6}$ alkylsulfonyloxy group (e.g. methanesulfonyloxy, ethanesulfonyloxy), $C_{6-10}$ arylsulfonyloxy group (e.g. benzenesulfonyloxy, p-toluenesulfonyloxy), etc. Especially, halogen atoms are preferable.

As the optionally substituted hydrocarbon groups shown by $R^{1'}$, use is made of, for example, the optionally substituted hydrocarbon groups shown by $R^1$ as described in the foregoing. As the optionally substituted acyl groups shown by $R^{1'}$, use is made of, for example, the optionally substituted acyl groups shown by $R^1$ as described in the foregoing.

Further, the compound [I] (R=H) or a salt thereof can be produced also by subjecting a compound [I], wherein $R^1$ stands for an optionally substituted acyl group, or a salt thereof to hydrolysis with an acid or a base, in the same manner as in conventional hydrolysis.

The starting compound [II] or a salt thereof can be produced by reacting a compound represented by the formula:

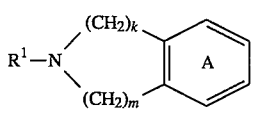

wherein each symbol has the same meaning as defined above, or a salt thereof, with a compound represented by the formula:

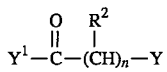

wherein $Y^1$ stands for a leaving group, and other symbols are of the same meanings as defined above.

As salts of the compound [IX], use is made of, for example, salts with an inorganic acid (e.g. hydrochloric acid, phosphoric acid, hydrobromic acid, sulfuric acid) or an organic acid (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid). Further, in the case where the compound [IX] of this invention has an acid group such as —COOH, the compound [IX] may be in the form of a salt with an inorganic base (e.g. an alkali metal or an alkaline earth metal such as sodium, potassium, calcium, magnesium, etc., ammonia) or an organic base (e.g. tri—$C_{1-3}$ alkylamine such as triethylamine, etc.).

As the leaving group shown by $Y^1$, use is made of, for example, halogen atoms (e.g. chlorine, bromine, iodine), $C_{1-6}$ alkylsulfonyloxy group (e.g. methanesulfonyloxy, ethanesulfonyloxy), $C_{6-10}$ arylsulfonyloxy group (e.g. benzenesulfonyloxy, p-toluenesulfonyloxy), etc. Especially, halogen atoms are preferable.

The compound [IX] or salts thereof can be produced in accordance with a per se known method or a method analogous thereto, for example, as described in J. Org. Chem. 34, 2235 (1969), J. Org Chem. 54, 5574 (1989), Tetrahedron Lett. 35, 3023 (1977), and Bull. Chem. Soc. Jpn. 56, 2300 (1983).

The compound [X] can be produced by a per se known method or a method analogous thereto.

The reaction of the compound [IX] or a salt thereof with the compound [X] can be conducted by using, for example, usually about 1 to 20 mol., preferably about 1 to 5 mol., of the compound [X] or a salt thereof relative to 1 mol. of the compound [IX], in the presence of, for example, a Lewis acid.

This reaction can be conducted without using a solvent or, upon necessity, in a solvent. As the solvent, any one which is conventionally usable in chemical reactions, unless it hampers the reaction, can be employed, as exemplified by organic solvents including hydrocarbons (e.g. pentane, hexane, benzene, toluene, nitrobenzene, etc.), halogenated hydrocarbons (e.g. dichloromethane, chloroform, 1,2-dichloroethane, carbon tetrachloride, etc.), ethers (e.g. ethyl ether, tetrahydrofuran, dioxane, dimethoxyethane, etc.), nitro alkanes (e.g. nitromethane, propionitrile, etc.), and carbon disulfide. Especially, dichloromethane, 1,2-dichloroethane, nitrobenzene and carbon disulfide are preferable. The amount of the solvent ranges usually from 0.5 to 100 ml, preferably from 5 to 20 ml, relative to 1 mmol. of the compound [IX] or a salt thereof.

The reaction temperature ranges usually from from about –30° C. to about 150° C., preferably from about 20° C. to about 100° C. The reaction time ranges usually from 0.5 to 72 hours, preferably from 1 to 16 hours.

And, as the Lewis acid to be employed in this reaction, use is made of, for example, aluminum chloride, zinc chloride, titanium chloride, tin(IV) chloride, boron trifluoride, iron(II) chloride, iron(III) chloride, antimony pentachloride (V), bismuth chloride (III), silver chloride (II), hydrogen fluoride, sulfuric acid, polyphosphoric acid, etc. Among them, aluminum chloride and the like are preferable. The amount of the Lewis acid to be employed ranges usually from 1 to 10 mol., preferably from 2 to 10 mol., relative to 1 mol. of the compound [IX] or a salt thereof.

In the above reaction, the position where the group of the compound [X]

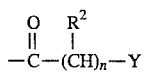

is introduced into the compound [IX] or a salt thereof may be any of the positions on ring A on which the substitution can take place. For example, in the case where the skeleton of the compound [IX] or a salt thereof is 1,2,3,4-tetrahydroquinoline (provided that the ring A is unsubstituted), the group of the compound [X] is introduced principally into 6-position, while such compounds as having the group introduced at any other positions (5-position, 7-position, 8-position) can be produced and separated as well.

The compound [II] or salts thereof obtained thus above can be isolated and refined by a conventional means such as concentration, pH change, phasic transfer, solvent extraction, fractional distillation, distillation, crystallization, recrystallization and chromatography, while they may be fed to the subsequent process as the material in the state of reaction mixture without isolation.

The starting compound [III] or salts thereof can be produced by a per se known method or a method analogous thereto.

The compound [VIII] or salts thereof can be produced by a per se known method or a method analogous thereto.

And, among the compounds [I], those where n is 2, i.e. the compound of the formula:

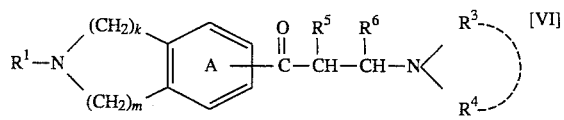

wherein each symbol is of the same meaning as defined above, or a salt thereof, can be produced also by reacting a compound of the formula:

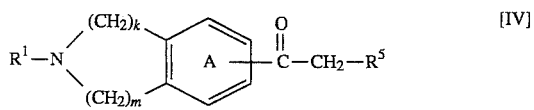

wherein each symbol is of the same meaning as defined above, or a salt thereof, with a compound represented by the formula:

$R^6$—CHO [V]

wherein $R^6$ is of the same meaning as defined above and a compound represented by the formula:

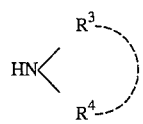

wherein each symbol is of the same meaning as defined above, or a salt thereof.

As salts of the compound [IV], use is made of, for example, those with inorganic acids (e.g. hydrochloric acid, phosphoric acid, hydrobromic acid, sulfuric acid) or with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid). Further, in the case where the compound [IV] of this invention has an acid group such as —COOH, compound [IV] may be in the form of a salt with an inorganic base (e.g. alkali metal or alkaline earth metal such as sodium, potassium, calcium, magnesium, etc., ammonia) or with an organic base (e.g. tri-$C_{1-3}$ alkylamine such as triethylamine, etc.).

This reaction can be conducted in substantially the same manner as the Mannich reaction described in Organic Reaction, Vol. 1, p 303 to 341. More specifically, this reaction is conducted by reacting, for example, compound [V] and the compound [III] or a salt thereof, with the compound [IV] or a salt thereof in a ratio of usually 0.9 to 10, preferably 1.0 to 3.0, equivalents of the former relative to 1 equivalent of the latter. Wile this reaction can be carried out usually at temperatures ranging from room temperature to under heating (10 to 150° C.), it is conducted preferably at temperatures ranging from 80 to 120° C. The action time ranges usually from 1 to 48 hours, preferably from 2 to 24 hours. This reaction can usually be conducted in the absence or presence of solvent. As the solvent, any one to be used in general for Mannich reaction can be employed, unless it hampers this reaction. For example, alcohols such as ethanol are often employed. The amount of the solvent ranges usually from 0.5 to 200 ml, preferably from 5 to 40 ml, relative to 1 mmol. of the compound [IV] or a salt thereof. Further, this reaction can be conducted, when desired, in the presence of an inorganic acid such as hydrochloric acid. The acid is used in a catalytic amount relative to the compound [.IV] or a salt thereof (0.001 to 0.05 equivalent relative to 1 equivalent of the compound [IV] or a salt thereof). In the case where the compound [III] or [IV] to be employed for the reaction is not in the form of salt, however, it is preferable to use the acid in an excess amount sufficient for allowing these compounds to form salts.

The compound [IV] or salts thereof and the compound [V] can be produced by a per se known method or a method analogous thereto.

Further, the compound [I] or a salt thereof can be produced also by first hydrolizing the ester moiety (COOR²) of, for example, a compound represented by the formula:

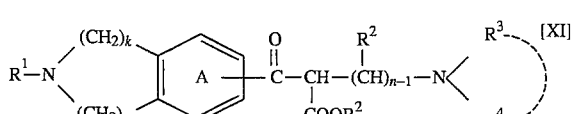

wherein each symbol is of the same meaning as defined above or a salt thereof, which can be obtained by the method described above, then by subjecting the reaction mixture to decarboxylation. The hydrolysis and decarboxylation can be conducted in the same manner as per se known methods.

And, the compound [I] or a salt thereof can be produced also by subjecting, for example, a compound, wherein $R^1$ is carboxylic acid acyl, or a salt thereof to reduction in a conventional manner. In this reaction, it is preferable that, upon necessity, the functional group (e.g. ketone) of the compound [I] or a salt thereof ($R^1$= carboxylic acid acyl group) is first protected, in the form of acetal with, for example, ethylene glycol or any other alcohol (e.g. methanol, ethanol, etc.), then the thus protected compound is subjected to reduction, and then the reaction mixture is subjected to deprotection with an acid or base or by heating.

And, in each of the above-mentioned reactions, in the case where the starting compound has, as substituents, amino group, carboxyl group, hydroxyl group, etc., these groups may be protected with such protecting groups as generally used in peptide chemistry, and the object compound can be obtained by, upon necessity, removing these protecting groups after the reaction.

As the protecting groups of amino group, use is made of, for example, formyl, optionally substituted $C_{1-6}$ alkyl-carbonyl groups (e.g. acetyl, ethylcarbonyl, etc.), benzoyl, $C_{1-6}$ alkyloxy-carbonyl (e.g. methoxycarbonyl, ethoxycarbonyl, etc.), phenyloxycarbonyl (e.g. phenoxycarbonyl, etc.), $C_{7-15}$ aralkyloxy-carbonyl (e.g. benzyloxycarbonyl, fluorenyloxycarbonyl, etc.), trityl, phthaloyl, etc. As substituents on these groups, use is made of halogen atoms (e.g. fluorine, chlorine, bromine, iodine, etc.), $C_{1-6}$ alkyl-carbonyl (e.g. methylcarbonyl, ethylcarbonyl, butylcarbonyl, etc.), nitro group, among others, and the number of these substituents ranges from 1 to 3. As the protecting group of carboxyl group, use is made of, for example, an optionally substituted $C_{1-6}$ alkyl (e.g. methyl, ethyl, n-propyl, i-propyl, n-butyl, tert-butyl, etc.), phenyl, trityl, silyl, etc. As substituents on these groups, use is made of halogen atoms (e.g. fluorine, chlorine, bromine, iodine, etc.), formyl, $C_{1-6}$ alkyl carbonyl (e.g. methylcarbonyl, ethylcarbonyl, butylcarbonyl, etc.), nitro, etc., and the number of these substituents ranges from 1 to 3. As the group protecting hydroxyl group, use is made of, for example, an optionally substituted $C_{1-6}$ alkyl (e.g. methyl, ethyl, n-propyl, i-propyl, n-butyl, tert-butyl, etc.), phenyl, $C_{7-10}$ aralkyl (e.g. benzyl, etc.), formyl, $C_{1-6}$ alkyl carbonyl (e.g. acetyl, ethylcarbonyl, etc.), phenyloxycarbonyl, $C_{7-10}$ aralkyl-carbonyl (e.g. benzyloxycarbonyl, etc.), pyranyl, furanyl, silyl, etc. As substituents on these groups, use is made of halogen atom (e.g. fluorine, chlorine, bromine, iodine, etc.), $C_{1-6}$ alkyl, phenyl, $C_{7-10}$ aralkyl, nitro group, etc., and the number of these substituents ranges from 1 to 4.

And, as the means of removing these protecting groups, use is made of .per se known means or those analogous thereto, as exemplified by those which comprise processing with an acid, a base, reduction, UV-ray, hydrazine, phenyl hydrazine, sodium N-methyldithiocarbamate, tetrabutylammonium fluoride, palladium acetate, etc.

Further, the compound [VII] of this invention or salts thereof can be produced by substantially the same method as described above for the production of the compound [I] or salts thereof, using a compound wherein the group

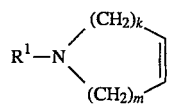

in, for example, the starting compound [III], [IV], [IX] or a salt thereof, is a group

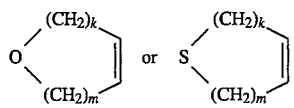

The compound [I] or salts thereof and the compound [VII] or salts thereof thus obtained above can be isolated and refined by conventional separating means such as recrystallization, distillation, chromatography, etc. In the case where the compound [I] and the compound [VII] thus obtained above are in the free form, they can be converted to salts by per se conventional means or those analogous thereto. Conversely, when the compound [I] or [VII] is obtained in the form of salt, it can be converted to the free compound or any other salt by per se conventional means or those analogous thereto.

The compound [I] or salts thereof and the compound [VII] or salts thereof include their stereoisomers due to the presence of asymmetric carbon atoms. These isomers can be resolved into corresponding optically active compounds by means of a conventional optical resolution.

The compound [I] or salts thereof and the compound [VII] or salts thereof of the present invention act on the central nervous system of mammals, have strong cholinesterase inhibitory activity, and exhibit excellent antiamnestic effects on various amnesia-inducing actions in man and animals (e.g. mice, etc.). Further, the compound [I] or salts thereof and the compound [VII] or salts thereof of the present invention have monoamine (e.g. norepinephrine, serotonin, etc.) reuptake inhibitory activity, and exhibit excellent antidepressant activity, etc. in man and animals (e.g. mice, etc.).

The compound [I] or salts thereof and the compound [VII] or salts thereof of the present invention are remarkably excellent in separation of effects on central nervous system from those on peripheral nervous system, as compared with physostigmine and, at the antiamnestic and antidepressant dose level, do not cause peripheral nervous system effects such as spasm, salivation, diarrhea, etc. or, if they do, only slightly. Moreover, they are characterized by a long duration of effects and low toxicity, ensuring a remarkably high efficacy when administered orally. The acute toxicity of the compound [I] or salts thereof and the compound [VII] or salts thereof of the present invention is not less than 100 mg/kg. Therefore, the compounds of this invention are useful as a safely administrable agent for improving the cerebral function of mammalian animals including human beings.

Diseases on which the compounds of this invention are effective include senile dementia, Alzheimer's diseases, Huntington's chorea, hyperkinesia and mania. The compounds of this invention can be used for the prophylaxis or therapy of these diseases. Further, the compounds of this invention can be also used for the prophylaxis or therapy of depression, hypobulia, affective disorders, lack of spontaneity, etc. which are symptoms related to the above-mentioned diseases.

The compounds of this invention are usually formulated with pharmaceutically acceptable carriers or excipients, which can be administered orally or non-orally to man and other mammalian animals. Such pharmaceutical preparations may be those for oral administration (e.g. powders, tablets, granules and capsules) and for non-oral administration (e.g. suppositories, injections). These pharmaceutical compositions can be prepared by Der se known methods. While the dosage depends on the type and symptom of diseases to be treated, in the case of oral administration to general adult humans (60 kg body weight), it ranges from about 0.01 mg to about 50 mg, preferably from 0.1 to 30 mg, more preferably from 0.5 to 10 mg per day.

By the following working examples, reference examples, formulation examples and experimental examples, the present invention will be illustrated in more concrete manner, but they should by no means be construed as defining the metes and bounds of this invention.

In the experimental examples and reference examples, elution in the procedure of column chromatography was carried out under observation by means of TLC (Thin Layer Chromatography) unless otherwise specified. In the TLC observation, 60F$_{254}$ manufactured by Merck was employed as the TLC plate, the solvent employed as elution solvent for the column chromatography was employed as the developer, and a UV detector was employed for detection. As an adjunctive detection procedure, the spot on the TLC plate was sprayed with 48% HBr, heated to hydrolize, sprayed with a ninhydrin reagent and heated again, then the change to a red—reddish purple was regarded as positive reaction. The fractions containing the object compound were pooled. Unless otherwise specified, Merck Kieselgel 60 (70 to 230 mesh) was employed as the silica gel for the column.

Incidentally, the term "ambient temperature" or "room temperature" generally means usually temperatures ranging from about 5° C. to 40° C., and the term "atmospheric pressure" means the neighborhood of one atmospheric pressure.

And, unless otherwise specified, % denotes percentage by weight.

REFERENCE EXAMPLE 1

4-Chloro-1-(3-acetyl-2,3,4,5-tetrahydro-1H-3-benzazepin- 7-yl)-1-butanone

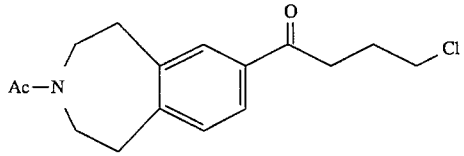

In 30 ml of dichloromethane, was dissolved 3.79 g of 3-acetyl-2,3,4,5-tetrahydro-1H-3-benzazepine. To the solution were added 3.38 g of 4-chlorobutyryl chloride and 4.00 g of aluminum chloride. The mixture was stirred for 2 hours at room temperature (about 20° C.). The reaction mixture was poured into 50 ml of ice-water. The organic layer was separated, which was washed successively with 50 ml of 0.5N aqueous solution of sodium hydroxide and 50 ml of pure water, then dried over anhydrous sodium sulfate. The solvent was distilled off to leave 5.40 g of an oily residue. The residue was purified by means of a silica gel column chromatography (developing solvent, ethyl acetate-dichloromethane 1:1 (V/V)) to afford 2.92 g of the title compound as colorless crystals, m.p.103°–106° C.
Elemental Analysis for C$_{16}$H$_{20}$ClNO$_2$:
Calcd.: C, 65.41; H, 6.86; N, 4.77
Found : C, 65.33; H, 6.91; N, 4.69

REFERENCE EXAMPLE 2

By conducting substantially the same procedure as in Reference Example 1, compounds shown in Table 35 were obtained.

TABLE 35

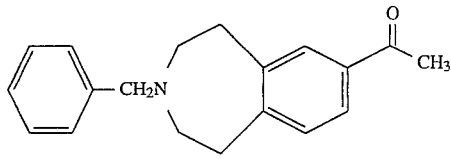

| Compound No. | n | m.p. (°C.) | Molecular Formula | Elemental Analysis Calcd. (Found) | | |
|---|---|---|---|---|---|---|
| | | | | C | H | N |
| 1 | 1 | 128–130 | C$_{14}$H$_{16}$ClNO$_2$ | 63.28 (63.09 | 6.07 6.12 | 5.27 5.26) |
| 2 | 2 | 123–124 | C$_{15}$H$_{18}$ClNO$_2$ | 64.40 (64.33 | 6.48 6.47 | 5.01 4.94) |

REFERENCE EXAMPLE 3

7-Acetyl-3-(phenylmethyl)-2,3,4,5-tetrahydro-1H-3-benzazepine

To 7.36 g of 2,3,4,5-tetrahydro-1H-3-benzazepine and 10.37 g of potassium carbonate, was added 75 ml of ethanol. To the mixture, was added dropwise 8.38 g of benzyl bromide under ice-cooling in the course of 10 minutes, followed by stirring for 2 hours at 25° C., then the solvent was distilled off. To the residue were added 100 ml of pure water and 100 ml of dichloromethane, then the organic layer was separated and dried over sodium sulfate, followed by distilling off the solvent to leave a crystalline residue.

The residue was dissolved in 20 ml of methanol, to which was added 19 ml of 4N methanolic hydrochloric acid. Methanol was then distilled off, and the residue was suspended in 100 ml of ethyl acetate. Resulting crystals were collected by filtration, then the crystals were washed with 30 ml of ethyl acetate. The crystals were dried under reduced pressure to give 11.94 g of 3-(phenylmethyl)-2,3,4,5-tetrahydro-1H-3-benzazepine hydrochloride.

10.95 g of the above-mentioned compound was dissolved in 80 ml of 1,2-dichloroethane, to which were added 10.67 g of aluminum chloride and 4.71 g of acetyl chloride, then the mixture was stirred for 30 minutes under reflux. The reaction mixture was poured into 150 ml of ice-water, then pH of the aqueous layer was adjusted to 10, followed by addition of 150 ml of dichloromethane. The organic layer was separated and dried over sodium sulfate. The solvent was then distilled off to leave 13.0 g of an oily residue. The residue was purified by means of a silica gel column chromatography (developing solvent, ethyl acetate-dichloromethane 1:2) to afford 10.44 g of the title compound as colorless crystals, m.p.89°–91° C.

Elemental Analysis for $C_{19}H_{21}NO$:
  Calcd.: C, 81.68; H, 7.58; N, 5.01
  Found : C, 81.49; H, 7.61; N, 4.86

REFERENCE EXAMPLE 4

Ethyl β-(1-acetyl-2,3,4,5-tetrahydro-1H-1-benzazepin-8-yl)-β-oxopropionate

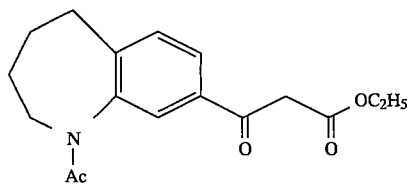

(1) To a solution of 18.9 g of 1-acetyl-2,3,4,5-tetrahydro-1H-1-benzazepine in 20 ml of carbon disulfide were first added 30.8 g of aluminum chloride then 7.8 ml of acetyl chloride gradually at room temperature. The mixture was heated for 16 hours under reflux. The reaction mixture was poured into ice water, which was subjected to extraction with dichloromethane. The extract solution was dried over anhydrous sodium sulfate, then the solvent was distilled off. The residue was purified by means of chromatography (developing solvent; dichloromethane ethyl acetate= 5:1(V/V)) to give 13.5 g of pale yellow crystals. Recrystallization from diethyl ether-hexane affords 12.4 g of 1,8-diacetyl-2,3,4,5-tetrahydro- 1H-1-benzazepine as colorless crystals, m.p.105°–108° C.

Elemental Analysis for $C_{14}H_{17}NO_2$:
  Calcd.: C, 72.70; H, 7.41; N, 6.06
  Found : C, 72.82; H, 7.36; N, 6.00

(2) To a refluxed solution of 3.83 g of diethyl carbonate and 1.04 g of sodium hydride (oil free) in 50 ml of tetrahydrofuran was added dropwise, under nitrogen atmosphere, a solution of 5 g of 1,8-diacetyl- 2,3,4,5-tetrahydro-1H-1-benzazepine in 50 ml of tetrahydrofuran. The mixture was heated for 3 hours under reflux, then the reaction mixture was poured into ice-water, which was subjected to extraction with dichloromethane. The extract solution was dried over anhydrous sodium sulfate, then the solvent was distilled off. The residue was purified by means of chromatography (developing solvent; dichloromethane-ethyl acetate= 5:1(V/V)) to afford 3.5 g of the title compound as a colorless oily product.

Elemental Analysis for $C_{17}H_{21}NO_4$:
  Calcd.: C, 67.31; H, 6.98; N, 4.62
  Found : C, 67.14; H, 6.83; N, 4.63

REFERENCE EXAMPLE 5

By substantially the same procedure as in Reference Example 1, compounds listed in Table 36 were obtained.

TABLE 36

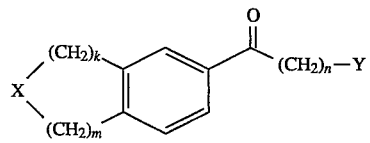

| Compound No. | X | k | m | n | Y | m.p. (°C.) | Molecular Formula | Elemental Analysis Calcd. (Found) | | |
|---|---|---|---|---|---|---|---|---|---|---|
| | | | | | | | | C | H | N |
| 1 | NAc | 0 | 4 | 1 | Cl | 112–115 | $C_{14}H_{16}ClNO_2$ | 63.28 (63.11) | 6.07 (6.14) | 5.27 (5.33) |
| 2 | NAc | 0 | 4 | 2 | Cl | 123–124 | $C_{15}H_{18}ClNO_2$ | 64.40 (64.35) | 6.49 (6.56) | 5.01 (4.91) |
| 3 | $NCO_2Et$ | 0 | 4 | 2 | Cl | oil | $C_{16}H_{20}ClNO_3$ | 62.03 (62.19) | 6.51 (6.40) | 4.52 (4.50) |
| 4 | $NCH_2Ph$ | 2 | 2 | 1 | Cl | 111–113 | $C_{19}H_{20}ClNO$ | 72.72 (72.50) | 6.42 (6.45) | 4.46 (4.44) |
| 5 | $NCH_2Ph$ | 2 | 2 | 2 | Cl | 176–178 | $C_{20}H_{22}ClNO \cdot HCl$ | 65.94 (65.67) | 6.36 (6.52) | 3.84 (3.77) |
| 6 | $NCH_2Ph$ | 2 | 2 | 5 | Br | oil | $C_{23}H_{28}BrNO$ | 66.67 (66.57) | 6.81 (6.83) | 3.38 (3.37) |
| *7 | NCHO | 2 | 0 | 2 | Cl | 134–136 | $C_{12}H_{12}ClNO_2$ | 60.64 (60.45) | 5.09 (4.88) | 5.89 (5.67) |
| 8 | NCHO | 1 | 3 | 2 | Cl | 94–96 | $C_{14}H_{16}ClNO_2$ | 63.28 (63.37) | 6.07 (6.14) | 5.27 (5.23) |
| 9 | NCHO | 2 | 2 | 2 | Cl | 121–123 | $C_{14}H_{16}ClNO_2$ | 63.28 (63.17) | 6.07 (6.02) | 5.27 (5.31) |
| 10 | NAc | 2 | 2 | 4 | Cl | 95–98 | $C_{17}H_{22}ClNO_2$ | 66.33 (66.35) | 7.20 (7.11) | 4.55 (4.60) |
| 11 | $NCO_2CH_3$ | 2 | 2 | 2 | Cl | 117–120 | $C_{15}H_{18}ClNO_3$ | 60.92 (60.97) | 6.13 (6.10) | 4.74 (4.77) |
| *12 | NCHO | 3 | 0 | 2 | Cl | 103–105 | $C_{13}H_{14}ClNO_2$ | 62.03 (62.15) | 5.61 (5.59) | 5.56 (5.70) |
| 13 | NCHO | 0 | 3 | 2 | Cl | oil | $C_{13}H_{14}ClNO_2$ | 62.03 (62.20) | 5.61 (5.60) | 5.56 (5.51) |
| 14 | NCHO | 0 | 5 | 2 | Cl | 118–120 | $C_{15}H_{18}ClNO_2$ | 64.40 (64.48) | 6.48 (6.43) | 5.01 (5.14) |
| *15 | NAc | 3 | 0 | 2 | Cl | 75–77 | $C_{14}H_{16}ClNO_2$ | 63.28 | 6.07 | 5.27 |

TABLE 36-continued

| Compound No. | X | k | m | n | Y | m.p. (°C.) | Molecular Formula | Elemental Analysis Calcd. (Found) | | |
|---|---|---|---|---|---|---|---|---|---|---|
| | | | | | | | | C | H | N |
| 16 | NAc | 0 | 5 | 2 | Cl | oil | $C_{16}H_{20}ClNO_2$ | (63.20 65.41 (65.48 | 6.04 6.86 6.82 | 5.26) 4.77 4.68) |

*$X(CH_2)_k(CH_2)_{mO(CH_2)_n}$—Y

REFERENCE EXAMPLE 6

1-(3-Methyl-2,3,4,5-tetrahydro-1H-3-benzazepin-7-yl)2-propen-1-one hydrochloride

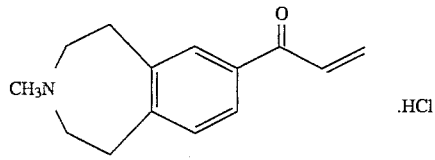

In 30 ml of 1,2-dichloroethane, was dissolved 1.28 g of 3-methyl-2,3,4,5-tetrahydro-1H-3-benzazepine hydrochloride. To the solution were added, at room temperature, 2.1 g of aluminum chloride and 0.66 ml of 3-chloropropionyl chloride, then the mixture was stirred for 2 hours. The reaction mixture was poured into 50 ml of ice-water, then the pH of the aqueous solution was adjusted to not lower than 9 with a 40% aqueous solution of sodium hdyroxide, followed by extraction with 50 ml of dichloromethane. The organic layer was washed with 50 ml of pure water, which was then dried over anhydrous sodium sulfate. The solvent was distilled off under reduced pressure to give an oily residue, which was crystallized from dichloromethane-ether to afford 0.83 g of the title compound as pale yellow crystals, m.p.120°–123° C.

Elemental Analysis for $C_{14}H_{17}NO \cdot HCl \cdot H_2O$:
Calcd.: C, 62.33; H, 7.47; N, 5.19
Found: C, 62.53; H, 7.65; N, 5.13

REFERENCE EXAMPLE 7

By substantially the same procedure as in Reference Example 1, the compounds shown in Table 37 were obtained.

TABLE 37

| Compound No. | X | k | m | $R^2$ | m. p. (°C.) | Molecular Formula | Elemental Analysis Calcd. (Found) | | |
|---|---|---|---|---|---|---|---|---|---|
| | | | | | | | C | H | N |
| 1 | NCHO | 2 | 2 | Ph | 140–142 | $C_{19}H_{19}NO_2$ | 77.79 (77.51 | 6.53 6.43 | 4.77 4.89) |
| 2 | $NCH_2Ph$ | 2 | 2 | Ph | oil | $C_{25}H_{25}NO$ | 84.47 (84.61 | 7.09 7.01 | 4.50 4.50) |

REFERENCE EXAMPLE 8

4-Bromo-1-(3-formyl-2,3,4,5-tetrahydro-1H-3-benzazepin- 7-yl)-2-phenyl-1-butanone

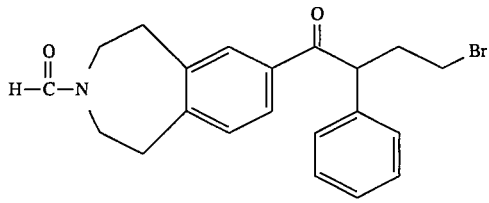

In 50 ml of dimethylformamide was dissolved 2.93 g of the compound No.1 obtained in Reference Example 7, to which was added 0.29 g of 60% sodium hydride. The mixture was stirred for 30 minutes at room temperature, to which was added 4.33 ml of 1,2-dibromoethane, then the mixture was stirred for further 5 hours. The reaction mixture was poured into 150 ml of pure water, which was subjected to extraction with 150 ml of ethyl acetate. The organic layer was washed twice with 150 ml each portion of a saturated aqueous saline solution, which was dried over sodium sulfate, followed by distilling off the solvent under reduced pressure to leave an oily residue. The oily residue was subjected to a silica gel (150 g) column chromatography, eluting with dichloromethane-ethyl acetate (4:1), to afford 1.05 g of the title compound as a colorless oily product.
Elemental Analysis for $C_{21}H_{22}BrNO_2$:
  Calcd.: C, 63.01; H, 5.54; N, 3.50
  Found : C, 63.07; H, 5.62; N, 3.53

REFERENCE EXAMPLE 9

Using the compound obtained in Reference Example 7, substantially the same procedure as in Reference Example 8 was followed to give the compound shown in Table 38.

WORKING EXAMPLE 1

1-(3-Acetyl-2,3,4,5-tetrahydro-1H-3-benzazepin-7-yl)-4-(piperidin- 1-yl)-1-butanone To a solution of 2.64 g of the compound obtained in Reference Example 1 in 50 ml of toluene, were added 1.50 g of piperidine and 20 mg of KI. The mixture was stirred for 12 hours under reflux. The reaction mixture was cooled, to which was then added 50 ml of pure water. The organic layer was separated, from which the solvent was distilled off to leave an oily residue. The residue was purified by means of alumina chromatography (developing solvent; ethyl acetate) to afford 2.15 g of the title compound as colorless powder.
Elemental Analysis for $C_{21}H_{30}N2O_2$:
  Calcd.: C, 73.65; H, 8.83; N, 8.18
  Found: C, 73.60; H, 8.74; N, 8.09

TABLE 38

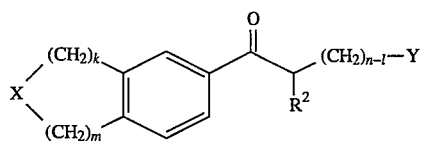

| Compound No. | X | k | m | n | R² | Y | m. p. (°C.) | Molecular Formula | Elemental Analysis Calcd. (Found) | | |
|---|---|---|---|---|---|---|---|---|---|---|---|
| | | | | | | | | | C | H | N |
| 1 | NCH₂Ph | 2 | 2 | 3 | Ph | Br | oil | $C_{27}H_{28}BrNO$ | 70.13 (70.02 | 6.10 6.13 | 3.03 3.02) |

WORKING EXAMPLE 2

1-[3-(Phenylmethyl)-2,3,4,5-tetrahydro-1H-3-benzazepin-7-yl]-4-(piperidin-1-yl)-1-butanone dihydrochloride

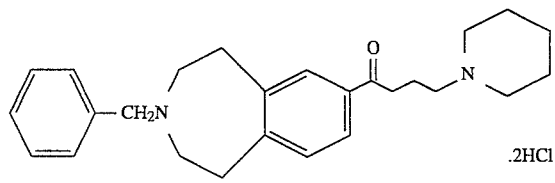

.2HCl

To 2.10 g of the compound obtained in Working Example 1 was added 21 ml of conc. hydrochloric acid, and the mixture was heated for 16 hours under reflux. Excess volume of the conc. hydrochloric acid was distilled off under reduced pressure. To the residue was added 50 ml of water, and the mixture was washed with 50 ml of dichloromethane. The aqueous layer was made basic with an aqueous solution of sodium hydroxide, which was subjected to extraction with dichloromethane. The extract solution was dried over anhydrous sodium sulfate, then the solvent was distilled off to leave 1.80 g of an oily substance.

To a suspension of 1.80 g of the above-mentioned oily substance and 1.30 g of potassium carbonate in 20 ml of ethanol was added dropwise a solution of 0.97 g of benzyl bromide in 5 ml of ethanol. The mixture was stirred for 4 hours at room temperature. The solvent was distilled off under reduced pressure. To the residue was added 30 ml of water, and the mixture was subjected to extraction with dichloromethane. The extract solution was dried over anhydrous sodium sulfate, followed by distilling off the solvent to give 1.37 g of the free form of the title compound as colorless powder, m.p.90°–92° C. 1.0 g of the thus obtained free compound was dissolved in methanol, to which was added 1.5 ml of 4N-methanolic hydrochloride. The solvent was distilled off under reduced pressure to leave a solid substance, which was recrystallized from methanol-ethyl acetate to afford 0.93 g of the title compound as colorless crystals, m.p.210°–215° C. (decomp.)

Elemental Analysis for $C_{26}H_{34}N_2O\cdot 2HCl$:
  Calcd.: C, 67.38; H, 7.83; N, 6.04
  Found : C, 67.12; H, 7.81; N, 6.00

WORKING EXAMPLE 3

Using the compound obtained in Reference Example 2, the procedure of Working Example 1 was followed to give compounds shown in Table 39.

TABLE 39

| Compound No. | n | $N(R^3)(R^4)$ | m.p. (°C.) | Molecular Formula | Elemental Analysis Calcd. (Found) C | H | N |
|---|---|---|---|---|---|---|---|
| 1 | 2 | pyrrolidin-1-yl | 113–115 | $C_{19}H_{26}N_2O_2\cdot$HCl | 65.04 (64.91 | 7.76 7.74 | 7.98 7.96) |
| 2 | 2 | piperidin-1-yl | 181–182 | $C_{20}H_{28}N_2O_2\cdot$HCl | 65.83 (65.63 | 8.01 7.94 | 7.68 7.73) |
| 3 | 2 | morpholin-4-yl | 99–103 | $C_{19}H_{26}N_2O_3\cdot$HCl | 62.20 (61.95 | 7.42 7.44 | 7.64 7.58) |
| 4 | 2 | 4-benzylpiperazin-1-yl | 170–175 | $C_{26}H_{33}N_3O_2\cdot$2HCl·2H$_2$O | 59.09 (58.83 | 7.44 7.34 | 7.95 7.78) |
| 5 | 2 | 4-benzylpiperidin-1-yl | amorphous powder | $C_{27}H_{34}N_2O_2\cdot$HCl·2H$_2$O | 66.04 (65.70 | 8.00 8.05 | 5.70 5.66) |

WORKING EXAMPLE 4

Using the compound obtained in Working Example 3, the procedure of Working Example 2 was followed to give the compound shown in Table 40.

TABLE 40

| Compound No. | n | $R^3$, $R^4$ (N) | m.p. (°C.) | Molecular Formula | Elemental Analysis Calcd. (Found) | | |
|---|---|---|---|---|---|---|---|
| | | | | | C | H | N |
| 1 | 2 | piperidin-1-yl | 163–165 | $C_{25}H_{32}N_2O$·2HCl | 66.81 (66.83 | 7.62 7.54 | 6.23 6.24) |

WORKING EXAMPLE 5

1-[3-(Phenylmethyl)-2,3,4,5-tetrahydro-1H-3-benzazepin- 7-yl]-3-(piperidin-1-yl)-1-propanone dihydrochloride

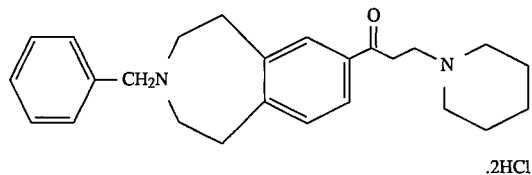

.2HCl

To a solution of 1.40 g of the compound obtained in Reference Example 3, 1.22 g of piperidine hydrochloride, 1.5 g of paraformaldehyde in 50 ml of ethanol was added 0.7 ml of conc. hydrochloride, and the mixture was stirred for 24 hours under reflux. The solvent was distilled off. To the residue were added 50 ml of ethyl acetate and 50 ml of pure water. The aqueous layer was separated, whose pH was adjusted to not lower than 10, followed by extraction with 50 ml of ethyl acetate. The extract solution was dried over anhydrous sodium sulfate, from which the solvent was distilled off to leave 2.15 g of an oily residue.

The residue was purified by means of alumina chromatography (developing solvent; dichloromethane-ethyl acetate= 9:1) to give 1.4 g of an oily substance. The oily substance was dissolved in 15 ml of methanol, to which was added 2.0 ml of 4N methanolic hydrochloric acid. The solvent was distilled off, and the crystalline residue was recrystallized from ethanol-ethyl acetate to afford 1.05 g of the title compound as colorless crystals, m.p.163°–165° C. Elemental Analysis for $C_{25}H_{32}N_2O$·2HCl:

Calcd.: C, 66.81; H, 7.62; N, 6.23
Found : C, 66.65; H, 7.64; N, 6.17

WORKING EXAMPLE 6

Using the compound obtained in Reference Example 3, the procedure of Working Example 5 was followed to give compounds shown in Table 41.

TABLE 41

| Compound No. | $R^2$ | $R^3$, $R^4$ (N) | m.p. (°C.) | Molecular Formula | Elemental Analysis Calcd. (Found) | | |
|---|---|---|---|---|---|---|---|
| | | | | | C | H | N |
| 1 | H | 4-(CH$_2$Ph)piperazin-1-yl | Amorphous powder | $C_{31}H_{37}N_3O$·3HCl | 64.53 (64.69 | 6.99 7.17 | 7.28 6.99) |

TABLE 41-continued

| Compound No. | R² | NR³R⁴ (ring) | m. p. (°C.) | Molecular Formula | Elemental Analysis Calcd. (Found) C | H | N |
|---|---|---|---|---|---|---|---|
| 2 | H | N-piperidinyl-CH₂Ph | 183–186 | C₃₂H₃₈N₂O. 2HCl.2H₂O | 66.77 (66.96 | 7.70 7.50 | 4.87 4.70) |
| 3 | H | piperazinyl-pyrimidinyl | 183–188 (decomp.) | C₂₉H₃₄N₄O. 3HCl.2H₂O | 58.05 (57.84 | 6.89 6.92 | 9.34 9.26) |
| 4 | H | piperazinyl-N-CO-C₆H₄-F | Amorphous powder | C₃₁H₃₄FN₃O₂. 2HCl.H₂O | 63.05 (63.23 | 6.49 6.73 | 7.12 6.84) |
| 5 | H | piperazinyl-N-CH₂Ph | 100–102 | C₃₁H₃₇N₃O | 79.62 (79.55 | 7.97 7.99 | 8.99 8.84) |

WORKING EXAMPLE 7

7-[N-ethyl-N-(phenylmethyl)amino]-1-(2,3,4,5-tetrahydro-1H-1-benzazepin-8-yl)-1-heptanone fumarate

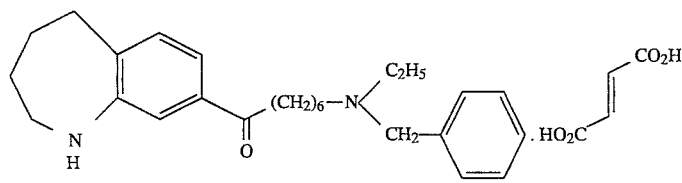

(1) A mixture of 1.7 g of ethyl β-(1-acetyl-2,3,4,5-tetrahydro-1H-1-benzazepin-8-yl)-β-oxopropionate, 2.6 of 1,5-dibromopentane, 0.93 g of potassium carbonate and 50 ml of acetone was heated for 16 hours under reflux. The reaction mixture was left standing for cooling, then the resulting solid matter was filtered off. From the filtrate was distilled off the solvent. The residue was purified by means of column chromatography (developing solvent; dichloromethane-ethyl acetate= 10:1(V/V)) to afford 1.8 g of ethyl β-(1-acetyl-2,3,4,5-tetrahydro-1H-1-benzazepin-8-yl)-α-(5-bromopentyl)-β-oxopropionate as a viscous oily substance.

Elemental Analysis for C₂₂H₃₀BrNO₄:

Calcd.: C, 58.41; H, 6.68; N, 3.10

Found : C, 58.26; H, 6.63; N, 3.04

(2) A solution of 0.5 g of the compound obtained in (1) and 0.3 g of N-ethylbenzylamine in 10 ml of toluene was heated for 24 hours under reflux. The reaction mixture was left standing for cooling, then the resulting solid matter was filtered off. From the filtrate was distilled off the solvent. To the residue was added 30 ml of conc. hydrochloric acid. The mixture was heated for 24 hours under reflux, then excess volume of conc. hydrochloric acid was distilled off under reduced pressure. To the residue was added a 5% aqueous solution of sodium hydroxide, which was subjected to extraction with dichloromethane. The extract solution was dried over anhydrous sodium sulfate, from which the solvent was distilled off. The residue was purified by means of column chromatography (developing solvent; ethyl acetate-methanol=20:1(V/V)) to give 55 mg of a colorless oily product, which was processed with 16 mg(one equivalent) of fumaric acid to afford 60 mg of the title compound as an amorphous powder.

Elemental Analysis for C₂₆H₃₆N₂O.C₄H₄O₄:

Calcd.: C, 70.84; H, 7.93; N, 5.51

Found: C, 70.59; H, 8.04; N, 5.47

WORKING EXAMPLE 8

1-(3-Acetyl-2,3,4,5-tetrahydro-1H-3-benzazepin-7-yl)-2-(piperidin-1-yl)-1-ethanone hydrochloride

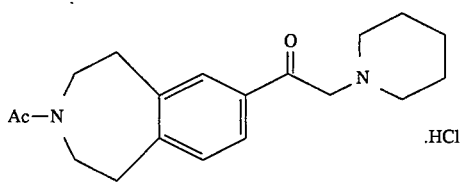

In 10 ml of dichloromethane was dissolved 1.50 g of 1-(3-acetyl-2,3,4,5-tetrahydro-1H-3-benzazepin-7-yl)-2-chloro-1-ethanone obtained in Reference Example 2. To the solution was added 1.7 ml of piperidine, and the mixture was stirred for one hour at room temperature. The reaction mixture was poured into an aqueous solution of potassium carbonate, which was subjected to extraction with dichloromethane. The extract was dried over anhydrous sodium sulfate, from which was distilled off the solvent to leave an oily residue. To the residue was dissolved in 5 ml of methanol, to which was added 1.7 ml of 4N methanolic hydrochloric acid. Then the solvent was distilled off to leave 1.50 g of the title compound as colorless powder.

Elemental Analysis for $C_{19}H_{26}N_2O_2 \cdot HCl$:
  Calcd.: C, 65.04; H, 7.76; N, 7.98
  Found : C, 64.92; H, 7.81; N, 7.87

WORKING EXAMPLE 9

1-[3-(Phenylmethyl)-2,3,4,5-tetrahydro-1H-3-benzazepin-7-yl]-2-(piperidin-1-yl)-1-ethanone dihydrochloride

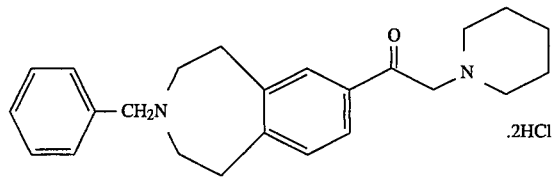

To 1.40 g of the compound obtained in Working Example 8 was added 20 ml of conc. hydrochloric acid. The mixture was stirred for 13 hours under reflux. The reaction mixture was cooled to 25° C., to which was added 50 ml of pure water. The mixture was washed with 50 ml of dichloromethane. The aqueous layer was made basic with an aqueous solution of sodium hdyroxide, which was subjected to extraction with 50 ml of dichloromethane. The extract was dried over anhydrous sodium sulfate, from which was distilled off the solvent to leave 1.15 g of an oily product.

To a suspension of 0.50 g of the above-mentioned oily product and 0.31 g of potassium carbonate in 10 ml of ethanol was added dropwise a solution of 0.30 g of benzyl bromide in 5 ml of ethanol, and the mixture was stirred for 16 hours at room temperature. The solvent was distilled off. To the residue were added 20 ml of dichloromethane and 20 ml of pure water. The organic layer was separated, dried over anhydrous sodium sulfate, followed by distilling off the solvent. The residue was dissolved in 10 ml of methanol, to which was added 1.1 ml of 4N methanolic hydrochloric acid. The solvent was then distilled off to leave a solid matter. Recrystallization from methanol-ethyl acetate afforded 0.2 g of the title compound as colorless crystals, m.p.236°–239° C. (decomp.).

Elemental Analysis for $C_{24}H_{30}N_2O \cdot 2HCl$:
  Calcd.: C, 66.20; H, 7.41; N, 6.43
  Found: C, 66.11; H, 7.39; N, 6.38

WORKING EXAMPLE 10

Using the compounds obtained in Reference Example 1 or Reference Example 5, the procedure of Working Example 1 was followed to give compounds shown in Table 42, Table 43, Table 44 and Table 45.

TABLE 42

| Compound No. | X | k | m | n | $NR^3R^4$ | m. p. (°C.) | Molecular Formula | Elemental Analysis Calcd. (Found) C | H | N |
|---|---|---|---|---|---|---|---|---|---|---|
| 1 | NAc | 0 | 4 | 2 | N(piperazine)N—CH₂Ph | 163–167 | $C_{26}H_{33}N_3O_2 \cdot$ 2HCl | 63.41 (63.24 | 7.16 7.05 | 8.53 8.48) |

TABLE 42-continued

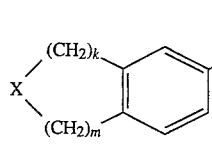

| Compound No. | X | k | m | n | $\overset{R^3}{\underset{R^4}{N\diagdown}}$ | m.p. (°C.) | Molecular Formula | Elemental Analysis Calcd. (Found) C | H | N |
|---|---|---|---|---|---|---|---|---|---|---|
| 2 | NCO₂Et | 0 | 4 | 2 | N‾‾N—CH₂Ph (piperazine) | 160–163 | $C_{27}H_{35}N_3O_3 \cdot$ 2HCl·½H₂O | 61.01 (61.06 | 7.21 7.33 | 7.91 7.89) |
| 3 | NCH₂Ph | 2 | 2 | 2 | N‾‾N—Me | 198–202 | $C_{25}H_{33}N_3O \cdot$ 3HCl·2H₂O | 55.92 (56.29 | 7.51 7.55 | 7.83 7.40) |
| 4 | NCH₂Ph | 2 | 2 | 2 | N‾‾N—CH₂CH₂OH | 165–168 | $C_{26}H_{35}N_3O_2 \cdot$ 3HCl·³⁄₂H₂O | 55.97 (55.69 | 7.41 7.55 | 7.53 7.26) |
| 5 | NCH₂Ph | 2 | 2 | 2 | N‾‾O (morpholine) | 176–179 | $C_{24}H_{30}N_2O_2 \cdot$ 2HCl·½H₂O | 62.61 (62.33 | 7.21 7.38 | 6.08 5.83) |
| 6 | NCH₂Ph | 2 | 2 | 2 | N‾‾=O (4-piperidone) | 155–157 | $C_{25}H_{30}N_2O_2 \cdot$ 2HCl·2H₂O | 60.12 (60.14 | 7.26 7.53 | 5.61 5.39) |
| 7 | NCH₂Ph | 2 | 2 | 2 | spiro piperidine–imidazolidinone N–Ph | 181–184 | $C_{33}H_{38}N_4O_2 \cdot$ ½H₂O | 74.55 (74.45 | 7.39 7.39 | 10.12 10.12) |
| 8 | NCH₂Ph | 2 | 2 | 2 | 1,2,3,4-tetrahydroisoquinolin-2-yl | 198–203 | $C_{29}H_{32}N_2O \cdot$ 2HCl·H₂O | 67.57 (67.85 | 7.04 7.05 | 5.43 5.15) |
| 9 | NCH₂Ph | 2 | 2 | 2 | N‾‾N—Ac | amorphous powder | $C_{26}H_{33}N_3O_2 \cdot$ 2HCl·2H₂O | 59.09 (59.24 | 7.44 7.21 | 7.95 7.99) |

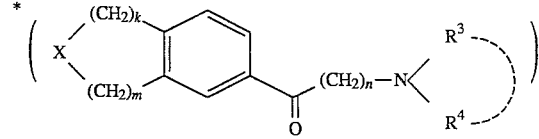

TABLE 43
| Compound No. | X | k | m | n | $R^3 \diagdown N \diagup R^4$ | m.p. (°C.) | Molecular Formula | Elemental Analysis Calcd. (Found) | | |
|---|---|---|---|---|---|---|---|---|---|---|
| | | | | | | | | C | H | N |
| 10 | NCH$_2$Ph | 2 | 2 | 2 | 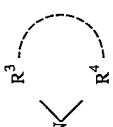 | 168–171 | C$_{30}$H$_{35}$N$_3$O.3HCl.H$_2$O | 62.02 (62.18) | 6.94 (6.92) | 7.23 (7.20) |
| 11 | NCH$_2$Ph | 2 | 2 | 2 | 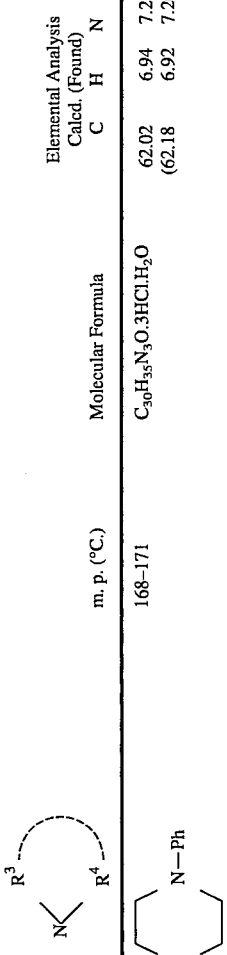 | 174–177 | C$_{32}$H$_{37}$N$_3$O$_3$.3HCl.3H$_2$O | 56.93 (57.17) | 6.87 (6.73) | 6.22 (5.93) |
| 12 | NCH$_2$Ph | 2 | 2 | 2 | 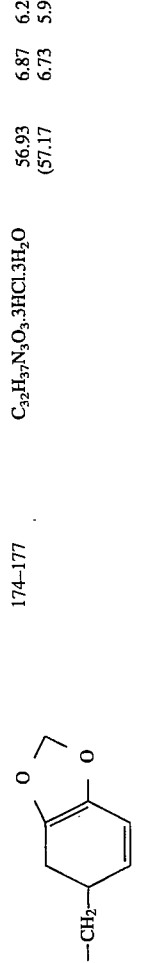 | amorphous powder | C$_{29}$H$_{33}$ClN$_2$O$_2$.2HCl.2H$_2$O | 59.44 (59.76) | 6.71 (6.69) | 4.78 (4.41) |
| 13 | NCH$_2$Ph | 2 | 2 | 2 | 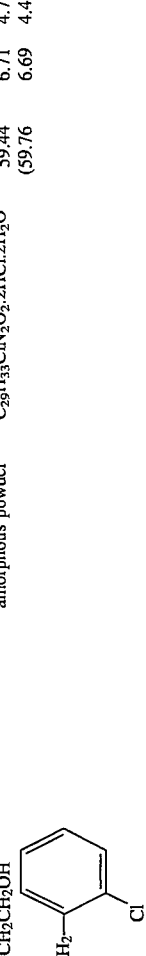 | 137–139 | C$_{44}$H$_{52}$N$_4$O$_2$.¼H$_2$O | 77.96 (77.98) | 7.88 (7.98) | 8.26 (8.40) |
| 14 | NCH$_2$Ph | 2 | 2 | 2 | 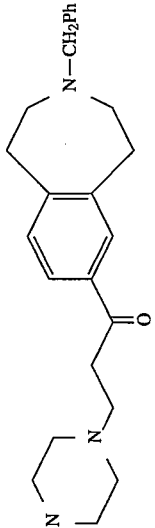 | 243–248 (decomp.) | C$_{31}$H$_{35}$ClN$_2$O$_2$.2HCl | 64.64 (64.49) | 6.47 (6.56) | 4.86 (4.77) |
| 15 | NCH$_2$Ph | 2 | 2 | 1 | 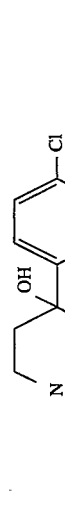 | amorphous powder | C$_{30}$H$_{35}$N$_3$O.3HCl.½H$_2$O | 59.26 (59.39) | 6.91 (7.23) | 6.60 (6.60) |
| 16 | NCH$_2$Ph | 2 | 2 | 5 | 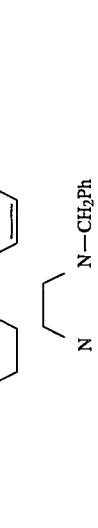 | 182–185 | C$_{34}$H$_{43}$N$_3$O.3HCl | 65.96 (65.92) | 7.49 (7.58) | 6.79 (6.68) |

TABLE 43-continued
$\overset{R^3 \diagdown}{\underset{R^4 \diagup}{N}}$
| Compound No. | X | k | m | n | $R^3, R^4$ | m.p. (°C.) | Molecular Formula | Elemental Analysis Calcd. (Found) C H N |
|---|---|---|---|---|---|---|---|---|
| 17 | NAc | 2 | 2 | 3 | 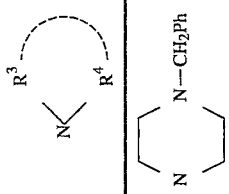 N—CH$_2$Ph | 122–125 | C$_{27}$H$_{35}$N$_3$O$_2$ | 74.79 8.14 9.69 (74.58 8.16 9.63) |

TABLE 44

| Compound No. | X | k | m | n | R³R⁴ group | m.p. (°C.) | Molecular Formula | Elemental Analysis Calcd. (Found) C | H | N |
|---|---|---|---|---|---|---|---|---|---|---|
| *18 | NCHO | 0 | 2 | 2 | N⟨  ⟩NCH₂Ph (piperazine) | 194–196 | C₂₃H₂₇N₃O₂ .2HCl.1/2H₂O | 60.13 (60.16 | 6.58 6.53 | 9.15 9.09) |
| 19 | NCHO | 1 | 3 | 2 | N⟨  ⟩NCH₂Ph | 213–215 (decomp.) | C₂₅H₃₁N₃O₂ .2HCl.1/2H₂O | 61.60 (61.77 | 7.03 6.99 | 8.62 8.50) |
| *20 | NCHO | 0 | 2 | 2 | N⟨  ⟩NCH₂Ph | 82–84 | C₂₃H₂₇N₃O₂ | 73.18 (72.91 | 7.21 7.32 | 11.13 11.11) |
| 21 | NCH₂Ph | 2 | 2 | 2 | N⟨  ⟩NCH₂-(4-pyridyl) | 186–189 | C₃₀H₃₆N₄O .4HCl.3H₂O | 53.90 (53.71 | 6.94 7.06 | 8.38 8.65) |
| 22 | NCHO | 2 | 2 | 2 | N⟨  ⟩N—CH₂Ph | 106–108 | C₂₅H₃₁N₃O₂ | 74.04 (73.99 | 7.70 7.70 | 10.36 10.39) |
| 23 | NAc | 2 | 2 | 4 | N⟨  ⟩N—CH₂Ph | 191–194 | C₂₈H₂₇N₃O₂ .2HCl.3H₂O | 58.53 (58.71 | 7.89 7.63 | 7.31 7.18) |
| 24 | NCH₂Ph | 2 | 2 | 2 | N⟨  ⟩NCHO | 168–172 | C₂₅H₃₁N₃O₂ .2HCl.2H₂O | 58.36 (58.60 | 7.25 7.17 | 8.17 8.15) |
| 25 | NCH₂Ph | 2 | 2 | 2 | N(CH₂Ph)₂ | 138–139 | C₃₄H₃₆N₂O .2HCl.3/2H₂O | 69.38 (69.65 | 7.02 7.06 | 4.76 4.69) |

TABLE 45

| Compound No. | X | k | m | n | R³R⁴ group | m.p. (°C.) | Molecular Formula | Elemental Analysis Calcd. (Found) C | H | N |
|---|---|---|---|---|---|---|---|---|---|---|
| 26 | NCH₂Ph | 2 | 2 | 2 | N⟨  ⟩NCHPh₂ | 140–142 | C₃₇H₄₁N₃O | 81.73 (81.53 | 7.60 7.62 | 7.73 7.62) |
| 27 | NCO₂CH₃ | 2 | 2 | 2 | N⟨  ⟩NCH₂Ph | 98–101 | C₂₆H₃₃N₃O₃ | 71.70 (71.83 | 7.64 7.69 | 9.65 9.68) |
| *28 | NCHO | 0 | 2 | 2 | N⟨  ⟩N—Ph | 236–238 (decomp.) | C₂₂H₂₅N₃O₂ .2HCl.5/2H₂O | 54.89 (54.70 | 6.70 6.52 | 8.73 9.01) |

TABLE 45-continued

| Compound No. | X | k | m | n | R³, R⁴ group | m.p. (°C.) | Molecular Formula | Elemental Analysis Calcd. (Found) C | H | N |
|---|---|---|---|---|---|---|---|---|---|---|
| 29 | NCH₂Ph | 2 | 2 | 2 | N / NCH₂Ph (7-ring) | amorphous powder | C₃₂H₃₉N₃O .3HCl.H₂O | 63.10 (62.98 | 7.28 7.10 | 6.90 7.03) |
| 30 | NCHO | 0 | 3 | 2 | N / NCH₂Ph (6-ring) | 218–221 (decomp.) | C₂₄H₂₉N₃O₂ .2HCl.½H₂O | 60.89 (61.11 | 6.81 6.64 | 8.88 9.11) |
| *31 | NCHO | 0 | 2 | 2 | N / NCH₂Ph (7-ring) | oil | C₂₄H₂₉N₃O₂ | 73.63 (73.81 | 7.47 7.50 | 10.73 10.61) |
| 32 | NCHO | 0 | 3 | 2 | N / NCH₂Ph (6-ring) | 202–207 (decomp.) | C₂₄H₂₉N₃O₂ .2HCl.½H₂O | 60.89 (61.01 | 6.81 6.75 | 8.88 8.96) |
| 33 | NCHO | 0 | 5 | 2 | N / NCH₂Ph (6-ring) | 187–191 (decomp.) | C₂₆H₃₃N₃O₂ .2HCl.H₂O | 61.17 (60.87 | 7.31 7.28 | 8.23 8.23) |
| 34 | NAc | 0 | 5 | 2 | N / NCH₂Ph (6-ring) | 185–190 (decomp.) | C₂₇H₃₅N₃O₂ .2HCl.H₂O | 61.83 (61.89 | 7.49 7.37 | 8.01 8.24) |

WORKING EXAMPLE 11

3-[4-(Phenylmethyl)piperazin-1-yl]-1-(2,3,4,5-tetrahydro-1H-1-benzazepin-8-yl)-1-propanone trihydrochloride

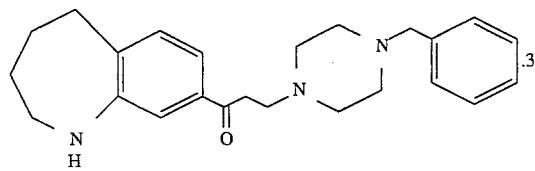

In 100 ml of 6N hydrochloric acid was dissolved 2.0 g of the compound No.2 in Working Example 10. The solution was heated for 16 hours under reflux. Hydrochloric acid was distilled off under reduced pressure. The residue was dissolved in water, which was neutralized with a 5% aqueous solution of sodium hydroxide, followed by extraction with dichloromethane. The extract solution was dried over anhydrous sodium sulfate, from which was distilled off the solvent. The residue was purified by means of column chromatography (developing solvent; ethyl acetate-methanol= 40:1 (v/v) to give 1.2 g of the starting compound (free base) and 0.3 g of the title compound (free base). The title compound (free base) (0.3 g) was treated with triequivalent hydrochloric acid to afford 0.35 g of the title compound (trihydrochloride) as colorless powder, m.p.145°–149° C. Elemental Analysis for $C_{24}H_{31}N_3O.3HCl$:

Calcd.: C, 59.20; H, 7.04; N, 8.63
Found : C, 59.04; H, 7.20; N, 8.53

WORKING EXAMPLE 12

1-(2,3,4,5-Tetrahydro-1H-3-benzazepin-7-Yl)-4-[4-(phenylmethyl)piperazin-1-yl]-1-butanone trihydrochloride

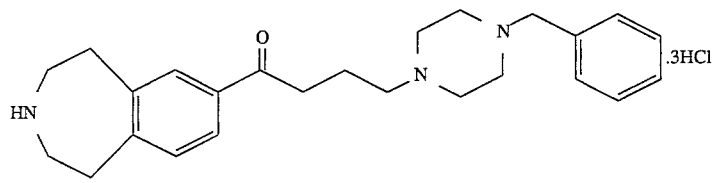

To 2.17 g of 1-(3-acetyl-2,3,4,5-tetrahydro-1H-3-benzazepin-7-yl)-4-(phenylmethyl)piperazin-1-yl]-1-butanone, i.e. Compound No. 17 in Working Example 10, was added 50 ml of conc. hydrochloric acid. The mixture was heated for 24 hours under reflux. Excess amount of conc. hydrochloric acid was distilled off under reduced pressure. To the residue was added 50 ml of water. The mixture was washed with 50 ml of dichloromethane. The aqueous layer was made basic with an aqueous solution of sodium hydroxide, which was subjected to extraction with dichloromethane. The extract solution was dried over anhydrous sodium sulfate. The solvent was distilled off to give 2.0 g of an oily product.

The above-mentioned oily product was dissolved in methanol, to which was added 4.5 ml of 4N-methanolic hydrochloric acid. The solvent was distilled off to leave colorless crystals. The crystals were suspended in 50 ml of ethyl acetate-ether (1:1), followed by collecting the crystals by filtration to give 2.1 g of the title compound as colorless crystals, m.p.201°– 204° C.

Elemental Analysis for $C_{25}H_{33}N_3O.3HCl.H_2O$:
 Calcd.: C, 57.86; H, 7.38; N, 8.10
 Found : C, 57.46; H, 7.36; N, 8.28

WORKING EXAMPLE 13

Using the compound obtained in Working Example 10, the procedure of Working Example 11 (procedure A) or the procedure of Working Example 12 (procedure B) was followed to give compounds shown in Table 46.

TABLE 46

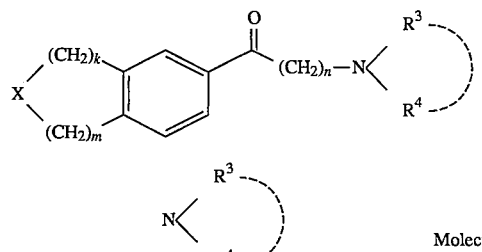

| Compound No. | Method | X | k | m | n | $N\langle{R^3 \atop R^4}$ | m.p. (°C.) | Molecular Formula | Elemental Analysis Calcd. (Found) C | H | N |
|---|---|---|---|---|---|---|---|---|---|---|---|
| 1 | A | NH | 2 | 2 | 2 | N⌒NCH₂Ph | 170–173 | $C_{24}H_{31}N_3O$ .3HCl.2H₂O | 55.12 (54.96 | 7.32 7.40 | 8.04 8.14) |
| *2 | A | NH | 0 | 2 | 2 | N⌒NCH₂Ph | 196 (decomp.) | $C_{22}H_{27}N_3O$ .3HCl.½H₂O | 56.47 (56.61 | 6.68 6.55 | 8.98 9.11) |
| 3 | A | NH | 1 | 3 | 2 | N⌒NCH₂Ph | 188–191 (decomp.) | $C_{24}H_{31}N_3O$ .3HCl.½H₂O | 58.13 (58.11 | 7.11 7.31 | 8.44 8.44) |
| 4 | B | NH | 2 | 2 | 4 | N⌒NCH₂Ph | 228–233 | $C_{26}H_{35}N_3O$ .3HCl.2H₂O | 56.68 (56.98 | 7.68 7.42 | 7.63 7.82) |
| 5 | A | NCH₂Ph | 2 | 2 | 2 | N⌒NH | 187–190 | $C_{24}H_{31}N_3O$ .3HCl.5/2H₂O | 54.19 (54.41 | 7.39 7.51 | 7.90 7.65) |
| *6 | A | NH | 0 | 2 | 2 | N⌒NCH₂Ph | 97–99 | $C_{22}H_{27}N_3O$ | 75.61 (75.26 | 7.79 7.74 | 12.02 11.99) |
| *7 | A | NH | 0 | 2 | 2 | N⌒N—Ph | 140–142 (decomp.) | $C_{21}H_{25}N_3O$ .3HCl.H₂O | 54.50 (54.54 | 6.53 6.54 | 9.08 8.82) |
| 8 | A | NH | 0 | 3 | 2 | N⌒NCH₂Ph | 174–176 (decomp.) | $C_{23}H_{29}N_3O$ .3HCl.H₂O | 56.27 (56.52 | 6.98 6.82 | 8.56 8.58) |
| *9 | A | NH | 0 | 2 | 2 | N⌒NCH₂Ph (7-ring) | 159–163 | $C_{23}H_{29}N_3O$ .3HCl.H₂O | 56.27 (55.97 | 6.98 7.05 | 8.56 8.41) |

TABLE 46-continued $$\underset{(CH_2)_m}{\overset{(CH_2)_k}{X}} \diagdown \text{Ar-CO-(CH}_2)_n\text{-NR}^3\text{R}^4$$

| Compound No. | Method | X | k | m | n | NR³R⁴ | m.p. (°C.) | Molecular Formula | Elemental Analysis Calcd. (Found) C | H | N |
|---|---|---|---|---|---|---|---|---|---|---|---|
| 10 | A | NH | 0 | 3 | 2 | N(piperazinyl)NCH₂Ph | 205–211 (decomp.) | C₂₃H₂₉N₃O .3HCl | 58.42 (58.19 | 6.82 6.82 | 8.89 8.70) |
| 11 | A | NH | 0 | 5 | 2 | N(piperazinyl)NCH₂Ph | 194–196 (decomp.) | C₂₅H₃₃N₃O .3HCl.½H₂O | 58.88 (59.15 | 7.31 7.45 | 8.24 8.30) |

*X(CH₂)ₖ(CH₂)ₘO(CH₂)ₙ—NR³R⁴

WORKING EXAMPLE 14

By using the compound obtained in Working Example 13, the procedure of Working Example 1 was followed to give compounds shown in Tables 47–51.

TABLE 47

$$\underset{(CH_2)_m}{\overset{(CH_2)_k}{X}} \diagdown \text{Ar-CO-(CH}_2)_n\text{-NR}^3\text{R}^4$$

| Compound No. | X | k | m | n | NR³R⁴ | m.p. (°C.) | Molecular Formula | Elemental Analysis Calcd. (Found) C | H | N |
|---|---|---|---|---|---|---|---|---|---|---|
| *1 | NCH₂Ph | 0 | 2 | 2 | N(piperazinyl)NCH₂Ph | 172–174 | C₂₉H₃₃N₃O .3HCl.3H₂O | 57.76 (57.75 | 7.02 6.75 | 6.97 7.15) |
| 2 | NCH₂Ph | 1 | 3 | 2 | N(piperazinyl)NCH₂Ph | 221–223 (decomp.) | C₃₁H₃₇N₃O .3HCl.½H₂O | 63.53 (63.71 | 7.05 6.93 | 7.17 7.17) |
| 3 | NCH₂Ph | 2 | 2 | 4 | N(piperazinyl)NCH₂Ph | 234–238 | C₃₃H₄₁N₃O .3HCl.3/2H₂O | 62.70 (62.72 | 7.49 7.55 | 6.65 6.72) |
| 4 | NCH₂-C₆H₄-Cl | 2 | 2 | 2 | N(piperazinyl)NCH₂Ph | amorphous powder | C₃₁H₃₆ClN₃O .3HCl.3/2H₂O | 58.31 (58.45 | 6.63 6.91 | 6.58 6.58) |
| 5 | NC₂H₅ | 2 | 2 | 2 | N(piperazinyl)NCH₂Ph | amorphous powder | C₂₆H₃₅N₃O .3HCl.5/2H₂O | 55.76 (55.88 | 7.74 7.94 | 7.50 7.60) |

TABLE 47-continued

[Structure: X(CH₂)ₖ and (CH₂)ₘ attached to benzene ring with C(=O)(CH₂)ₙ-NR³R⁴ group]

| Compound No. | X | k | m | n | NR³R⁴ | m.p. (°C.) | Molecular Formula | C (Calcd./Found) | H | N |
|---|---|---|---|---|---|---|---|---|---|---|
| 6 | NCH₂Ph | 2 | 2 | 2 | piperazinyl-NCH₂-(2-Cl-C₆H₄) | 168–171 | $C_{31}H_{36}ClN_3O$ · 3HCl · 3/2$H_2O$ | 58.31 (58.32 | 6.63 6.76 | 6.58 6.33) |
| 7 | NCH₂Ph | 2 | 2 | 2 | piperazinyl-NCH₂-(3-Cl-C₆H₄) | 176–180 | $C_{31}H_{36}ClN_3O$ · 3HCl · 3/2$H_2O$ | 58.31 (58.21 | 6.63 6.99 | 6.58 6.35) |
| 8 | NCH₂Ph | 2 | 2 | 2 | piperazinyl-NCH₂-(4-Cl-C₆H₄) | 173–176 | $C_{31}H_{36}ClN_3O$ · 3HCl · 5/2$H_2O$ | 56.71 (56.59 | 6.76 6.54 | 6.40 6.13) |
| *9 | NCH₂Ph | 0 | 2 | 2 | piperazinyl-N-Ph | 202–204 (decomp.) | $C_{28}H_{31}N_3O$ · 2HCl | 67.46 (67.19 | 6.67 6.70 | 8.43 8.36) |

*X(CH₂)ₖ(CH₂)ₘO(CH₂)ₙ—NR³R⁴

TABLE 48

[Structure: X(CH₂)ₖ and (CH₂)ₘ attached to benzene ring with C(=O)(CH₂)ₙ-NR³R⁴ group]

| Compound No. | X | k | m | n | NR³R⁴ | m.p. (°C.) | Molecular Formula | C (Calcd./Found) | H | N |
|---|---|---|---|---|---|---|---|---|---|---|
| 10 | NCH₂-(4-Cl-C₆H₄) | 2 | 2 | 2 | piperazinyl-NCH₂Ph | 130–132 | $C_{31}H_{36}ClN_3O$ | 74.16 (73.86 | 7.23 7.25 | 8.37 8.21) |
| 11 | NCH₂-(2-Cl-C₆H₄) | 2 | 2 | 2 | piperazinyl-NCH₂Ph | amorphous powder | $C_{31}H_{36}ClN_3O$ · 3HCl · 9/2$H_2O$ | 53.76 (54.01 | 6.99 6.65 | 6.07 5.92) |
| 12 | NCH₂-(4-NO₂-C₆H₄) | 2 | 2 | 2 | piperazinyl-NCH₂Ph | 170–172 | $C_{31}H_{36}N_4O_3$ · 3HCl · 5/2$H_2O$ | 55.82 (55.76 | 6.65 6.68 | 8.40 8.34) |

TABLE 48-continued

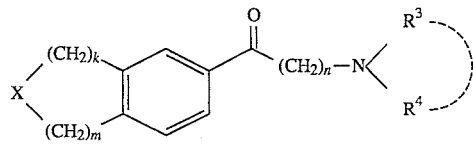

| Compound No. | X | k | m | n | $\overset{R^3}{\underset{R^4}{N}}$ | m.p. (°C.) | Molecular Formula | Elemental Analysis Calcd. (Found) C H N |
|---|---|---|---|---|---|---|---|---|
| 13 | 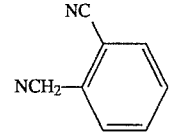 | 2 | 2 | 2 | 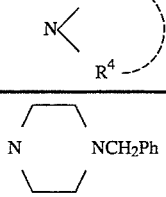 | 161–163 | $C_{32}H_{36}N_4O$ .3HCl.2H$_2$O | 60.24 6.79 8.78 (59.81 6.99 8.72) |
| 14 | 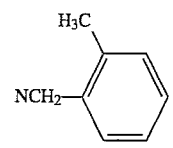 | 2 | 2 | 2 | 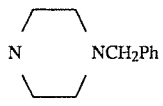 | amorphous powder | $C_{32}H_{39}N_3O$ .3HCl.2H$_2$O | 61.29 7.39 6.70 (61.41 7.50 6.64) |
| 15 | NCH$_2$Ph | 2 | 2 | 2 | 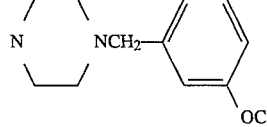 | amorphous powder | $C_{32}H_{39}N_3O_2$ .3HCl.5/2H$_2$O | 58.94 7.26 6.44 (58.96 7.10 6.42) |
| 16 | NCH$_2$Ph | 2 | 2 | 2 | 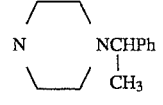 | 172–175 | $C_{32}H_{39}N_3O$ .3HCl.5/2H$_2$O | 60.42 7.45 6.61 (60.30 7.32 6.60) |
| 17 | NCH$_2$Ph | 2 | 2 | 2 | 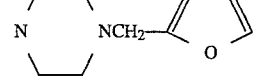 | 110–113 | $C_{29}H_{35}N_3O_2$ | 76.12 7.71 9.18 (76.01 7.73 9.10) |
| 18 | NCH$_2$Ph | 2 | 2 | 2 | 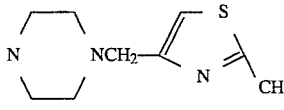 | amorphous powder | $C_{29}H_{36}N_4OS$ .3HCl.7/2H$_2$O | 52.69 7.01 8.47 (52.74 7.10 8.69) |

TABLE 49

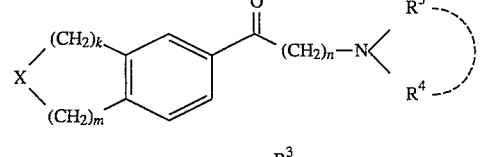

| Compound No. | X | k | m | n | $\overset{R^3}{\underset{R^4}{N}}$ | m.p. (°C.) | Molecular Formula | Elemental Analysis Calcd. (Found) C H N |
|---|---|---|---|---|---|---|---|---|
| 19 | 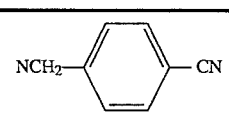 | 2 | 2 | 2 | 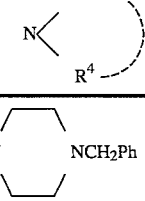 | 202–205 (decomp.) | $C_{32}H_{36}N_4O$ .3HCl.H$_2$O | 61.99 6.66 9.04 (61.80 6.78 9.05) |

TABLE 49-continued

Structure: X-(CH2)k and (CH2)m attached to benzene ring with C(=O)-(CH2)n-NR3R4 group

| Compound No. | X | k | m | n | NR³R⁴ | m.p. (°C.) | Molecular Formula | Elemental Analysis Calcd. (Found) C | H | N |
|---|---|---|---|---|---|---|---|---|---|---|
| 20 | 3-F, 2-NCH₂- phenyl | 2 | 2 | 2 | N—piperazine—NCH₂Ph | 165–168 | $C_{31}H_{36}FN_3O$ ·3HCl·2H₂O | 59.00 (58.76 | 6.87 6.96 | 6.66 6.59) |
| 21 | 2-CH₃O, 3-NCH₂- phenyl | 2 | 2 | 2 | N—piperazine—NCH₂Ph | amorphous powder | $C_{32}H_{39}N_3O_2$ ·3HCl·³/₂H₂O | 60.62 (60.89 | 7.15 7.24 | 6.63 6.46) |
| 22 | 2,4-(OCH₃)₂, 5-NCH₂- phenyl | 2 | 2 | 2 | N—piperazine—NCH₂Ph | 171–174 (decomp.) | $C_{33}H_{41}N_3O_3$ ·3HCl·⁵/₂H₂O | 58.11 (58.32 | 7.24 7.50 | 6.16 6.16) |
| 23 | 4-CH₃, 3-NCH₂- phenyl | 2 | 2 | 2 | N—piperazine—NCH₂Ph | 198–201 (decomp.) | $C_{32}H_{39}N_3O$ ·3HCl·H₂O | 63.10 (63.33 | 7.28 7.33 | 6.90 6.84) |
| 24 | 4-F, 3-NCH₂- phenyl | 2 | 2 | 2 | N—piperazine—NCH₂Ph | 178–180 | $C_{32}H_{36}FN_3O$ ·3HCl·³/₂H₂O | 59.86 (59.93 | 6.81 6.87 | 6.76 6.57) |
| 25 | 3-CH₃, 2-NCH₂- phenyl | 2 | 2 | 2 | N—piperazine—NCH₂Ph | 178–181 (decomp.) | $C_{32}H_{39}N_3O$ ·3HCl·³/₂H₂O | 62.18 (62.15 | 7.34 7.46 | 6.80 6.72) |
| 26 | 3-F, 2-NCH₂- phenyl | 2 | 2 | 2 | N—piperazine—NCH₂Ph | 170–172 | $C_{31}H_{36}FN_3O$ ·3HCl·⁵/₂H₂O | 58.17 (58.45 | 6.93 7.02 | 6.56 6.50) |
| 27 | 3-OCH₃, 2-NCH₂- phenyl | 2 | 2 | 2 | N—piperazine—NCH₂Ph | 173–176 | $C_{32}H_{39}N_3O_2$ ·3HCl·2H₂O | 59.77 (60.10 | 7.21 7.44 | 6.53 6.56) |

TABLE 50

[Structure: X-(CH2)k and (CH2)m connected to benzene ring with C(=O)-(CH2)n-NR3R4 group]

| Compound No. | X | k | m | n | NR3R4 | m.p. (°C.) | Molecular Formula | Elemental Analysis Calcd. (Found) C | H | N |
|---|---|---|---|---|---|---|---|---|---|---|
| 28 | 3-CN-C6H3-NCH2- | 2 | 2 | 2 | N(piperazine)-NCH2Ph | 177–180 | $C_{32}H_{36}N_4O$ ·$3HCl·3/2H_2O$ | 61.10 (60.94 | 6.73 6.94 | 8.91 8.85) |
| 29 | 4-OCH3-C6H3-NCH2- | 2 | 2 | 2 | N(piperazine)-NCH2Ph | 181–184 | $C_{32}H_{39}N_3O_2$ ·$3HCl·3/2H_2O$ | 60.62 (60.56 | 7.15 7.33 | 6.63 6.58) |
| 30 | 4-OH-C6H3-NCH2- | 2 | 2 | 2 | N(piperazine)-NCH2Ph | amorphous powder | $C_{31}H_{37}N_3O_2$ ·$3HCl·5/2H_2O$ | 58.35 (58.45 | 7.11 7.13 | 6.59 6.56) |
| 31 | NCH2CH2Ph | 2 | 2 | 2 | N(piperazine)-NCH2Ph | 217–221 (decomp.) | $C_{32}H_{39}N_3O$ ·$3HCl·3/2H_2O$ | 62.18 (62.26 | 7.34 7.57 | 6.80 6.88) |
| 32 | 3-OCH2Ph-C6H3-NCH2- | 2 | 2 | 2 | N(piperazine)-NCH2Ph | 193–196 | $C_{38}H_{43}N_3O_2$ ·$3HCl·3/2H_2O$ | 64.27 (64.35 | 6.95 6.94 | 5.92 5.10) |
| 33 | NCH2CH(CH3)2 | 2 | 2 | 2 | N(piperazine)-NCH2Ph | 167–170 | $C_{28}H_{39}N_3O$ ·$3HCl·3H_2O$ | 56.33 (56.57 | 8.10 8.25 | 7.04 7.04) |
| 34 | 3-NO2-C6H3-NCH2- | 2 | 2 | 2 | N(piperazine)-NCH2Ph | 178–181 (decomp.) | $C_{31}H_{36}N_4O_3$ ·$3HCl·3/2H_2O$ | 57.37 (57.12 | 6.52 6.73 | 8.63 8.47) |
| 35 | 2,3,4-(OCH3)3-C6H2-NCH2- | 2 | 2 | 2 | N(piperazine)-NCH2Ph | 178–181 (decomp.) | $C_{34}H_{43}N_3O_4$ ·$3HCl·H_2O$ | 59.61 (59.53 | 7.06 7.35 | 6.13 6.06) |
| 36 | 2,4-(OCH3)2-C6H3-NCH2CH2- | 2 | 2 | 2 | N(piperazine)-NCH2Ph | 178–182 (decomp.) | $C_{34}H_{43}N_3O_3$ ·$3HCl·3H_2O$ | 57.91 (58.09 | 7.43 7.22 | 5.96 6.00) |

TABLE 51

$$\text{X}\underset{(CH_2)_m}{\overset{(CH_2)_k}{\diagdown}}\!\!\!\!\!\!\!\underset{}{\bigcirc}\!\!\overset{O}{\underset{\|}{C}}-(CH_2)_n-N\underset{R^4\text{---}}{\overset{R^3\text{---}}{\diagup}}$$

| Compound No. | X | k | m | n | $N\overset{R^3\text{---}}{\underset{R^4\text{---}}{\diagup}}$ | m.p. (°C.) | Molecular Formula | Elemental Analysis Calcd. (Found) C | H | N |
|---|---|---|---|---|---|---|---|---|---|---|
| 37 | NCH$_2$CH$_2$CH$_3$ | 2 | 2 | 2 | N⟨⟩NCH$_2$Ph | 177–179 | C$_{27}$H$_{37}$N$_3$O .3HCl.5/2H$_2$O | 56.49 (56.43 | 7.90 8.12 | 7.32 7.38) |
| 38 | NCH$_2$C≡CH | 2 | 2 | 2 | N⟨⟩NCH$_2$Ph | 168–170 | C$_{27}$H$_{33}$N$_3$O .3HCl.2H$_2$O | 57.81 (57.86 | 7.19 7.36 | 7.49 7.40) |
| 39 | NCH$_2$CH$_2$OH | 2 | 2 | 2 | N⟨⟩NCH$_2$Ph | 166–169 | C$_{26}$H$_{35}$N$_3$O$_2$ .3HCl.5/2H$_2$O | 54.22 (54.46 | 7.52 7.36 | 7.30 7.03) |
| 40 | (3-OH-C$_6$H$_3$)NCH$_2$– | 2 | 2 | 2 | N⟨⟩NCH$_2$Ph | 168–170 | C$_{31}$H$_{37}$N$_3$O$_2$ .3HCl.3/2H$_2$O | 60.05 (59.69 | 6.99 6.92 | 6.78 6.80) |
| 41 | (2-OH-C$_6$H$_3$)NCH$_2$– | 2 | 2 | 2 | N⟨⟩NCH$_2$Ph | 168–171 | C$_{31}$H$_{37}$N$_3$O$_2$ .3HCl.2H$_2$O | 59.19 (58.78 | 7.05 6.88 | 6.68 6.44) |
| *42 | NCH$_2$Ph | 0 | 2 | 2 | N⟨⟩NCH$_2$Ph | 185–187 | C$_{29}$H$_{33}$N$_3$O .2HCl.H$_2$O | 65.65 (66.00 | 7.03 7.16 | 7.92 8.00) |
| 43 | NCH$_2$Ph | 2 | 2 | 2 | N⟨⟩NCH$_2$–(thiazol-2-yl)-CH$_3$ | 163–166 (decomp.) | C$_{29}$H$_{36}$N$_4$OS .4HCl.3/2H$_2$O | 52.65 (52.74 | 6.55 6.53 | 8.47 8.44) |

*X(CH$_2$)$_k$(CH$_2$)$_m$O(CH$_2$)$_n$—NR$^{3R^4}$

WORKING EXAMPLE 15

3-Diphenylamino-1-[3-(phenylmethyl)-2,3,4,5-tetrahydro-1H-3-benzazepin-7-yl]-1-propanone hydrochloride

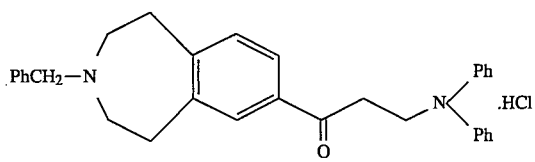

To a solution of 0.98 g of the Compound No. 5 of Reference Example 5 in 30 ml of 1,2-dichloroethane was added 0.63 ml of triethylamine. The mixture was stirred for one hour at room temperature, to which was added 0.56 g of diphenylamine, followed by heating for 72 hours under reflux. The reaction mixture was cooled to room temperature, which was then poured into 50 ml of pure water. To the mixture was added a 1N aqueous solution of sodium hydroxide. The aqueous layer was adjusted to pH not lower than 12, followed by extraction with dichloromethane. The extract solution was dried over anhydrous sodium sulfate, then the solvent was distilled off to leave an oily product. The oily product was purified by means of a silica gel column chromatography (developing solvent: dichloromethane-ethyl acetate=4:1 (v/v)) to afford 0.30 g of the free base of the title compound. The free base was added to 4N methanolic hydrochloric acid, then the solvent was distilled off. The residue was triturated from diethyl ether-hexane to afford 0.25 g of the title compound as amorphous powder.

Elemental Analysis for C$_{32}$H$_{32}$N$_2$O.HCl.H$_2$O:

Calcd.: C, 74.62; H, 6.85; N, 5.44

Found : C, 74.29; H, 6.91; N, 5.40

WORKING EXAMPLE 16

1-(1-Acetyl-2,3-dihydro-1H-indol-5-yl)-3-[4-(phenylmethyl)piperazin-1-yl]-1-propanone dihydrochloride

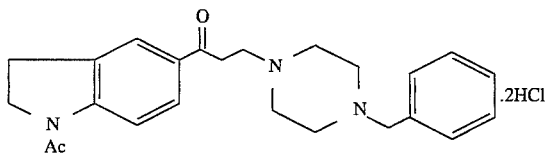

To a solution of 0.7 g of the Compound No.6 of Working Example 13 in 40 ml of dichloromethane was added dropwise 0.2 g of acetic arthydride. The mixture was stirred for 2 hours at room temperature. To the reaction mixture was added a saturated aqueous solution of sodium hydrogencarbonate, followed by extraction with dichloromethane. The extract solution was dried over anhdyrous sodium sulfate, then the solvent was distilled off. The residue was crystallized from diethyl ether to give 0.54 g of the free base of the title compound as pale yellow crystals, m.p.107°–109° C.

To 0.35 g of the above-mentioned free base was added 4N methanolic hydrochloric acid (2 equivalents), followed by distilling off the solvent to afford 0.35 g of the title compound as crystalline powder, m.p.216°– 218° C.

Elemental Analysis for $C_{24}H_{29}N_3O_2.2HCl.2H_2O$:
Calcd.: C, 57.60; H, 7.05; N, 8.40
Found : C, 57.47; H, 6.86; N, 8.26

WORKING EXAMPLE 17

Using the compound of Working Example 13, the procedure of Working Example 16 was followed to afford the compounds shown in Table 52.

TABLE 52

| Compound No. | X | k | m | n | $R^3$, $R^4$ group | m.p. (°C.) | Molecular Formula | Elemental Analysis Calcd. (Found) C | H | N |
|---|---|---|---|---|---|---|---|---|---|---|
| 1 | NAc | 1 | 3 | 2 | N–NCH₂Ph (piperazine) | 196–200 | $C_{26}H_{33}N_3O_2$ .2HCl.H₂O | 61.17 (61.34 | 7.31 7.33 | 8.23 8.14) |
| *2 | NAc | 2 | 0 | 2 | N–N–Ph (piperazine) | 236–238 (decomp.) | $C_{23}H_{27}N_3O_2$ .2HCl.5/2H₂O | 54.89 (54.70 | 6.70 6.52 | 8.73 9.01) |
| 3 | NCOPh | 2 | 2 | 2 | N–NCH₂Ph (piperazine) | 148–151 | $C_{31}H_{35}N_3O_2$ .2HCl.H₂O | 65.03 (64.96 | 6.87 7.05 | 7.58 7.34) |
| 4 | N–C(=O)-(3-pyridyl) | 2 | 2 | 2 | N–NCH₂Ph (piperazine) | 171–173 (decomp.) | $C_{30}H_{34}N_4O_2$ .3HCl.3H₂O | 55.77 (55.52 | 6.71 6.75 | 8.67 8.43) |
| 5 | NCONHCH₃ | 2 | 2 | 2 | N–NCH₂Ph (piperazine) | 162–164 | $C_{26}H_{34}N_4O_2$ .½H₂O | 70.40 (70.45 | 7.95 7.87 | 12.63 12.49) |
| *6 | NAc | 3 | 0 | 2 | N–NCH₂Ph (piperazine) | 193–196 (decomp.) | $C_{25}H_{31}N_3O_2$ .2HCl | 62.76 (62.47 | 6.95 7.10 | 8.78 8.73) |

*$X(CH_2)_k(CH_2)_{mO(CH_2)_n}-NR^3R^4$

WORKING EXAMPLE 18

1-(3-Methyl-2,3,4,5-tetrahydro-1H-3-benzazepin-7-yl)-3-[4-(phenylmethyl)piperazin-1-yl]-1-propanone trihydrochloride

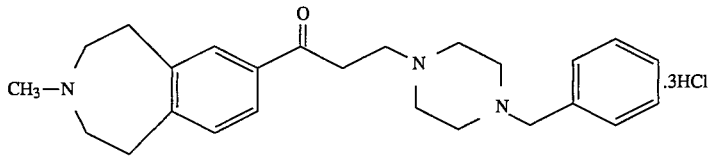

In 30 ml of ethanol was suspended 0.50 g of the compound obtained in Reference Example 6, to which were added 0.55 g of potassium carbonate and 0.42 ml of 1benzyl piperazine at room temperature. The mixture was stirred for 3 hours, to which were added 50 ml of dichloromethane and 50 ml of pure water. The organic layer was separated and washed with 30 ml of pure water, which was then dried over anhydrous sodium sulfate. The solvent was distilled off under reduced pressure to leave 0.2 g of an oily residue. The oily residue was purified by means of an alumina chromatography (developing solvent: dichloromethane-ethyl acetate= 4: 1 (v/v)) to give 0.17 g an oily residue. To the oily residue was added 3 equivalents of mathanolic hydrochloric acid, then methanol was distilled off to afford 0.2 g of the title compound as amorphous powder.
Elemental Analysis for $C_{25}H_{33}N_3O \cdot 2HCl \cdot 3H_2O$:
  Calcd.: C, 55.92; H, 7.51; N, 7.83
  Found : C, 56.01; H, 7.78; N, 7.83

WORKING EXAMPLE 19

1- [3-(Phenylmethyl)-2,3,4,5-tetrahydro-1H-3-benzazepin-7-yl]-2-phenyl-4-(piperidin-1-yl)-1-butanone dihydrochloride

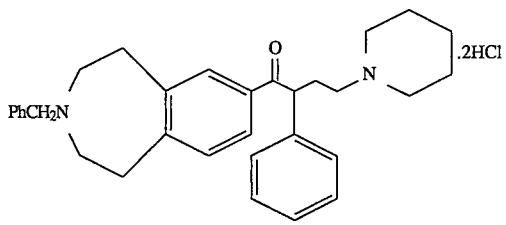

In 20 ml of dichloromethane was dissolved 0.92 g (2 mmol.) of the compound No.1 obtained in Reference Example 9. To the solution was added 0.99 ml (10 mmol.) of piperidine, and the mixture was stirred for one day at room temperature. The reaction mixture was washed with 20 ml of 1N aqueous solution of sodium hydroxide and 20 ml of pure water, followed by drying over sodium sulfate. The solvent was distilled off under reduced pressure. The residue was purified by means of a silica gel column chromatography [developing solvent: ethyl acetate-methanol (4:1)] to afford 0.53 g of the title compound in the free form as an oily substance.

To the oily substance was added 4N-methanolic hydrochloric acid (2 equivalents), then the solvent was distilled off under reduced pressure to give 0.58 g of the title compound as a hydroscopic amorphous powder.
Elemental Analysis for $C_{32}H_{38}N_2O \cdot 2HCl \cdot H_2O$:
  Calcd.: C, 68.93; H, 7.59; N, 5.02
  Found : C, 69.01; H, 7.55; N, 5.05

WORKING EXAMPLE 20

By substantially the same procedure as in Working Example 19, using the compounds obtained in Reference Example 8 or Reference Example 9, compounds shown in Table 53 were obtained.

TABLE 53

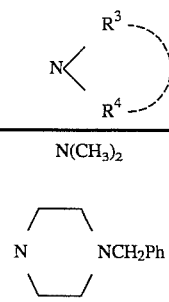

| Compound No. | X | k | m | R² | n | NR³R⁴ | m.p. (°C.) | Molecular Formula | Elemental Analysis Calcd. (Found) | | |
|---|---|---|---|---|---|---|---|---|---|---|---|
| | | | | | | | | | C | H | N |
| 1 | NCH₂Ph | 2 | 2 | Ph | 3 | N(CH₃)₂ | amorphous powder | $C_{29}H_{34}N_2O$ .2HCl.2H₂O | 65.04 (65.17) | 7.53 (7.51) | 5.23 (5.20) |
| 2 | NCHO | 2 | 2 | Ph | 3 | N-piperazinyl-NCH₂Ph | amorphous powder | $C_{32}H_{37}N_3O_2$ .2HCl.H₂O | 65.52 (65.41) | 7.05 (7.01) | 7.16 (7.13) |

FORMULATION EXAMPLE 1

(1) 3-[4-(Phenylmethyl)piperazin-1-yl]-1-[3-(phenylmethyl)-2,3,4,5-tetrahydro-1H-3-benzazepin-7-yl]-1-propanone trihydrochloride (Compound No.1 in [Table 17], Working Example 6) 1 g
(2) Lactose 197 g
(3) Corn starch 50 g
(4) Magnesium stearate 2 g (1), (2) and 20 g of corn starch were blended and the mixture was granulated with a paste prepared from 15 g of corn starch and 25 ml of water. To this granular product were added 15 g of corn starch and (4), and the resulting composition was compression-molded to provide 2000 tablets each measuring 3 mm in diameter and containing 0.5 mg of (1).

FORMULATION EXAMPLE 2

(1) 3-[4-(phenylmethyl)piperazin-1-yl]-1-[3-(phenylmethyl)-2,3,4,5-tetrahydro-1H-3-benzazepin-7-yl]-1-propanone trihydrochloride (Compound No.1 in [Table 17], Working Example 6) 2 g
(2) Lactose 197 g
(3) Corn starch 50 g
(4) Magnesium stearate 2 g (1), (2) and 20 g of corn starch were blended and the mixture was granulated with a paste prepared from 15 g of corn starch and 25 ml of water. To this granular product were added 15 g of corn starch and (4), and the resulting composition was compression-molded to provide 2000 tablets each measuring 3 mm in diameter and containing 1.0 mg of (1).

EXPERIMENTAL EXAMPLE 1

The cholinesterase inhibitory activity of the compound of this invention was assayed with (acetyl-[³H])-acetylcholine. More specifically, using the $S_1$ fraction of a homogenate of male Wistar rat cerebral cortex as the cholinesterase source, (acetyl[³H])-acetylcholine as the substrate and the compound of this invention as the test sample were added. The mixture was incubated for 30 minutes, then the reaction was terminated, to which was added a toluene-based scintillant, then the mixture was shaken. The reaction product [³H]-acetic acid was transferred to the toluene layer, which was subjected to determination of cholinesterase activity by counting with a liquid scintillation counter.

The cholinesterase inhibitory activity of the test compound was expressed in 50% inhibitory concentration ($IC_{50}$). The cholinesterase activity of physostigmine was also determined by the same procedure. The results are shown in Table 54.

TABLE 54

| Compound (Working Example No.) | Acetylcholinesterase inhibitory activity $IC_{50}$ (μM) |
|---|---|
| 3-4 | 0.119 |
| 6-1 | 0.049 |
| 6-5 | 0.0526 |
| 10-18 | 0.0152 |
| 10-19 | 0.171 |
| 10-20 | 0.0152 |
| 10-22 | 0.0928 |
| 10-26 | 0.0526 |
| 10-27 | 0.169 |
| 10-30 | 0.0599 |
| 10-32 | 0.118 |
| 13-1 | 0.0493 |
| 13-3 | 0.0789 |
| 13-8 | 0.163 |
| 14-2 | 0.0538 |
| 14-4 | 0.147 |
| 14-5 | 0.0188 |
| 14-6 | 0.113 |
| 14-10 | 0.167 |
| 14-14 | 0.0636 |
| 14-19 | 0.0339 |
| 14-20 | 0.0478 |
| 14-21 | 0.0226 |
| 14-22 | 0.0215 |
| 14-23 | 0.0661 |
| 14-25 | 0.0696 |
| 14-27 | 0.133 |
| 14-29 | 0.0257 |
| 14-31 | 0.033 |
| 14-33 | 0.0341 |
| 14-36 | 0.0168 |
| 14-40 | 0.0602 |
| 16 | 0.0251 |
| 17-3 | 0.0825 |
| 18 | 0.0338 |
| Physostigmine | 0.220 |

The results shown in Table 54 indicate that the compound of the present invention has superior cholinesterase inhibitory activity to physostigmine.

EXPERIMENTAL EXAMPLE 2

Effects of the compound of this invention on monoamine uptake were investigated using [$^3$H]-norepinephirine(NE) and [$^3$H]-serotonin (5-HT). Rats were sacrificed by decapitation. The cerebral cortex and hippocampus were removed and homogenized in 10–15 volumes (W/V) of an ice-cold medium containing 0.32M sucrose. Crude synaptosomal preparations (P2) were isolated after differential centrifugation at 1000× g for 10 min and 20,000× g for 30 min at 4° C. Synaptosomal membranes were suspended in Krebs-Ringer bicarbonate (KRB) solution (116 mM NaC1, 4.8 mM KCl, 1.3 mM CaCl$_2$, 1.2 mMMgSO$_4$, 1.2 mM NaH$_2$PO$_4$, 25 mM NaHCO$_3$, 0.1 mM EDTA-2Na, 11.1 mM glucose, 0.11 mM ascorbic acid, 0.01 mM pargyline). Synaptosomal membrane suspension (900 μl) was preincubated with the test compound dissolved in DMSO solution at 37° C. for 5 min. The reaction was initiated by addition of 100 μl of [$^3$H]-NE(11 nM in final concentration) or [$^3$H]-5-HT (10 nM in final concentration). Five minutes later, the reaction was stopped by the addition of 4 ml of ice-cold KRB and the reaction mixture was filtered through Whatman GF/B. Filters were washed twice with 4 ml of KRB and the radioactivity bound was counted with liquid scintillant. Imipramine and desipramine were used as positive control All compounds were tested at $10^{-8}$, $10^{-7}$, $10^{-6}$ and $10^{-5}{}_M$. The results are shown in Table 55.

TABLE 55

| Compound (Working Example No.) | Monoamine reuptake inhibitory activity IC$_{50}$(μM) | |
|---|---|---|
| | NE | 5-HT |
| 14-1 | 0.147 | 0.416 |
| 14-6 | 0.725 | 0.0345 |
| 14-7 | 0.822 | 0.0421 |
| 14-23 | 0.912 | 0.0583 |
| 14-29 | 0.429 | 0.0544 |
| 14-31 | 0.441 | 0.0305 |
| 14-33 | 0.74 | 0.0559 |
| 14-36 | 0.70 | 0.0133 |
| 14-40 | 0.359 | 0.0413 |
| Desipramine | 0.15 | 0.45 |
| Imipramine | 1.12 | 0.063 |

The results shown in Table 55 indicate that the compound of the present invention has superior inhibitory activity of monoamine uptake to reference compounds such as desipramine or imipramine.

EFFECTS OF INVENTION

The compound of the present invention has excellent cholinesterase inhibitory activity and monoamine reuptake inhibitory activity and is useful as therapeutic/prophylactic medicament of senile dementia.

What is claimed is:

1. A compound of the formula:

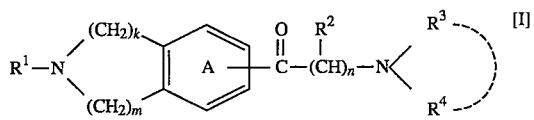

wherein R$^1$ is H, an optionally substituted hydrocarbon group or an optionally substituted acyl group; ring A is an optionally further substituted benzene ring; n is a whole number of 1 to 10; R$^2$, is H or an optionally substituted hydrocarbon group; R$^3$ and R$^4$ form an optionally substituted heterocyclic group, taken together with the adjacent nitrogen atom; R$^{2'}$s may be different from one another in the repetition of n; k is a whole number of 0 to 3; and m is a whole number of 1 to 8; provided that when k=0 and m=2, n is a whole number of not less than 2, and provided that k+m=2 to 5; or a pharmaceutically acceptable salt thereof.

2. A compound as claimed in claim 1, wherein R$^1$ is (1) a hydrogen atom, (2) a straight-chain or branched C$_{1-11}$ alkyl, C$_{2-4}$ alkenyl or C$_{2-4}$ alkynyl group which may be substituted by 1 to 5 substituents selected from the group consisting of a halogen, nitro, cyano, hydroxy, C$_{1-4}$ alkoxy, C$_{1-4}$ alkylthio, amino, mono- or di-C$_{1-4}$ alkyl-substituted amino, 5 to 7-membered cyclic amino, C$_{1-4}$ alkyl-carbonylamino, C$_{1-4}$ alkylsulfonylamino, C$_{1-4}$ alkoxy-carbonyl, carboxyl, C$_{1-6}$ alkyl-carbonyl, carbamoyl, mono- or di-C$_{1-4}$ alkyl-substituted carbamoyl, C$_{1-6}$ alkylsulfonyl, C$_{1-4}$ alkylenedioxy and heterocyclic group, (3) a C$_{3-7}$ monocyclic cycloalkyl group which may be substituted by 1 to 5 substituents selected from the group consisting of a halogen, nitro, cyano, hydroxy, C$_{1-4}$ alkoxy, C$_{1-4}$ alkylthio, amino, mono- or di-C$_{1-4}$ alkyl-substituted amino, 5 to 7-membered cyclic amino, C$_{1-4}$ alkyl-carbonylamino, C$_{1-4}$ alkylsulfonylamino, C$_{1-4}$ alkoxy-carbonyl, carboxyl, C$_{1-6}$ alkyl-carbonyl, carbamoyl, mono- or di-C$_{1-4}$ alkyl-substituted carbamoyl, C$_{1-6}$ alkylsulfonyl, C$_{1-4}$ alkylenedioxy and heterocyclic group, (4) a C$_{8-14}$ bridge ring saturated hydrocarbon group which may be substituted by 1 to 5 substituents selected from the group consisting of a halogen, nitro, cyano, hydroxy, C$_{1-4}$ alkoxy, C$_{1-4}$ alkylthio, amino, mono- or di-C$_{1-4}$ alkyl-substituted amino, 5 to 7-membered cyclic amino, C$_{1-4}$ alkyl-carbonylamino, C$_{1-4}$ alkylsulfonylamino, C$_{1-4}$ alkoxy-carbonyl, carboxyl, C$_{1-6}$ alkyl-carbonyl, carbamoyl, mono- or di-C$_{1-4}$ alkyl-substituted carbamoyl, C$_{1-6}$ alkylsulfonyl, C$_{1-4}$ alkylenedioxy and heterocyclic group, (5) a phenyl or naphthyl group which may be substituted by 1 to 5 substituents selected from the group consisting of a C$_{1-4}$ alkyl, halogen, nitro, cyano, hydroxy, C$_{1-4}$ alkoxy, C$_{1-4}$ alkylthio, amino, mono- or di-C$_{1-4}$ alkyl-substituted amino, 5 to 7-membered cyclic amino, C$_{1-4}$ alkyl-carbonylamino, C$_{7-18}$ aralkyloxy, aminocarbonyloxy, mono- or di-C$_{1-4}$ alkyl-substituted aminocarbonyloxy, C$_{1-4}$ alkylsulfonylamino, C$_{1-4}$ alkoxy-carbonyl, carboxyl, C$_{1-6}$ alkyl-carbonyl, C$_{3-7}$ cycloalkyl-carbonyl, carbamoyl, mono- or di-C$_{1-4}$ alkyl-substituted carbamoyl, C$_{1-6}$ alkylsulfonyl, C$_{3-7}$ cycloalkylsulfonyl and a phenyl, naphthyl, mono- or di-phenyl-C$_{1-3}$ alkyl, phenoxy, benzoyl, phenoxycarbonyl, benzylcarbonyl, phenyl-C$_{1-4}$ alkyl-carbamoyl, phenylcarbamoyl, phenyl-C$_{1-4}$ alkyl-carbonylamino, benzoylamino, phenyl-C$_{1-4}$ alkylsulfonyl, phenylsulfonyl, phenyl-C$_{1-4}$ alkylsulfinyl, phenyl-C$_{1-4}$ alkylsulfonylamino or phenylsulfonylamino group which may be substituted by 1 to 4 substituents selected from the group consisting of a C$_{1-4}$ alkyl, C$_{1-4}$ alkoxy, halogen, hydroxy, benzyloxy, amino, mono- or di-C$_{1-4}$ alkyl-substituted amino, nitro, C$_{1-6}$ alkyl-carbonyl and benzoyl, (6) a C$_{7-18}$ aralkyl, C$_{6-14}$ aryl-C$_{2-12}$ alkenyl, C$_{6-14}$ aryl-C$_{2-12}$ alkynyl or C$_{3-7}$ cycloalkyl-C$_{1-6}$ alkyl group which may be substituted by 1 to 5 substituents selected from the group consisting of a C$_{1-4}$ alkyl, halogen, nitro, cyano, hydroxy, C$_{1-4}$ alkoxy, C$_{1-4}$ alkylthio, amino, mono- or di-C$_{1-4}$ alkyl-substituted amino, 5 to 7-membered cyclic amino, C$_{1-4}$ alkyl-carbonylamino, C$_{7-18}$ aralkyloxy, aminocarbonyloxy, mono- or di-C$_{1-4}$ alkyl-substituted aminocarbonyloxy, C$_{1-4}$ alkylsulfonylamino, C$_{1-4}$ alkoxy-carbonyl, carboxyl, C$_{1-6}$ alkyl-carbonyl, C$_{3-7}$ cycloalkyl-carbonyl, carbamoyl, mono- or di-C$_{1-4}$ alkyl-substituted carbamoyl, C$_{1-6}$ alkylsulfonyl, C$_{3-7}$ cycloalkylsulfonyl and a phenyl, naphthyl, mono- or di-phenyl-$C_{1-3}$ alkyl, phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino group which may be substituted by 1 to 4 substituents selected from the group consisting of a $C_{1-4}$ alkyl, $C_{1-4}$ alkoxy, halogen, hydroxy, benzyloxy, amino, mono- or di-$C_{1-4}$ alkyl-substituted amino, nitro, $C_{1-6}$ alkyl-carbonyl and benzoyl, (7) a $C_{1-8}$ alkyl-carbonyl or $C_{6-14}$ aryl-carbonyl group which may be substituted by 1 to 3 substituents selected from the group consisting of a halogen, amino, mono- or di-$C_{1-6}$ alkyl substituted amino and $C_{1-4}$ alkoxy, (8) a $C_{1-7}$ alkylsulfonyl or $C_{6-14}$ arylsulfonyl group which may be substituted by 1 to 3 substituents selected from the group consisting of a halogen, amino, mono- or di-$C_{1-6}$ alkyl substituted amino and $C_{1-4}$ alkoxy, (9) a $C_{1-7}$ alkylphosphonyl or $C_{6-14}$ arylphosphonyl group which may be substituted by 1 to 3 substituents selected from the group consisting of a halogen, amino, mono- or di-$C_{1-6}$ alkyl substituted amino and $C_{1-4}$ alkoxy, (10) a $C_{1-8}$ alkoxy-carbonyl or $C_{7-18}$ aralkyloxycarbonyl group which may be substituted by 1 to 3 substituents selected from the group consisting of a halogen, amino, mono- or di-$C_{1-6}$ alkyl substituted amino and $C_{1-4}$ alkoxy, (11) heterocyclic-carbonyl group which may be substituted by 1 to 3 substituents selected from the group consisting of a halogen, amino, mono- or di-$C_{1-6}$ alkyl substituted amino and $C_{1-4}$ alkoxy, (12) carbamoyl group which may be substituted by 1 to 3 substituents selected from the group consisting of a halogen, amino, mono- or di-$C_{1-6}$ alkyl substituted amino and $C_{1-4}$ alkoxy, (13) mono- or di-$C_{1-4}$ alkyl-carbamoyl group which may be substituted by 1 to 3 substituents selected from the group consisting of a halogen, amino, mono- or di-$C_{1-6}$ alkyl substituted amino and $C_{1-4}$ alkoxy, or (14) formyl; $R^2$ is (1') a hydrogen atom, (2') a straight-chain or branched $C_{1-11}$ alkyl, $C_{2-4}$ alkenyl or $C_{2-4}$ alkynyl group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, 5 to 7-membered cyclic amino, $C_{1-4}$ alkyl-carbonylamino, $C_{1-4}$ alkylsulfonylamino, $C_{1-4}$ alkoxy-carbonyl, carboxyl, $C_{1-6}$ alkyl-carbonyl, carbamoyl, mono- or di-$C_{1-4}$ alkyl-substituted carbamoyl, $C_{1-6}$ alkylsulfonyl, $C_{1-4}$ alkylenedioxy and heterocyclic group, (3') a $C_{3-7}$ monocyclic cycloalkyl group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, 5 to 7-membered cyclic amino, $C_{1-4}$ alkyl-carbonylamino, $C_{1-4}$ alkylsulfonylamino, $C_{1-4}$ alkoxy-carbonyl, carboxyl, $C_{1-6}$ alkyl-carbonyl, carbamoyl, mono- or di-$C_{1-4}$ alkyl-substituted carbamoyl, $C_{1-6}$ alkylsulfonyl, $C_{1-4}$ alkylenedioxy and heterocyclic group, (4') a $C_{8-14}$ bridge ring saturated hydrocarbon group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, 5 to 7-membered cyclic amino, $C_{1-4}$ alkyl-carbonylamino, $C_{1-4}$ alkylsulfonylamino, $C_{1-4}$ alkoxy-carbonyl, carboxyl, $C_{1-6}$ alkyl-carbonyl, carbamoyl, mono- or di-$C_{1-4}$ alkyl-substituted carbamoyl, $C_{1-6}$ alkylsulfonyl, $C_{1-4}$ alkylenedioxy and heterocyclic group, (5') a phenyl or naphthyl group which may be substituted by 1 to 5 substituents selected from the group consisting of a $C_{1-4}$ alkyl, halogen, nitro, cyano, hydroxy, $C_{1-4}$ alkoxy, $C_{1-4}$ alkylthio, amino, mono- or di-$C_{1-4}$ alkyl-substituted amino, 5 to 7-membered cyclic amino, $C_{1-4}$ alkyl-carbonylamino, $C_{7-18}$ aralkyloxy, aminocarbonyloxy, mono- or di-$C_{1-4}$ alkyl-substituted aminocarbonyloxy, $C_{1-4}$ alkylsulfonylamino, $C_{1-4}$ alkoxy-carbonyl, carboxyl, $C_{1-6}$ alkyl-carbonyl, $C_{3-7}$ cycloalkyl-carbonyl, carbamoyl, mono- or di-$C_{1-4}$ alkyl-substituted carbamoyl, $C_{1-6}$ alkylsulfonyl, $C_{3-7}$ cycloalkylsulfonyl and a phenyl, naphthyl, mono- or di-phenyl-$C_{1-3}$ alkyl, phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino group which may be substituted by 1 to 4 substituents selected from the group consisting of a $C_{1-4}$ alkyl, $C_{1-4}$ alkoxy, halogen, hydroxy, benzyloxy, amino, mono- or di-$C_{1-4}$ alkyl-substituted amino, nitro, $C_{1-6}$ alkyl-carbonyl and benzoyl, (6') a $C_{7-18}$ aralkyl, $C_{6-14}$ aryl-$C_{2-12}$ alkenyl, $C_{6-14}$ aryl-$C_{2-12}$ alkynyl or $C_{3-7}$ cycloalkyl-$C_{1-6}$ alkyl group which may be substituted by 1 to 5 substituents selected from the group consisting of a $C_{1-4}$ alkyl, halogen, nitro, cyano, hydroxy, $C_{1-4}$ alkoxy, alkylthio, amino, mono- or di-$C_{1-4}$ alkyl-substituted amino, 5 to 7-membered cyclic amino, $C_{1-4}$ alkyl-carbonylamino, $C_{7-18}$ aralkyloxy, aminocarbonyloxy, mono- or di-$C_{1-4}$ alkyl-substituted aminocarbonyloxy, $C_{1-4}$ alkylsulfonylamino, $C_{1-4}$ alkoxy-carbonyl, carboxyl, $C_{1-6}$ alkyl-carbonyl, $C_{3-7}$ cycloalkyl-carbonyl, carbamoyl, mono- or di-$C_{1-4}$ alkyl-substituted carbamoyl, $C_{1-6}$ alkylsulfonyl, $C_{3-7}$ cycloalkylsulfonyl and a phenyl, naphthyl, mono- or di-phenyl-$C_{1-3}$ alkyl, phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino group which may be substituted by 1 to 4 substituents selected from the group consisting of a $C_{1-4}$ alkyl, $C_{1-4}$ alkoxy, halogen, hydroxy, benzyloxy, amino, mono- or di-$C_{1-4}$ alkyl-substituted amino, nitro, $C_{1-6}$ alkyl-carbonyl and benzoyl, $R^3$ and $R^4$ taken together with the adjacent nitrogen atom, form a 3- to 13-membered heterocyclic group having, other than carbon atoms and one nitrogen atom, 1 to 3 nitrogen, oxygen and/or sulfur atoms as hetero atoms, which may be substituted by 1 to 5 substituents selected from the group consisting of (1") a straight-chain or branched $C_{1-11}$ alkyl, $C_{2-4}$ alkenyl or $C_{2-4}$ alkynyl group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, 5 to 7-membered cyclic amino, $C_{1-4}$ alkyl-carbonylamino, $C_{1-4}$ alkylsulfonylamino, $C_{1-4}$ alkoxy-carbonyl, carboxyl, $C_{1-6}$ alkyl-carbonyl, carbamoyl, mono- or di-$C_{1-4}$ alkyl-substituted carbamoyl, $C_{1-6}$ alkylsulfonyl, $C_{1-4}$ alkylenedioxy and heterocyclic group, (2") a $C_{3-7}$ monocyclic cycloalkyl group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, 5 to 7-membered cyclic amino, $C_{1-4}$ alkyl-carbonylamino, $C_{1-4}$ alkylsulfonylamino, $C_{1-4}$ alkoxy-carbonyl, carboxyl, $C_{1-6}$ alkyl-carbonyl, carbamoyl, mono- or di-$C_{1-4}$ alkyl-substituted carbamoyl, $C_{1-6}$ alkylsulfonyl, $C_{1-4}$ alkylenedioxy and heterocyclic group, (3") a $C_{8-14}$ bridge ring saturated hydrocarbon group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, 5 to 7-membered cyclic amino, $C_{1-4}$ alkyl-carbonylamino, $C_{1-4}$ alkylsulfonylamino, $C_{1-4}$ alkoxy-carbonyl, carboxyl, $C_{1-6}$ alkyl-carbonyl, carbamoyl, mono- or di-$C_{1-4}$ alkyl-substituted carbamoyl, $C_{1-6}$ alkylsulfonyl, $C_{1-4}$ alkylenedioxy and heterocyclic group, (4") a phenyl or naphthyl group which may be substituted by 1 to 5 substituents selected from the group consisting of a $C_{1-4}$ alkyl, halogen, nitro, cyano, hydroxy, $C_{1-4}$ alkoxy, $C_{1-4}$ alkylthio, amino, mono- or di-$C_{1-4}$ alkyl-substituted amino, 5 to 7-membered cyclic amino, $C_{1-4}$ alkyl-carbonylamino, $C_{7-18}$ aralkyloxy, aminocarbonyloxy, mono- or di-$C_{1-4}$ alkyl-substituted aminocarbonyloxy, $C_{1-4}$ alkylsulfonylamino, $C_{1-4}$ alkoxy-carbonyl, carboxyl, alkyl-carbonyl, $C_{3-7}$ cycloalkyl-carbonyl, carbamoyl, mono- or di-$C_{1-4}$ alkyl-substituted carbamoyl, $C_{1-6}$ alkylsulfonyl, $C_{3-7}$ cycloalkylsulfonyl, $C_{1-4}$ alkylenedioxy and a phenyl, naphthyl, mono- or di-phenyl-$C_{1-3}$ alkyl, phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino group which may be substituted by 1 to 4 substituents selected from the group consisting of a $C_{1-4}$ alkyl, $C_{1-4}$ alkoxy, halogen, hydroxy, benzyloxy, amino, mono- or di-$C_{1-4}$ alkyl-substituted amino, nitro, $C_{2-6}$ alkyl-carbonyl and benzoyl, (5") a $C_{7-18}$ aralkyl, $C_{6-14}$ aryl-$C_{2-12}$ alkenyl, $C_{6-14}$ aryl-$C_{2-12}$ alkynyl or $C_{3-7}$ cycloalkyl-$C_{1-6}$ alkyl group which may be substituted by 1 to 5 substituents selected from the group consisting of a $C_{1-4}$ alkyl, halogen, nitro, cyano, hydroxy, $C_{1-4}$ alkoxy, $C_{1-4}$ alkylthio, amino, mono- or di-$C_{1-4}$ alkyl-substituted amino, 5 to 7-membered cyclic amino, $C_{1-4}$ alkyl-carbonylamino, $C_{7-18}$ aralkyloxy, aminocarbonyloxy, mono- or di-$C_{1-4}$ alkyl-substituted aminocarbonyloxy, $C_{1-4}$ alkylsulfonylamino, $C_{1-4}$ alkoxy-carbonyl, carboxyl, $C_{1-6}$ alkyl-carbonyl, $C_{3-7}$ cycloalkyl-carbonyl, carbamoyl, mono- or di-$C_{1-4}$ alkyl-substituted carbamoyl, $C_{1-6}$ alkylsulfonyl, $C_{3-7}$ cycloalkylsulfonyl, $C_{1-4}$ alkylenedioxy and a phenyl, naphthyl, mono- or di-phenyl-$C_{1-3}$ alkyl, phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino group which may be substituted by 1 to 4 substituents selected from the group consisting of a $C_{1-4}$ alkyl, $C_{1-4}$ alkoxy, halogen, hydroxy, benzyloxy, amino, mono- or di-$C_{1-4}$ alkyl-substituted amino, nitro, $C_{1-6}$ alkyl-carbonyl and benzoyl, (6") halogen atom, (7") nitro group, (8") cyano group, (9") hydroxyl group, (10") $C_{1-4}$ alkoxy group, (11") $C_{1-4}$ alkylthio group, (12") amino group, (13") mono or di $C_{1-4}$ alkylamino group, (14") $C_{1-4}$ alkyl-carbonylamino group, (15") $C_{1-4}$ alkyl-sulfonylamino group, (16") $C_{1-4}$ alkoxy-carbonyl group, (17") carboxyl group, (18") formyl group, (19") $C_{1-6}$ alkyl-carbonyl group, (20") $C_{1-4}$ alkyl-carbonyloxy group, (21") ω-oxo-ω -(tetrahydrobenzazepinyl) $C_{1-6}$ alkyl group, (22") benzoyl group which may be substituted by 1 to 3 substituents selected from the group consisting of $C_{1-4}$ alkyl, halogen, $C_{1-4}$ alkoxy, mono- or di-$C_{1-4}$ alkylamino, 5- to 7-membered cyclic amino group, nitro and hydroxy, (23") carbamoyl group, (24") mono or di $C_{1-4}$ alkyl-carbamoyl group, (25") $C_{1-6}$ alkylsulfonyl group, (26") oxo group and (27") heterocyclic group selected from pyridinyl, pyrazinyl, pyrimidinyl, quinolinyl, isoquinolinyl, naphthylidinyl, benzothiazolyl, benzoxazolyl, furanyl and thiophenyl; ring A is a benzene ring which may be further substituted by 1 to 3 substituents selected from the group consisting of a $C_{1-4}$ alkyl, halogen, nitro, cyano, hydroxy, $C_{1-4}$ alkoxy, $C_{1-4}$ alkylthio, amino, mono- or di-$C_{1-4}$ alkyl-substituted amino, 5 to 7-membered cyclic amino, $C_{1-4}$ alkyl-carbonylamino, $C_{7-18}$ aralkyloxy, aminocarbonyloxy, mono- or di-$C_{1-4}$ alkyl-substituted aminocarbonyloxy, $C_{1-4}$ alkylsulfonylamino, $C_{1-4}$ alkoxy-carbonyl, carboxyl, $C_{1-6}$ alkyl-carbonyl, $C_{3-7}$ cycloalkyl-carbonyl, carbamoyl, mono- or di-$C_{1-4}$ alkyl-substituted carbamoyl, $C_{1-6}$ alkylsulfonyl, $C_{3-7}$ cycloalkylsulfonyl and a phenyl, naphthyl, mono- or di-phenyl-$C_{1-3}$ alkyl, phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino which may be substituted by 1 to 4 substituents selected from the group consisting of a $C_{1-4}$ alkyl, $C_{1-4}$ alkoxy, halogen, hydroxy, benzyloxy, amino, mono- or di-$C_{1-4}$ alkyl-substituted amino, nitro, $C_{1-6}$ alkyl-carbonyl and benzoyl.

3. A compound as claimed in claim 1, wherein $R^1$ is (i) hydrogen atom, (ii) a $C_{1-4}$ alkyl group which may be substituted with a hydroxy group, (iii) a $C_{2-4}$ alkynyl group, (iv) a phenyl-$C_{1-3}$ alkyl group which may be substituted with one to three substituents selected from the group consisting of a halogen, nitro, cyano, $C_{1-4}$ alkyl, $C_{1-4}$ alkoxy, hydroxy and phenylmethoxy group, (v) formyl group, (vi) a $C_{1-4}$ alkyl-carbonyl group, (vii) benzoyl group, (viii) a $C_{1-4}$ alkoxy-carbonyl group, (ix) pyridylcarbonyl group, or (x) a mono- or di-$C_{1-4}$ alkylcarbamoyl group.

4. A compound as claimed in claim 1, wherein $R^1$ is (i) H, (ii) a straight-chain or branched $C_{1-4}$ alkyl group, (iii) a phenyl-$C_{1-3}$ alkyl group which may be substituted by 1 to 3 substituents selected from the group consisting of $C_{1-4}$ alkyl, halogen, nitro, cyano, hydroxy, $C_{1-4}$ alkoxy and $C_{7-18}$ aralkyloxy, (iv) a naphthyl-$C_{1-3}$ alkyl group, (v) a $C_{1-3}$ alkyl-carbonyl, (vi) a phenyloxycarbonyl or (vii) a $C_{1-4}$ alkoxy-carbonyl.

5. A compound as claimed in claim 1, wherein $R^1$ is (i) H, (ii) a straight-chain or branched $C_{1-4}$ alkyl group, (iii) a $C_{1-4}$ alkyl-carbonyl group or (iv) a phenyl-$C_{1-3}$ alkyl group which may be substituted by a $C_{1-4}$ alkoxy.

6. A compound as claimed in claim 1, wherein k is a whole number of 0 to 2 and m is a whole number of 2 to 5.

7. A compound as claimed in claim 1, wherein the moiety in the formula [ I ] of

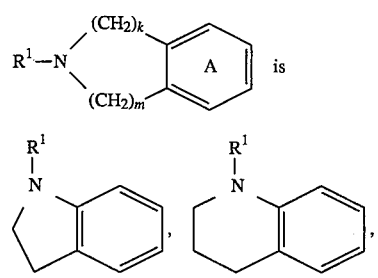

-continued

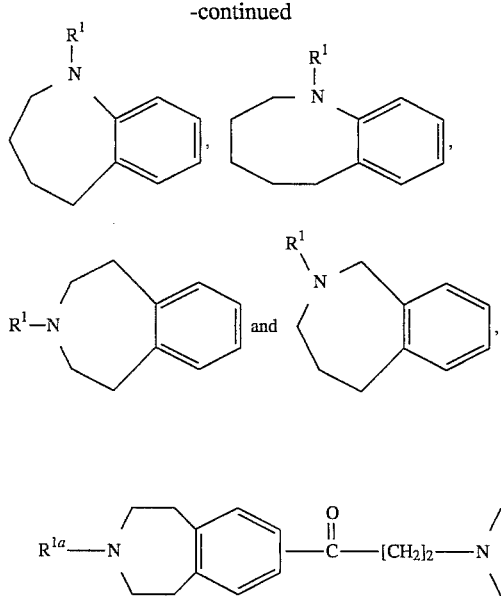

and R¹ is (i) H, (ii) a straight-chain or branched C₁₋₄ alkyl group, (iii) a C₁₋₃ alkyl-carbonyl group or (iv) a phenyl-C₁₋₃ alkyl group which may be substituted by a C₁₋₄ alkoxy.

8. A compound as claimed in claim 1, wherein the ring A is a benzene ring.

9. A compound as claimed in claim 1, wherein n is a whole number of 1 to 6.

10. A compound as claimed in claim 1, wherein R² is hydrogen atom or phenyl group.

11. A compound as claimed in claim 1, wherein R² is H.

12. A compound as claimed in claim 1, wherein R³ and R⁴, taken together with the adjacent nitrogen atom, form (i') a piperidinyl group which may be substituted with a phenyl-C₁₋₃ alkyl group, a hydroxy group or oxo, (ii') 4-oxo-1-phenyl-1,3,8-triazaspiro[4,5]decan-8-yl, (iii') 1,2,3,4-tetrahydroisoquinolin-2-yl, (iv') pyrrolidinyl, (v') morpholinyl, (vi') a homopiperazinyl group which may be substituted with a phenyl-C₁₋₃ alkyl group, or (vii') a piperazinyl group which may be substituted with (1) a phenyl-C₁₋₃ alkyl group which may be substituted with a halogen atom, a C₁₋₄ alkoxy group or a C₁₋₄ alkylenedioxy group, (2) pyridyl group, (3) a benzoyl group which may be substituted with a halogen atom, (4) a C₁₋₄ alkyl group which may be substituted with hydroxy group, 3-oxo-3[3-(phenylmethyl)- 2,3,4,5-tetrahydro-1H-3-benzazepin-7-yl] propyl, pyridyl, furyl or 2-methyl-thiazol- 4-yl group, (5) formyl group, (6) a C₁₋₆ alkyl-carbonyl group, (7) a phenyl group which may be substituted with a halogen atom, (8) hydroxyl group or (9) a diphenyl-C₁₋₃ alkyl group.

13. A compound as claimed in claim 1, wherein R³ and R⁴ taken together with the adjacent nitrogen atom, form a pyrrolidinyl, piperidinyl, piperazinyl, morpholinyl or 1,2,3,4-tetrahydroquinolinyl group which may be substituted by 1 or 2 substituents selected from the group consisting of (1) formyl, (2) C₁₋₄ alkylcarbonyl, (3) hydroxy, (4) oxo, (5) pyridyl, (6) benzoyl which may be substituted by 1 to 3 halogen atoms, (7) straight-chain or branched C₁₋₇ alkyl which may be substituted by 1 to 3 substituents selected from the group consisting of hydroxy, pyridyl, furyl, thiazol-4-yl and 2-methyl-thiazol-4-yl, (8) phenyl which may be substituted by 1 to 3 substituents selected from the group consisting of halogen, hydroxy and C₁₋₄ alkylenedioxy, (9) C₇₋₁₈ aralkyl which may be substituted by 1 to 3 substituents selected from the group consisting of halogen, hydroxy and C₁₋₄ alkylenedioxy and (10) ω-oxo-ω-(tetrahydrobenzazepinyl) C₁₋₆ alkyl.

14. A compound as claimed in claim 1, wherein R³ and R⁴ taken together with the adjacent nitrogen atom, form a 4-(phenylmethyl)-piperazin-1-yl or 4-[(2-methylthiazol-4-yl)methyl]-piperazin-1-yl.

15. A compound as claimed in claim 1, wherein n is a whole number of 2 to 5.

16. A compound as claimed in claim 1, which is a compound of the formula:

$$R^{1a}-N \underset{}{\overset{}{\bigcirc}} -\overset{O}{\underset{\|}{C}}-[CH_2]_2-N \underset{}{\overset{}{\bigcirc}} N-CH_2-\underset{}{\overset{}{\bigcirc}}$$

wherein R¹ᵃ is (i) a C₁₋₄ alkyl group or (ii) a phenyl-C₁₋₃ alkyl group which may be substituted with a C₁₋₄ alkoxy group, or a pharmaceutically acceptable salt thereof.

17. A compound as claimed in claim 1, which is 1-[3-[(4-methoxyphenyl)methyl]-2,3,4,5-tetrahydro-1H-3-benzazepin- 7-yl]-3-[4-(phenylmethyl)piperazin-1-yl]-1-propanone or a pharmaceutically acceptable salt thereof.

18. A compound as claimed in claim 1, which is 1-[3-(2-phenylethyl)-2,3,4,5-tetrahydro-1H-3-benzazepin-7-yl] -3-[4-(phenylmethyl)piperazin-1-yl]-1-propanone or a pharmaceutically acceptable salt thereof.

19. A compound as claimed in claim 1, which is 1-[3-(2-methylpropyl)-2,3,4,5-tetrahydro-1H-3-benzazepin-7-yl] -3-[4-(phenylmethyl)piperazin-1-yl]-1-propanone or a pharmaceutically acceptable salt thereof.

20. A compound as claimed in claim 1, which is 1-[3-(phenylmethyl)- 2,3,4,5-tetrahydro-1H-3-benzazepin-7-yl] -3-[4-(phenylmethyl)piperazin-1-yl]-1-propanone or a pharmaceutically acceptable salt thereof.

21. A compound as claimed in claim 1, which is 1-[1-(phenylmethyl)- 2,3-dihydro-1H-indol-5-yl]-3-[4-(phenylmethyl)piperazin- 1-yl]-1-propanone or a pharmaceutically acceptable salt thereof.

22. A compound as claimed in claim 1, which is 1-[2-(phenylmethyl)- 2,3,4,5-tetrahydro-1H-2-benzazepin-8-yl] -3-[4-(phenylmethyl)piperazin-1-yl]-1-propanone or a pharmaceutically acceptable salt thereof.

23. A compound as claimed in claim 1, which is 3-[4-[(2-methylthiazol-4-yl)methyl]piperazin-1-yl]-1-[3-(phenylmethyl)- 2,3,4,5-tetrahydro-1H-3-benzazepin-7-yl] -1-propanone or a pharmaceutically acceptable salt thereof.

24. A compound of the formula:

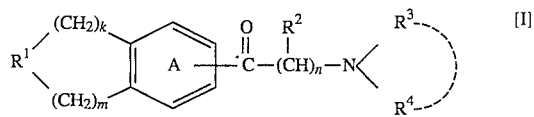

wherein R¹ is H, an optionally substituted hydrocarbon group or an optionally substituted acyl group; ring A is an optionally substituted benzene ring; n is a whole number of 1 to 10; $R^2$, $R^3$ and $R^4$ are independently H or an optionally substituted hydrocarbon group, provided one of $R^3$ and $R^4$ is H or a straight-chain or branched $C_{1-4}$ alkyl group and the other is a straight-chain or branched $C_{1-4}$ alkyl group, a phenyl-$C_{1-3}$ alkyl group or a naphthyl-$C_{1-3}$ alkyl group; the $R^2$'s may be different from one another in the repetition of n; k is a whole number of 0 to 3; and m is a whole number of 1 to 8; provided that when k=0 and m=2, n is a whole number of not less than 2; and provided that k+m=2 to 5; or a pharmaceutically acceptable salt thereof.

25. A pharmaceutical composition for a disease caused by acetylcholinesterase activity which contains an effective cholinesterase inhibiting amount of a compound of the formula as claimed in claim 1 or a pharmaceutically acceptable salt thereof and a pharmacologically acceptable carrier.

26. A pharmaceutical composition as claimed in claim 25, in which the disease is senile dementia and/or Alzheimer's disease.

27. A method of treating a disease caused by acetylcholinesterase activity which comprises administering a therapeutically effective amount of a compound of the formula:

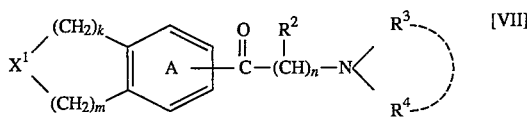

wherein $X^1$ is $R^1$—N ($R^1$ is H, an optionally substituted hydrocarbon group or an optionally substituted acyl group); ring A is an optionally further substituted benzene ring; n is a whole number of 1 to 10; $R^2$, $R^3$ and $R^4$ are independently H or an optionally substituted hydrocarbon group; $R^3$ and $R^4$ may form an optionally substituted heterocyclic group, taken together with the adjacent nitrogen atom; $R^2$'s may be different from one another in the repetition of n; k is a whole number of 0 to 3; and m is a whole number of 1 to 8, and provided that k+m=2 to 5; or a pharmaceutically acceptable salt thereof, together with a pharmaceutically acceptable carrier to a mammal suffering from such disease.

* * * * *

UNITED STATES PATENT AND TRADEMARK OFFICE
CERTIFICATE OF CORRECTION

PATENT NO. : 5,462,934
DATED : October 31, 1995
INVENTOR(S) : Giichi GOTO et al.

It is certified that error appears in the above-indentified patent and that said Letters Patent is hereby corrected as shown below:

Column 190, lines 60-65, Claim 24, contains a typographical error in the formula. Delete the formula in its entirety and insert --
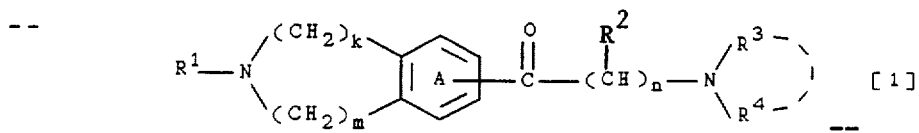
--

Signed and Sealed this

Twenty-first Day of January, 1997

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO.   : 5,462,934
DATED        : October 31, 1995
INVENTOR(S)  : Giichi GOTO et al.

It is certified that error appears in the above-indentified patent and that said Letters Patent is hereby corrected as shown below:

Column 191, line 15, claim 25, after "formula" insert --[I]--.

Signed and Sealed this

Eighth Day of April, 1997

Attest:

BRUCE LEHMAN

Attesting Officer   Commissioner of Patents and Trademarks